(12) United States Patent
Tangy et al.

(10) Patent No.: US 9,499,799 B2
(45) Date of Patent: *Nov. 22, 2016

(54) CELLS AND METHODOLOGY TO GENERATE NON-SEGMENTED NEGATIVE-STRAND RNA VIRUSES

(71) Applicants: Institut Pasteur, Paris (FR); Centre National De La Recherche Scientifique, Paris (FR)

(72) Inventors: Frederic Tangy, Les Lilas (FR); Pierre Charneau, Paris (FR); Yves Jacob, Maintenon (FR)

(73) Assignees: Institut Pasteur, Paris (FR); Centre National De La Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/054,748

(22) Filed: Oct. 15, 2013

(65) Prior Publication Data
US 2014/0051148 A1    Feb. 20, 2014

Related U.S. Application Data

(63) Continuation of application No. 12/448,468, filed as application No. PCT/IB2007/004444 on Dec. 21, 2007, now Pat. No. 8,586,364.

(30) Foreign Application Priority Data

Dec. 22, 2006   (EP) .................................... 06292025

(51) Int. Cl.
*C12N 7/00* (2006.01)
*C07K 14/005* (2006.01)
*C12N 15/86* (2006.01)

(52) U.S. Cl.
CPC ............... *C12N 7/00* (2013.01); *C07K 14/005* (2013.01); *C12N 15/86* (2013.01); *C12N 2740/16021* (2013.01); *C12N 2740/16043* (2013.01); *C12N 2740/16052* (2013.01); *C12N 2760/18022* (2013.01); *C12N 2760/18422* (2013.01); *C12N 2830/48* (2013.01)

(58) Field of Classification Search
CPC ................... C12N 15/86; C12N 2740/16021; C12N 2830/48; C12N 2740/16052; C12N 2740/16043; C12N 2760/18022; C12N 2760/18422
See application file for complete search history.

(56) References Cited

U.S. PATENT DOCUMENTS 7,851,214 B2 * 12/2010 Billeter et al. ............. 435/320.1
2012/0082693 A1   4/2012 Van Der Werf et al.

FOREIGN PATENT DOCUMENTS

| WO | 97/06270 | | 2/1997 |
|---|---|---|---|
| WO | 01/27304 | A2 | 4/2001 |
| WO | 01/96376 | A2 | 12/2001 |
| WO | 04/001051 | A2 | 12/2003 |
| WO | 2004/113517 | A2 | 12/2004 |
| WO | 2005/111221 | A1 | 11/2005 |

OTHER PUBLICATIONS

Otter-Nilson et al ("Protein expression in mammalian cells", in Higgens et al, Protein Expression: A Practical Approach, Oxford University Press, 1999, p. 1-27).*
Arhel, N. et al., "Nuclear import defect of human immunodeficiency virus type 1 DNA flap mutants is not dependent on the viral strain or target cell type," Journal of Virology, vol. 80, No. 20, pp. 10262-10269 (2006).
Barry, S. C., et al., "Lentivirus vectors encoding both central polypurine tract and posttranscriptional regulatory element provide enhanced transduction and transgene expression," Human Gene Therapy, vol. 12, No. 9, pp. 1103-1108 (2001).
Breckpot, K., et al., "Lentivirally transduced dendritic cells as a tool for cancer immunotherapy," The Journal of Gene Medicine, vol. 5, No. 8, pp. 654-667 (2003).
Combredet, C, et al., "A Molecularly Cloned Schwarz Strain of Measles Virus Vaccine Induces Strong Immune Responses in Macaques and Transgenic Mice," Journal of Virology, vol. 77, No. 21, pp. 11546-11554 (2003).
Radecke, F., et al., "Rescue of Measles Viruses From Cloned DNA," EMBO Journal, vol. 14, No. 23, pp. 5773-5784 (1995).
Whitwam, T., et al., "Identification of a central DNA flap in feline immunodeficiency virus," Journal of Virology, vol. 75, No. 19, pp. 9407-9414 (2001).
Sirven A., et al., Molecular Therapy, Apr. 2001, vol. 3, No. 4, pp. 438-448.
Tangy et al., "Live Attenuated Measles Vaccine as a Potential Multivalent Pediatric Vaccination Vector," Viral Immunology, 2005, vol. 18, No. 2, pp. 317-326.
Dardalhon et al., "Lentivirus-mediated gene transfer in primary T cells is enhanced by a central DNA flap," Gene Therapy, 2001, vol. 8, pp. 190-198.
Moll, M., et al., "Polarized Glycoprotein Targeting Affects the Spread of Measles Virus in vitro and in vivo," Journal of General Virology (2004) 85: 1019-1027.
Takeuchi, Kaoru et al., "Toward Understanding the Pathogenicity of Wild-Type Measles Virus by Reverse Genetics," Jpn. J. Infect. Dis., (2002) 55:143-149.
Neumann, G. et al., "A Decade After the Generation of a Negative-Sense RNA Virus From Cloned cDNA—What Have We Learned?," Journal of General Virology, (2000) 83: 2635-2662.

* cited by examiner

*Primary Examiner* — Shanon A Foley
(74) *Attorney, Agent, or Firm* — Law Office of Salvatore Arrigo and Scott Lee, LLP

(57) ABSTRACT

The present invention relates to recombinant cells as well as to methods for the generation of non-segmented negative-sense single-stranded RNA viruses (NNV or mononegavirales) from cloned deoxyribonucleic acid (cDNA), especially from measles virus and in particular from attenuated strains such as those approved for vaccination, in particular from the attenuated Schwarz measles virus and various recombinant Schwarz measles-based viruses expressing heterologous sequences. Such rescued viruses can be used, after amplification, as vaccines for immunization against measles and/or against the heterologous peptides or proteins expressed.

22 Claims, 2 Drawing Sheets

CELLS AND METHODOLOGY TO GENERATE NON-SEGMENTED NEGATIVE-STRAND RNA VIRUSES

This is a continuation of application Ser. No. 12/448,468, filed Dec. 18, 2009 (now U.S. Pat. No. 8,586,364 B2), which is the national stage of International Application No. PCT/IB2007/004444, filed Dec. 21, 2007, which claims priority to European Patent Office Application No. 06292025.1, filed Dec. 22, 2006, all of which are hereby incorporated herein by reference.

The present invention relates to recombinant cells as well as to methods for the generation of non-segmented negative-sense single-stranded RNA viruses (NNV or mononegavirales) from cloned deoxyribonucleic acid (cDNA), especially from measles virus and in particular from attenuated strains such as those approved for vaccination, in particular from the attenuated Schwarz measles virus and various recombinant Schwarz measles-based viruses expressing heterologous sequences. Such rescued viruses can be used, after amplification, as vaccines for immunization against measles and/or against the heterologous peptides or proteins expressed.

Live attenuated RNA viruses make very efficient vaccines. Among these, measles vaccine has been used in hundreds of millions of children and has been proven to be effective and safe. This vaccine induces life-long immunity after one or two injections. It is easily produced on a large scale at low cost in most countries. These advantages make measles virus, especially attenuated vaccine strains, a good candidate vector to immunize children but even in some circumstances adult populations, against both measles and/or other infectious pathologies, especially viral pathologies such as AIDS (retroviruses), flavivirus or coronavirus (SARS) diseases.

Live attenuated measles virus has been used as vaccine since the 1960s and is one of the most effective and safest human vaccines. Vaccination campaigns have been very effective to control measles in developed countries. However, due to inadequate distribution of the vaccine in developing countries, measles still infects approximately 45 million individuals and is responsible for the death of 700,000 children per year. The WHO has therefore stepped up its global vaccination program for the next 10-20 years (C.D.C., 2005). Taking advantage of the WHO campaigns, the use of vaccine vectors derived from measles vaccine would allow in certain regions of the world the simultaneous immunization of children against measles and other infectious diseases with new multivalent, especially bivalent pediatric vaccines that are both safe and effective.

Measles virus (MV) belongs to the genus *Morbillivirus* in the family *Paramyxoviridae*. It is an enveloped virus with a non-segmented RNA genome of negative polarity (15,894 bp). Measles can only be contracted once as the immune system mounts a strong specific response and establishes life-long memory protecting against re-infection. Such protection is based on both the production of antibodies and memory cytotoxic CD8+ T lymphocytes (CTL). Pathogenic strains strongly disrupt hematopoiesis (Arneborn et al., 1983; Kim et al., 2002; Okada et al., 2000) thus resulting in transitory immunosuppression responsible for most deaths due to measles infection in developing countries. In contrast to primary strains, attenuated strains do not induce immunosuppression (Okada et al., 2001).

The Edmonston strain of measles virus was isolated in 1954 by culture in primary human cells (Enders et al., 1954). Adaptation to chicken embryonic fibroblasts produced vaccine seeds that were furthermore attenuated by subsequent passages in chicken embryonic fibroblasts (Schwarz et al., 1962). The Schwarz and Moraten strains that possess identical nucleotide sequences (Parks et al., 2001a; Parks et al., 2001b) constitute the most frequently used measles vaccine. Vaccination with one or two injections induces life-long immunity (Griffin et al., 2001; Hilleman et al., 2002). Persistence of CD8 cells and antibodies has been demonstrated up to 25 years after vaccination (Ovsyannikova et al., 2003). The measles vaccine is easily produced on a large scale in most countries and may be made available at low cost. Attenuation of the viral genome results from an advantageous combination of multiple mutations. Thus, the vaccine is very stable and reversion of vaccine strains has never been observed to date (Hilleman et al., 2002). In addition, the virus replicates only in the cytoplasm, eliminating any risk of integrating into chromosomes of the host genome. These features make live attenuated measles vaccine an excellent candidate for the development of a multivalent vaccine vector. To this end, an infectious cDNA corresponding to the Edmonston B MV strain antigenome has been cloned and a reverse genetics technique enabling the production of the corresponding virus was established (Radecke et al., 1995).

The inventors have previously developed a vector using the Schwarz MV, the most commonly used measles vaccine in the world (Combredet et al., 2003). This vector can stably express a variety of genes or combination of large genes for more than 12 passages. Recombinant MV vectors containing 4,000-5,000 additional nucleotides were produced, representing an additional 30% of genome. These viruses were produced in cell culture at titers comparable to standard MV. After 12 passages and an amplification factor of $10^{20}$, more than 96% of the infected cells continued to express the additional genes. This remarkably stable expression, also observed for other members of the *Mononegavirales* (Schnell et al., 1996) is likely due to the absence of geometric constraints on the size of the genome by these helicoid nucleocapsid viruses, in contrast to viruses with icosahedral capsids. Moreover, MV infects cells of the immune system (macrophages and dendritic cells), thus delivering the cargo antigens directly to the most effective antigen presenting cells, a major advantage for a vaccine vector. Finally, the MV genome is small, thus avoiding the response to the vector overwhelming the response to transgenes.

Based on the assumption that the safety and efficacy of an attenuated strain ultimately depends on its genome sequence, the inventors cloned the infectious cDNA corresponding to the antigenome of the Schwarz/Moraten measles virus from virus particles purified from an industrial preparation of the Schwarz vaccine with optimal procedures to maintain fidelity (Combredet et al., 2003). To optimize the output of the reverse genetics system, the antigenomic viral cDNA was placed under the control of the T7 phage RNA polymerase promoter with an additional GGG motif required for optimal efficacy. To allow exact cleavage of the viral RNA, a hammerhead ribozyme was inserted between the GGG motif and the first viral nucleotide, and the ribozyme from hepatitis delta virus was placed downstream of the last viral nucleotide. The resulting pTM-MVSchw plasmid enabled the production of the corresponding virus using a previously described reverse genetics system based on the transfection of human helper cells (Radecke et al., 1995). To prevent adaptation of the recombinant vaccine to non-certified cells, the helper cells transfected with cDNA were co-cultivated with chicken embryonic fibroblasts, the cells in which the virus was originally selected and in which it is currently produced. After several passages of recombinant virus the sequence of its entire genome was found identical to the original sequence (Combredet et al., 2003). The immunogenicity of the virus rescued from pTM-MVSchw plasmid was evaluated in transgenic mice and macaques and compared with the industrially manufactured Schwarz vaccine. All vaccinated macaques developed anti-MV antibodies and specific cellular responses. No differences were observed between the Schwarz virus produced from the cDNA and the original vaccine, indicating that the cloned virus had the same immunogenicity as the parental vaccine (Combredet et al., 2003). This molecular clone allows the production of the Schwarz measles vaccine without depending on the seeding stocks.

The pTM-MVSchw plasmid was modified for the expression of foreign genes by the introduction of additional transcriptional units (ATU) at different positions of the genome. These ATUs are multi-cloning site cassettes inserted for example in a copy of the intergenic N-P region of the viral genome (containing the cis acting sequences required for transcription). The enhanced green fluorescent protein (eGFP) gene was inserted into this cassette. The ATU was introduced into the pTM-MVSchw plasmid in two positions (between the P and M genes and between the H and L genes). Irrespective of the additional sequence, the total number of antigenomic nucleotides must be maintained as a multiple of six to fulfill the “rule of 6 nucleotides” that optimizes viral replication (Calain et al., 1993). The GFP transgene was expressed in all infected cell types, confirming that the recombinant Schwarz measles virus works as a vector. This vector allows the design of combined vaccines based on a live attenuated approved vaccine strain that is currently globally in use. This work is the object of international application WO 2004/000876 which is incorporated herewith by reference.

The use of such MV-based live recombinant vaccines at large scale depends on the possibility of growing them stably and at good titers on certified cells (such as primary chicken embryonic fibroblasts (CEF) or human diploid MRC5). These cells usually produce MV at moderate titers as compared to laboratory cell lines, such as African green monkey Vero cells, that produce at high titers. Thus, the initial seed must be obtained at a relatively high titer. This initial seed is produced from cDNA by reverse genetics.

While positive-strand RNA or DNA viruses can be easily obtained in vitro after transfection of their engineered infectious cDNA or DNA in appropriate cells, the negative-strand RNA viruses cannot be rescued directly by reverse genetics from their cDNA. The genome of negative-strand RNA viruses is not able to initiate in vitro an infectious cycle because it does not code directly for proteins. Both transcription and replication require a transcriptase-polymerase enzymatic complex contained in the nucleoproteins encapsidating the viral genome (RNP complex). Thus, the generation of recombinant negative-strand RNA viruses from cDNA involves reconstitution of active RNPs from individual components: RNA and proteins (Fields B. N. et al—Lippincott Raven publishers 1996, p. 1953-1977).

For the last 15 years, a remarkable set of work from numerous laboratories has allowed the establishment of different systems for rescuing almost all negative-strand RNA viruses from their cDNA (for review see Conzelmann). In contrast to the viruses with segmented genomes, the RNPs of non-segmented negative-strand RNA viruses (*Mononegavirales*) are tightly structured and contain, in addition to the nucleoprotein (N), the assembly and polymerase cofactor phosphoprotein (P) and the viral RNA polymerase large protein (L), The first infectious *Mononegavirales*, the rabies rhabdovirus, was recovered from cDNA in 1994 (Schnell et al. 1994). The approach involved intracellular expression of rabies virus N, P, and L protein, along with a full-length RNA whose correct 3' end was generated by the hepatitis delta virus (HDV) ribozyme. A transcript corresponding to the viral antigenome (positive strand) rather than to the genome (negative strand) was used to avoid an antisense problem raised by the presence of N, P, and L sequences in full-length RNAs. In this system, the essential helper proteins were provided by a replication-competent vaccinia vector encoding the phage T7 RNA polymerase to drive T7-specific transcription of plasmids encoding the required N, P and L proteins. Similar systems allowed recovery of infectious rabies viruses (Schnell et al. 1994; Ito et al. 2001), VSV (Lawson et al. 1995; Whelan et al. 1995), as well as the *Paramyxoviridae* Sendai virus (Garcin et al. 1995; Kato et al. 1996; Leyrer et al. 1998; Fujii et al. 2002), HP1V-3 (Hoffman and Banerjee 1997) and measles virus (Takeda et al. 2000; Fujii et al. 2002).

To avoid the use of replication-competent vaccinia, which requires that the rescued virus be separated from helper virus, several non-replicative helper viruses have been adapted to provide helper proteins to rescue non-segmented negative-strand RNA viruses. The highly attenuated modified vaccinia virus Ankara (MVA) expressing T7 RNA polymerase has been used for recovery of the Pneumovirus RSV (Collins et al. 1995), the Rubulavirus, SV5 (He et al. 1997), HPIV-3 (Durbin et al. 1997), rinderpest virus (Baron and Barrett 1997), and measles virus (Schneider et al. 1997), mumps virus (Clarke et al. 2000), CDV (Gassen et al. 2000), HPIV-2 (Kawano et al. 2001), and BPIV-3 (Schmidt et al. 2000). A recombinant fowlpox virus expressing the T7 RNA polymerase has been used for the recovery of the avian *Paramyxoviridae* NDV (Peeters et al. 1999) and of a chimeric rinderpest virus (Das et al. 2000).

To rescue *Mononegavirales* without contamination by any infectious or defective viral vector, cell lines expressing T3 or T7 RNA polymerase have been generated. In this case, in the absence of RNA-capping activity in the cytoplasm, protein expression was achieved using the IRES from encephalomyocarditis virus (EMCV) located upstream of the coding regions. A human embryo kidney cell line (293-3-46) expressing T7 RNA polymerase and measles virus proteins N and P was established to recover the Edmonston vaccine strain of measles virus (Radecke et al. 1995). The virus was rescued after transfection of plasmids specifying MV antigenomic RNA and L mRNA. It was shown that rescue efficiency in these cells, which was very low initially, was increased by heat shock treatment of the transfected cultures and additional cocultivation of transfected cells on Vero cells (Parks et al., 1999). Another cell line expressing T7 RNA polymerase (BSR T7/5) and based on baby hamster kidney cells (BHK) was used for recovery of BRSV (Buchholz et al. 2000), rabies viruses (Finke and Conzelmann 1999), VSV (Harty et al. 2001), NDV (Romer-Oberdorfer et al. 1999), and Ebola virus (Volchkov et al. 2001).

The inventors have used the 293-3-46 cell line to rescue the Schwarz vaccine MV vector (Combredet et al., 2003). However, they have experienced that, even using the heat shock method on transfected cells (Parks et al., 1999) and their cocultivation on Vero or CEF cells, the rescue was rather irreproducible and still at very low yield, or even impossible for some recombinants containing large additional sequences. This was due to the instability of helper cells since it was observed that the efficiency depends on the number of their passages. These cells have been generated by selecting geneticin-resistant clones of 293 cells transfected with pSC6-N, pSC6-P and pSC6-T7-NEO encoding respectively the MV N and P genes and the T7 RNA polymerase gene under control of the CMV promoter and a neomycin resistance gene (Radecke et al., 1995). The stability of their activity depends on their continuous selection under geneticin (G-418), and the removing of antibiotic during transfection and rescue experiments. During the illicit plasmid-based recombination of foreign DNA into chromosomic DNA, the concatemeres formed by plasmids are recombined and the geneticin selection maintains only the individual copies, which are very few. This might explain the reduction of efficiency observed with 293-3-46 cells after a few passages.

Therefore, there exists a need in the art for a new method for generating helper cell lines able to rescue, reproducibly and with high efficiency, recombinant, non-segmented negative-strand RNA viruses from cDNA, optionally modified, and without contamination by any other helper virus such as vaccinia virus.

BRIEF DESCRIPTION OF THE SEQUENCES

Figure 1A:
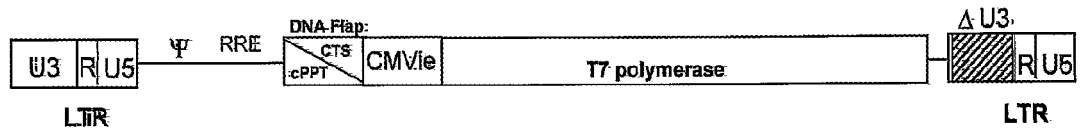
FIG. 1: schematic representation of the plasmids HIV-1-TRIPΔU3.CMV-T7 (A), HIV-1-TRIPΔU3.CMV-nlsT7 (B), HIV-1-TRIPΔU3.CMV-N (C) and HIV-1-TRIPΔU3.CMV-P (D). ψ: packaging psi motif: RRE: Rev-responsive element; cPPT: central polypurine tract, CTS: central termination sequence, CMVie: cytomegalovirus immediate-early promoter; ΔU3: deletion of parts of U3.
Figure 1B:
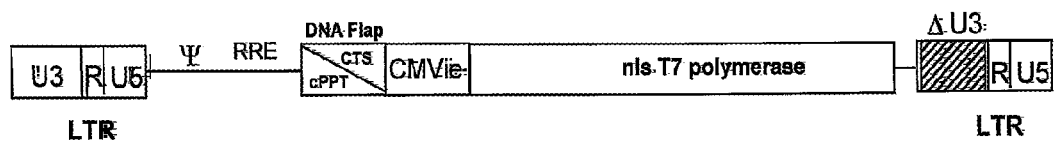
Figure 1C:
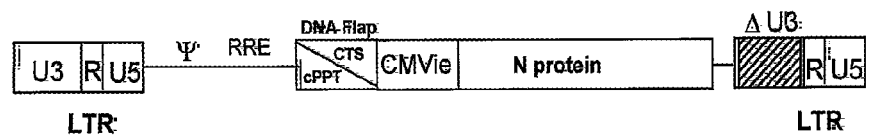
Figure 1D:
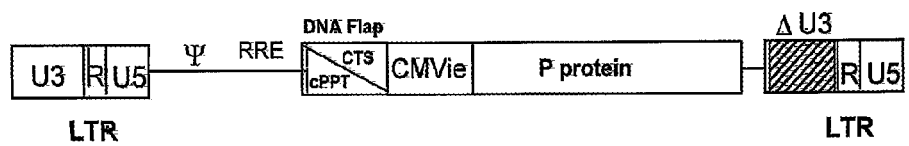

Nucleotide sequences of various retrovirus DNA FLAP are defined in different viruses: CAEV (SEQ ID NO:1), EIAV (SEQ ID NO:2), VISNA (SEQ ID NO:3), SIV AGM (SEQ ID NO:4), HIV-2 ROD (SEQ ID NO:5), HIV-1 LAI (SEQ ID NO:6) and HIV-1 (SEQ ID NO:7). The nucleotide sequences of the T7 RNA polymerase, the nls T7 RNA polymerase and the N, P and L proteins of the MV virus are defined respectively in SEQ ID NO: 8, 10, 12, 14 and 16, as well as their respective corresponding protein sequences in SEQ ID NO: 9, 11, 13, 15 and 17. The complete nucleotide sequence of the pTM-MVSchw plasmid (CNCM 1-2889) is defined in SEQ ID NO: 18. The complete nucleotide sequence of the pEMC-LSchw plasmid (CNCM 1-3881) is defined in SEQ ID NO: 19.

DETAILED DESCRIPTION

The present invention relates to a cell stably producing at least a RNA polymerase, a nucleoprotein (N) of a non-segmented negative-strand RNA virus and a phosphoprotein (P) of a non-segmented negative-strand RNA virus, or functional derivatives thereof. In a particular embodiment, the cell of the invention stably produces a RNA polymerase, a nucleoprotein (N) of a non-segmented negative-strand RNA virus and a phosphoprotein (P) of a non-segmented negative-strand RNA virus, or functional derivatives thereof.

The cells of the present invention are recombinant cells meaning that these cells are the results of in vitro purposive genetic manipulation resulting in recombination of genomic sequences of the cells with heterologous sequences, i.e., sequences originating from a different cell or organism. Starting from isolated cells, recombinant cells are prepared, have genetic and/or phenotypic features different from those of the starting cells, and also provide for the stable expression or production of at least a RNA polymerase, the N protein and the P protein of one or several non-segmented negative-strand RNA viruses. Cells of the invention are claimed as product, external to the body of a human being.

The expression "stably producing" means that cells express or produce at least the RNA polymerase, the N protein and the P protein over a number of cell divisions equals to or higher than about 65, advantageously as long as the cell survives. According to a particular embodiment of the invention, the recombinant cells express or produce the at least three proteins, i.e., at least the RNA polymerase, the N protein and the P protein, continually in time. According to a particular embodiment of the invention, the integrity, i.e., the primary amino acid sequence, of these three proteins is maintained, ensuring that the proteins expressed or produced are always the same.

The stable production of the RNA polymerase, the N protein and the P protein is independent of the presence in the cell, of plasmids) carrying the coding sequence of these proteins. Therefore, even though plasmids may be used at a particular step of the in vitro or ex vivo cell manipulation, the resulting recombinant cells, which stably produce the three or the at least three proteins, do not contain plasmids anymore. In that way, the expression is said plasmid-independent, in contrast to recombinant cells in which protein expression is driven by plasmid(s).

In a particular embodiment of the invention, the stable expression of the RNA polymerase, of the N protein and of the P protein, does not require the presence of a drug, such as an antibiotic, i.e., the stable expression does not require a selection pressure. Therefore, the stable production does not require the mandatory presence of plasmid(s) for survival, said plasmid bearing the coding sequence of the protein(s) to express.

Another feature of the invention is that each of the at least three proteins, i.e., at least the RNA polymerase, the N protein and the P proteins are produced or expressed at similar level over time. "Similar level" as used herein means that the expression of each of the three proteins is steady during the cell life, even after cell division, with a variation in expression level which is not more than about 30%, particularly not more than about 20% and preferably not more than about 10%, as compared to mean expression calculated at different times of the cell life.

The RNA polymerase expressed or produced by the cells of the invention is any polymerase suitable for synthesizing non-segmented negative-sense single-stranded viral RNA (vRNA) derived from a cDNA clone, in a rescue system. The nature of the polymerase depends essentially on the nature of the RNA promoter polymerase sequence located in the cDNA clone of the non-segmented negative-strand single-stranded RNA virus, used for the rescue system (also called reverse genetics, or de novo synthesis of negative-sense RNA viruses from cloned cDNA). As an example, the RNA polymerase is the T7 phage RNA polymerase, or its nuclear form (nlsT7).

The expressions "N protein" and "protein" refer respectively to the nucleoprotein (N) of a non-segmented negative-strand single-stranded RNA virus and the phosphoprotein (P) of a non-segmented negative-strand single-stranded RNA virus. Examples of families subfamilies, genius or species of non-segmented negative-strand single-stranded RNA viruses from which the N and/or P protein can be derived are listed in Table 1.

In a particular embodiment, the N and P proteins of a non-segmented negative-strand RNA virus are from the same virus, either from the same virus strain or from different virus strains. In another embodiment, the N and P proteins of a non-segmented negative-strand RNA virus are from different non-segmented negative-strand RNA virus.

TABLE 1

Family, subfamily, genus and species of several non-segmented negative-strand RNA viruses (NNV) of the order Mononegavirale.

| Family | Subfamily | Genus | Species | Abbreviation |
|---|---|---|---|---|
| Rhabdoviridae | / | Vesiculovirus | Vesicular stomatitis virus | VSV |
| | | Lyssavirus | Rabies virus | RV |
| Paramyxoviridae | Paramyxovirinae | Morbillivirus | Measles virus | MV |
| | | | Rinderpest virus | RPV |
| | | | Canine distemper virus | CDV |
| | | Respirovirus | Sendai virus | SeV |
| | | | Human parainfluenza virus type 3 | hPIV3 |
| | | | Bovine parainfluenza virus type 3 | bPIV3 |
| | | Rubulavirus | Simian virus type 5 | SV5 |
| | | | Mumps virus | |
| | | | Human parainfluenza virus type 2 | hPIV2 |
| | | | Newcastle disease virus | NDV |
| | Pneumovirinae | Pneumovirus | Human respiratory syncytial virus | hRSV |
| | | | Bovine respiratory syncytial virus | bRSV |
| Filoviridae | / | Ebola-like viruses | Ebola virus | / |

In particular embodiment, the N and P proteins are derived from a *Mononegavirus*, preferably a *Paramyxoviridae* virus, preferably a *Paramyxovirinae* virus, and most preferably a *Morbillivirus* virus. As an example of *Morbillivirus* is the *Measles virus* (MV), in particular an attenuated non immunosuppressive strain, e.g. an approved strain for a vaccine, and especially the Schwarz MV strain or the Edmonston (Ed) strain or a derivative from these strains. An approved strain for a vaccine is defined by the FDA (US Food and drug administration) as having the following provisions: safety, efficacy, quality and reproducibility, after rigorous reviews of laboratory and clinical data (www.fda.gov/cber/vaccine/vacappr.htm).

Each time reference is made in the present application, to non-segmented negative strand RNA virus, it possibly applies in particular to the specific viruses listed herein, and especially to a measles virus, in particular to the Schwarz strain.

The expression "functional derivatives thereof" refers to any functional variants including fragments of the RNA polymerase and/or the N protein and/or the P protein, provided that the functional derivatives keep the activity of the protein they are derived from, at least as a ribonucleoprotein complex (RNP complex), functional in transcription and replication in a virus genome, in a rescue system enabling the production of non-segmented negative-sense RNA viruses from cloned cDNA.

A functional variant is defined by a nucleic acid encoding said functional variant proteins, having at least one of the following features:

- the nucleic acid encoding the functional variant hybridizes in high stringency conditions with a nucleic acid encoding the wild-type (reference) RNA polymerase or with the N protein and the P protein of an identified non-segmented negative-strand RNA strain or virus. High stringency conditions are defined by Sambrook et al. in Molecular Cloning: a laboratory manual (1989). These conditions of high stringency encompass: use a prewashing solution for the nitrocellulose filters 5×SSC, 0.5% SDS, 1.0 mM EDTA (pH 8.0), hybridisation conditions of 50% formamide, 6×SSC at 42° C. and washing conditions at 68° C., 0.2×SSC and 0.1% SDS. Protocols are known to those having ordinary skill in the art. Moreover, the skilled artisan will recognize that the temperature and wash solution salt concentration can be adjusted as necessary according to experimental constraints;
- the nucleic acid encoding the functional variant presents at least 80%, preferably 90%, more preferably 95% or even 99% similarity with a native nucleic acid encoding the RNA polymerase, the N protein or the protein, said similarity being calculated over the entire length of both sequences;
- the nucleic acid encoding the functional variant differs from a native nucleic acid encoding the RNA polymerase, the N protein or the P protein by at least one nucleotide substitution, preferably 1, 2, 3, 4 or 5 substitution(s), optionally conservative substitutions (nucleotide substitution(s) not altering the amino acid sequence), by at least one nucleotide deletion or addition, preferably 1, 2, 3, 4 or 5 nucleotide(s) deletion or addition.

A fragment is defined in the present application as a part of the full-length RNA polymerase, of the N protein or of the P protein, as long as the fragment has the same activity as the entire protein from which it is derived, at least as a ribonucleoprotein complex (RNP complex) as disclosed herein. In a particular embodiment, the fragment represents at least 70%, particularly 80%, and more particularly 90% or even 95% of the full-length protein.

Accordingly, where reference is made herewith to RNA polymerase, N or P proteins or to their coding sequences, the description similarly applies to their functional derivatives as defined herein.

According to a particular embodiment a recombinant cell of the invention comprises, integrated in its genome, at least one copy of a nucleic acid encoding a RNA polymerase, at least one copy of a nucleic acid encoding a N protein of a non-segmented negative-strand RNA virus, and at least one copy of a nucleic acid encoding a P protein of a non-segmented negative-strand RNA virus. Optionally, the nucleic acids encoding the three proteins above are, each or at least one of these, under the control of transcription regulatory element(s) The expression "integrated in the genome" means that the at least one copy of a nucleic acid under the control of transcription regulatory element(s) is located within the genome of the recombinant cells, under conditions enabling said cells to stably express the protein encoded by the nucleic acid. In a particular embodiment, the recombinant cell of the invention comprises further, integrated in its genome, at least one copy of a nucleic acid encoding a L protein of a non-segmented negative-strand RNA virus.

"at least one copy" means that the nucleic acid encoding the RNA polymerase and/or the N protein and/or the P protein and/or the L protein may be present in one or several copies, preferably exactly or at least 2, 3, 4, 5, 6, 7, 8, 9, 10 copies, or more, depending on the expression level required for each of these proteins.

In a particular embodiment of the invention, the cells of the invention also contain at least one copy of a DNA flap integrated into the cell genome. A DNA flap is a nucleotide sequence of retroviral especially lentiviral, or retroviral-like origin comprising two essential regions, i.e., the cPPT (central polypurine tract) and the CTS (cis-acting termination region) regions, wherein the cPPT and CTS regions induce a three-stranded DNA structure during replication of DNA containing them (previously defined in Zennou et al., 2000; and in applications WO99/55892 and WO01/27300). In a particular embodiment, the DNA flap is inserted immediately upstream of the internal promoter enabling transcription of the nucleic acids encoding the RNA polymerase, the N protein, the P protein and possibly the L protein. The DNA flap (cPPT-CTS) is inserted into the retroviral-derived vectors of the invention in a functional orientation i.e., the cPPT region is in 5' with respect to the CTS region (the 5' part of the vector corresponding to the LTR containing the primer binding site (PBS), and the 3' part of the vector corresponding to the region containing the 3'PPT).

A DNA flap suitable for the invention may be obtained from a retrovirus especially from a lentivirus or retrovirus-like organism such as retrotransposon, prepared synthetically (chemical synthesis) or by amplification of the DNA flap from any retrovirus especially from a lentivirus nucleic acid such as by Polymerase chain reaction (PCR). The DNA flap may be obtained from a retrovirus, especially a lentivirus, especially a human retrovirus or lentivirus and in particular a HIV retrovirus, the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. In a more preferred embodiment, the DNA flap is obtained from an HIV retrovirus, for example HIV-1 or HIV-2 virus or any different isolate of these two types.

Preferred DNA flap comprises or consists in the sequences as defined in SEQ ID NO: 1 to 7. It is noteworthy that the DNA flap is used isolated from its natural (viral genome) nucleotide context i.e., isolated from the pol gene in which it is naturally contained in a lentivirus. Therefore, the DNA flap is used, in the present invention, deleted from the unnecessary 5' and 3' parts of the pol gene and is recombined with sequences of different origin. According to a particular embodiment, a DNA flap has a nucleotide sequence of about 90 to about 150 nucleotides, in particular from about 100 to about 140 nucleotides.

The invention also concerns a cell obtainable by recombination of its genome with (1) an expression vector comprising a DNA flap, and at least one copy of a nucleic acid encoding a RNA polymerase, (2) an expression vector comprising a DNA flap, and at least one copy of a nucleic acid encoding a N protein of a non-segmented negative-strand RNA virus, and (3) an expression vector comprising a DNA flap, and at least one copy of a nucleic acid encoding a P protein of a non-segmented negative-strand RNA virus. Definitions given above apply to these cells.

The invention is also directed to a cell obtainable by recombination of its genome with (1) an expression vector comprising a DNA flap, and at least one copy of a nucleic acid encoding a RNA polymerase, (2) an expression vector comprising a DNA flap, and at least one copy of a nucleic acid encoding a N protein of a non-segmented negative-strand RNA virus, (3) an expression vector comprising a DNA flap, and at least one copy of a nucleic acid encoding a P protein of a non-segmented negative-strand RNA virus and (4) an expression vector comprising a DNA flap, and at least one copy of a nucleic acid encoding a L protein of a non-segmented negative-strand RNA virus. Definitions given above apply to these cells. Definitions given above apply to these cells.

The invention encompasses a cell obtainable by recombination of its genome with an expression vector comprising at least one copy of a nucleic acid encoding a RNA polymerase, at least one copy of a nucleic acid encoding a N protein of a non-segmented negative-strand RNA virus, at least one copy of a nucleic acid encoding a P protein of a non-segmented negative-strand RNA virus and a DNA flap. Definitions given above apply to these cells. In a particular embodiment, the expression vector comprises further at least one copy of a nucleic acid encoding a L protein of a non-segmented negative-strand RNA virus.

The invention is also directed to an expression retroviral-derived vector comprising a DNA flap as described above and at least one nucleic acid encoding a protein necessary for the rescue of a non-segmented negative-strand RNA virus. In a particular vector of the invention, the nucleic acid encodes a protein that is selected from the group consisting of a RNA polymerase, a N protein of a non-segmented negative-strand RNA virus, a P protein of a non-segmented negative-strand RNA virus and a L protein of a non-segmented negative-strand RNA virus.

The term "genome" refers to any nucleic acid molecule, whose presence into the cell is not dependent upon pressure selection i.e., whose presence into the cell is permanent and/or does not depend from environmental conditions. The term "genome" does not encompass plasmids. Primarily, the term "genome" refers to nucleic acid molecules present into the cell nucleus (nuclear genome), by opposition to nucleic acid molecules present into the cytoplasm, and encompasses for example chromosomes. In particular embodiment, the term "genome" also includes nucleic acid molecules present in particular cell compartments, such as organelles, for example mitochondria (mitochondrial genome) or chloroplasts (chloroplast genome). In a particular embodiment, the genome is from a eukaryotic cell.

A retroviral-derived vector, and particularly a lentiviral-derived vector and more particular a HIV-1-derived vector, is a viral genome that comprises the elements necessary for the retrotranscription, particularly the LTRs possibly mutated including deleted in part especially deleted in the U3 region, as illustrated below and advantageously the DNA flap. These LTR and DNA flap regions may be the only sequences of retroviral, especially lentiviral origin in the retroviral-derived expression vector. In no case, the retroviral-derived vector contains the nucleotide sequences encoding the full-length retroviral proteins. In a particular embodiment of the invention, the retroviral-derived vector comprises or consists of a DNA flap and at least one nucleic acid encoding a protein necessary for the rescue of a non-segmented negative-strand RNA virus as described herein, as well as the LTRs of the corresponding viral genome.

An expression vector of the invention comprises a DNA flap and a nucleic acid encoding a RNA polymerase or functional part thereof. Such a vector may be the plasmid HIV-1-TRIPΔU3.CMV-T7 deposited with the CNCM on Dec. 14, 2006, under number 1-3702, which is an HIV-1 expression vector comprising a DNA flap (TRIP), a LTR deleted in the promoter and the enhancer of the U3 domain, a CMV promoter and a nucleic acid encoding the T7 phage RNA polymerase, especially one having the sequence SEQ ID NO: 8, or the plasmid HIV-1-TRIPΔU3.CMV-nlsT7 deposited with the CNCM on Dec. 14, 2006, under number I-3703, which is an HIV-1 expression vector comprising a DNA flap (TRIP), a LTR deleted in the promoter and the enhancer of the U3 domain, a CMV promoter and a nucleic acid encoding the nuclear form of the T7 phage RNA polymerase, especially one having the sequence SEQ ID NO: 10.

An expression vector of the invention comprises a DNA flap and a nucleic acid encoding a N protein of a non-segmented negative-strand RNA virus. Such a vector may be the plasmid HIV-1-TRIPΔU3.CMV-N deposited with the CNCM on Dec. 14, 2006, under number I-3700, which is an HIV-1 expression vector comprising a DNA flap (TRIP), a LTR deleted in the promoter and the enhancer of the U3 domain, a CMV promoter and a nucleic acid encoding the N protein of the MV Schwarz, especially one having the sequence SEQ ID NO: 12.

An expression vector of the invention comprises a DNA flap and a nucleic acid encoding a P protein of a non-segmented negative-strand RNA virus. Such a vector may be the plasmid HIV-1-TRIPΔU3.CMV-P deposited with the CNCM on Dec. 14, 2006, under number 1-3701, which is an HIV-1 expression vector comprising a DNA flap (TRIP), a LTR deleted in the promoter and the enhancer of the U3 domain, a CMV promoter and a nucleic acid encoding the P protein of the MV Schwarz, especially one having the sequence SEQ ID NO: 14.

Another expression vector of the invention comprises a nucleic acid encoding an L protein of a non-segmented negative-strand RNA virus. Such a vector may be the pEMC-LSchw plasmid, deposited with the CNCM on Dec. 18, 2007, under number 1-3881. One particular nucleic acid encoding an L protein is the one having SEQ ID NO:19.

The vectors CNCM 1-3700 to 3703 quoted above all are contained in *E. coli* (JM109) strain, cultivated in LB medium supplemented with ampicilin (100 μg/ml) at 37° C. with shaking.

The invention relates to each and any nucleotide fragment contained in the polynucleotides inserted in the deposited plasmids referred to herein, and especially to each and any region suitable to design the insert, according to the present disclosure. It relates also to the use of these fragments for the construction of plasmids of the invention.

The four plasmids above are examples of vectors that can be used in the recombination of cells to obtain recombinant cells of the invention. However, these examples do not constitute limitations of the invention; therefore, and as described above, the N and P proteins (or their functional derivatives) can be derived from any non-segmented negative-strand RNA virus, the T7 polymerase can be any RNA polymerase, the CMV promoter can be any promoter, the TRIP DNA flap can be any DNA flap and the HIV-1 expression vector can be any vector and particularly any viral vector.

Other expression vectors of the invention comprise a DNA flap and a nucleic acid encoding a L protein of a non-segmented negative-strand RNA virus, or comprise a DNA flap and nucleic acid(s) encoding a RNA polymerase, a N protein of a non-segmented negative-strand RNA virus, a P protein of a non-segmented negative-strand RNA virus and optionally a L protein of a non-segmented negative-strand RNA virus.

The term "expression vector" indicates that, besides the elements explicitly mentioned, the vector comprises all the elements necessary to drive the expression of the nucleic acid(s) encoding the proteins of interests (expression regulatory elements), and particularly transcription regulatory elements. "Transcription regulatory element" defines any DNA regions involved in the regulation of transcription of the nucleic acid(s) integrated in the genome, and encompasses a promoter, such as CMV, EF1alpha or mPGK (murine phosphoglycerate kinase) or more generally any promoter suitable for insertion in a retroviral, especially lentiviral vector, enhancer or cis-acting regulatory elements. These elements and particularly the promoter are chosen depending upon the nature of the recombinant cells. The determination of the suitable promoter, according to the expression level sought or to the recombined cell, makes part of the knowledge of the person skilled in the art. It is noteworthy that, when the recombinant cell contains several heterologous nucleic acids (also designated polynucleotides) encoding the proteins of interest, said transcription regulatory element(s) may be unique for all the nucleic acids or shared by some of them or in contrast each nucleic acid may be associated with a particular transcription regulatory element. In the latter case, the several transcription regulatory elements may be similar or different.

The presence of the DNA flap, in all the vectors used in the recombination step, leads to the formation of a DNA triplex structure (three stranded) at the DNA flap position (the triplex structure consisting of the region between the cPPT and the CTS domains including the CTS domain), enabling the import of the nucleic acid bearing the DNA flap into the nucleus of the cell (throughout nucleus membrane pore) and further the integration into the genome of this cell. The DNA flap acts as a cis-determinant of the vector nuclear import. In a first aspect, the presence of the DNA flap is of great interest for the recombination and the integration of nucleic acid(s) into non-dividing cells, since in the absence of cell division (and membrane disintegration), the import (and thus integration of nucleic acids into the cell genome) is only identified as a residual activity; therefore, the vectors containing the DNA flap are non-replicative retroviral vectors able to transduce non-dividing cells. In a second aspect, the presence of the DNA flap is also of great interest for the recombination and the integration of nucleic acid into dividing cells, by considerably improving the percentage of cells in which the nucleic acid containing the DNA flap is integrated. The insertion of the DNA flap sequence in an expression vector, as described in the present specification, strongly increases gene transfer in vitro and in vivo by stimulating nuclear import of vector DNA (Sirven et al, 2001; Zennou et al, 2001). HIV vectors including the DNA flap sequence (TRIP vectors) are able to transduce primary B and T cells, macrophages, dendritic cells, etc with a tenfold higher efficiency than other HIV vectors that lack the DNA flap. A transduction of 80-90% of cells can be routinely obtained.

Following the recombination by the vector(s) containing a DNA flap and nucleic acid(s) encoding the at least three proteins of interest and the integration of these nucleic acids in the genome, the recombinant cells stably produce the RNA polymerase, the N protein and the P protein.

The expression vectors of the invention, used to obtain the recombinant cells of the present invention, are viral vectors, and particularly viral expression vector, such as retroviral-derived, especially lentiviral-derived vectors such as HIV-, FIV- or SIV-derived vectors. More particularly, the lentiviral-derived vector is a human lentiviral-derived vector such as an HIV expression vector, particularly HIV-1 or HIV-2-derived vector. In a preferred embodiment, the viral vector is a HIV expression vector comprising a DNA flap as described above and at least one nucleic acid encoding the at least three proteins of interest. HIV vectors are classical replacement retroviral vectors in which substantially the entire coding viral sequences are replaced by the sequence to be transferred. HIV vectors express therefore only the heterologous nucleic acid(s) contained between the two HIV LTRs or mutated LTRs and under the control of the DNA flap. These vectors can thus accommodate large polynucleotides having up to 5-6 kb. A particular embodiment of the invention is a HIV expression virus as described above, and most particularly a HIV-1 expression vector, wherein a HIV-1 LTR is deleted for the promoter and the enhancer of the U3 domain (ΔU3). This particular deletion has been previously shown to increase the expression of the nucleic acid(s) contained in the vector, and particularly when associated with a promoter.

In a particular embodiment, the recombinant cell of the invention is obtainable by recombination of its genome either with plasmids HIV-1-TRIPΔU3.CMV-T7, HIV-1-TR1PAU3.CMV-N and HIV-1-TRIPΔU3.CMV-P, or with plasmids HIV-1-TRIPΔU3.CMV-nlsT7, HIV-1-TRIPΔU3.CMV-N and HIV-1-TRIPΔU3.CMV-P.

Cells of the invention can be prokaryotic or eukaryotic cells, particularly animal or plant cells, and more particularly mammalian cells such as human cells or non-human mammalian cells. In a particular embodiment, cells, before recombination of its genome, are isolated from either a primary culture or a cell line. Cells of the invention may be dividing or non-dividing cells. As an example of cells that can be recombined to provide the recombinant cells of the invention are HEK 293 (human embryonic kidney) cells, which cell line 293 is deposited with the ATCC under No. CRL-1573. In a particular embodiment, human cells are not germinal cells and/or embryonic stem cells.

Recombinant cells of the invention can be the 293-T7-NP cell line deposited with the CNCM (Paris, France) on Jun. 14, 2006, under number 1-3618 i.e., HEK-293 cells recombined with the plasmids HIV-1-TRIPΔU3.CMV-T7, HIV-1-TRIPΔU3.CMV-N and HIV-1-TRIPΔU3.CMV-P. Another example of recombinant cells of the invention are the 293-nlsT7-NP MV cell line deposited with the CNCM on Aug. 4, 2006, under number 1-3662 i.e., HEK-293 cells recombined with plasmids HIV-1-TRIPΔU3.CMV-nlsT7, HIV-1-TRIPΔU3.CMV-N and HIV-1-TRIPΔU3.CMV-P.

In a further embodiment of the invention, the recombinant cells of the invention are further recombined by an expression vector comprising a nucleic acid encoding a RNA polymerase large protein (L) of a non-segmented negative-strand RNA virus. The expression of the L protein may be temporary and driven by a plasmid not containing DNA flap, or in contrast be stable and driven by a vector containing a DNA flap as defined above. The recombination by a plasmid or vector bearing the at least one copy of the nucleic acid encoding the L protein may be simultaneous to or subsequent to the recombination by the vector(s) containing the coding sequence(s) of the RNA polymerase, the N protein and the P protein.

Therefore, the present invention also refers to a cell stably producing a RNA polymerase, a N protein of a non-segmented negative-strand RNA virus and a P protein of a non-segmented negative-strand RNA virus, or functional derivatives thereof, and producing, stably or not, a L protein of a non-segmented negative-strand RNA virus.

The L protein is derived from any non-segmented negative-strand RNA virus quoted in Table 1. In a particular embodiment, the L protein is from the same non-segmented negative-strand RNA virus as the N protein and/or the P protein, and particularly from the same virus strain. In another embodiment, the L protein is from a different non-segmented negative-strand RNA virus than the N protein and/or the P protein.

In particular embodiment, the L protein is from a *Paramyxoviridae* virus, preferably a *Paramyxovirinae* virus, and most preferably a *Morbillivirus* virus. As an example of *Morbillivirus* is the Measles virus (MV), in particular an attenuated non immunosuppressive strain, e.g. an approved strain for a vaccine, and especially the Schwarz MV strain, or even the Edmonston (Ed) strain. A particular L protein is the one of the MV virus (SEQ ID NO: 16) or the one encoded by the sequence inserted in pEMC-LSchw plasmid and especially the sequence found between nucleotides 1425 and 7976 of SEQ ID NO:19.

In a particular embodiment, the sequence of the L protein must not be modified with respect to the wild type L protein and must be functional i.e., enabling the production of particles or virus when transcomplemented with N and P proteins and a T7 polymerase in a host cell. A test to determine the effective functionality of a clone bearing the L protein is carried out by transfecting a competent cell with vector(s) encoding the N protein, the P protein and the T7 (or nlsT7) polymerase, a vector encoding the L protein to be tested, and a minigenome comprising a leader, a promoter, a reporter gene (such a GFP) and a trailer. The functionality of the L clone is revealed by the production of particles expressing the reporter gene.

The present invention also describes a cell according to the present specification further recombined with a non-segmented negative-strand cDNA clone of a non-segmented negative strand RNA virus i.e., the antigenomic RNA (+)

strand of the virus genome. "cDNA" used for the description of the nucleotide sequence of the molecule of the invention merely relates to the fact that originally said molecule is obtained by reverse transcription of the genomic (−) RNA genome of viral particles of a non-segmented negative strand RNA virus, particularly of the measles virus, and most preferably the full-length genomic (−) RNA genome of viral particles of a non-segmented negative strand RNA virus. This should not be regarded as a limitation for the methods used for the preparation of this cDNA clone. The invention thus encompasses, within the expression "cDNA", every DNA provided it has the above defined nucleotide sequence. Purified nucleic acids, including DNA, or plasmids are thus encompassed within the meaning cDNA according to the invention, provided said nucleic acid, especially DNA fulfils the above-given definitions.

In a particular embodiment, the cDNA clone of a non-segmented negative strand RNA virus contains, upstream of the viral sequences, transcription regulatory elements. In a preferred embodiment, these elements are the same as the one(s) located in the expression vector(s) comprising the N, P and/or L proteins described above. In a more preferred embodiment, the element is a T7 RNA polymerase promoter.

In an embodiment, the cDNA clone of a non-segmented negative-strand RNA virus is from the same non-segmented negative-strand RNA virus as the N protein and/or the P protein and/or the L protein, and particularly from the same virus strain. In another embodiment, the cDNA clone of a non-segmented negative strand RNA virus is from a different non-segmented negative-strand RNA virus than the N protein and/or the P protein and/or the L protein.

In particular embodiment, the cDNA clone is from a non-segmented negative strand RNA virus, such as a *Paramyxoviridae* virus, preferably a *Paramyxovirinae* virus, and most preferably a *Morbillivirus* virus. As an example of *Morbillivirus* is the Measles virus (MV), in particular an attenuated non immunosuppressive strain, e.g. an approved strain for a vaccine, and especially the Schwarz MV strain or the Edmonston (Ed) strain. Moreover, the nucleotide sequence of the non-segmented negative-strand cDNA clone may be modified as compared to the wild type strain or virus, such a defined below.

The invention also concerns cultures of cells wherein said cells are those defined throughout the specification, and particularly cultures of cells stably producing a RNA polymerase, a nucleoprotein (N) of a non-segmented negative-strand RNA virus and a phosphoprotein (P) of a non-segmented negative-strand RNA virus, or functional derivatives thereof. In another embodiment, the invention also concerns cultures of cells stably producing a RNA polymerase, a N protein of a non-segmented negative-strand RNA virus and a P protein of a non-segmented negative-strand RNA virus, or functional derivatives thereof, and producing, stably or transitory, a L protein of a non-segmented negative-strand RNA virus or functional derivatives thereof.

In an embodiment, the cells culture to be recombined is a primary culture i.e., a culture prepared from cells or tissues directly obtained from an animal (optionally non-human) or a plant. In another embodiment, the cells culture to be recombined is a cell line i.e., a population of cells resulting from the first subculture of a primary culture or from subsequent serial passaging of the cells.

In another aspect, the present invention also relates to various methods to produce infectious, recombinant, non-segmented negative-strand virus, using the cells of the invention.

A first method to produce infectious, recombinant, non-segmented negative-strand virus comprises or consists in:
  a. recombining a cell or a culture of cells stably producing a RNA polymerase, a nucleoprotein (N) of a non-segmented negative-strand RNA virus and a polymerase cofactor phosphoprotein (P) of a non-segmented negative-strand RNA virus, with cDNA clone of a non-segmented negative strand RNA virus and with a vector comprising a nucleic acid encoding a RNA polymerase large protein (L) of a non-segmented negative-strand RNA virus,
  b. transferring said recombinant cell or culture of recombinant cells onto cells competent to sustain the replication and production of non-segmented negative-strand RNA virus, and
  c. recovering the infectious, recombinant, non-segmented negative-strand RNA virus from the co-culture of step b.

A second method according to the invention is a method to produce infectious, recombinant, non-segmented negative-strand RNA virus comprising or consisting of:
  a. recombining a cell or a culture of cells stably producing a RNA polymerase, the nucleoprotein (N) of a non-segmented negative-strand RNA virus and the polymerase cofactor phosphoprotein (P) of a non-segmented negative-strand RNA virus, with a cDNA clone of a non-segmented negative strand RNA virus and with a vector comprising a nucleic acid encoding a RNA polymerase large protein (L) of a non-segmented negative-strand RNA virus, and
  b. recovering the infectious, recombinant, non-segmented negative-strand RNA virus from said recombinant cell or culture of recombinant cells.

As used herein, "recombining" means introducing at least one polynucleotide into a cell, for example under the form of a vector, said polynucleotide integrating (entirely or partially) or not integrating into the cell genome (such as defined above). According to a particular embodiment recombination can be obtained with a first polynucleotide which is a cDNA clone of a non-segmented negative strand RNA virus, whose definition, nature and optional modifications are discussed elsewhere in the present specification. Recombination can, also or alternatively, encompasses introducing a polynucleotide which is a vector encoding a RNA polymerase large protein (L) of a non-segmented negative-strand RNA virus, whose definition, nature and stability of expression has been described herein.

In these methods, the cell or a culture of cells stably producing a RNA polymerase, a nucleoprotein (N) of a non-segmented negative-strand RNA virus and a polymerase cofactor phosphoprotein (P) of a non-segmented negative-strand RNA virus is a cell as defined in the present specification or a culture of cells as defined in the present specification, i.e., are also recombinant cells to the extent that they have been modified by the introduction of one or more polynucleotides as defined above. In a particular embodiment of the invention, the cell or culture of cells, stably producing the RNA polymerase, the N and P proteins, does not produce the L protein of a non-segmented negative-strand RNA virus or does not stably produce the L protein of a non-segmented negative-strand RNA virus, e.g., enabling its transitory expression or production.

"Transfer" as used herein refers to the plating of the recombinant cells onto a different type of cells, and particularly onto monolayers of a different type of cells. These latter cells are competent to sustain both the replication and the production of infectious, recombinant, non-segmented negative-strand RNA viruses i.e., respectively the formation of infectious viruses inside the cell and possibly the release of these infectious viruses outside of the cells. This transfer results in the co-culture of the recombinant cells of the invention with competent cells as defined in the previous sentence. The above transfer may be an additional, i.e., optional, step when the recombinant cells are not efficient virus-producing culture i.e., that infectious viruses can not be efficiently recovered from these recombinant cells. This step is introduced after further recombination of the recombinant cells of the invention with a cDNA clone of a non-segmented negative-strand RNA virus, and optionally a vector comprising a nucleic acid encoding a RNA polymerase large protein (L) of a non-segmented negative-strand RNA virus.

In a particular embodiment of the invention, a transfer step is required since the recombinant cells, usually chosen for their capacity to be easily recombined are not efficient enough in the sustaining and production of recombinant infectious viruses. In said embodiment, the cell or culture of cells of step a. of the above-defined methods is a recombinant cell or culture of recombinant cells according to the invention, particularly recombinant HEK-293 cells such as the 293-T7-NP cell line deposited with the CNCM on Jun. 14, 2006, under number 1-3618 or 293-nlsT7-NP MV cell line deposited with the CNCM on Aug. 4, 2006, under number I-3662.

Cells competent to sustain the replication and production of non-segmented negative-strand RNA virus may be any cell type that can be co-cultivated with the recombinant cells of the invention but not necessarily cells of the same Kingdom, Phylum, Class, Order, Family, Genus or Species. Examples of competent cells are Vero (African green monkey kidney) cells or CEF (chick embryo fibroblast) cells. CEF cells can be prepared from fertilized chicken eggs as obtained from EARL Morizeau (8 rue Moulin, 28190 Dangers, France), from any other producer of fertilized chicken eggs or from MRC5 cells (ATCC CCL171; lung fibroblast).

In another embodiment of the invention, the transfer step is not needed and thus not carried out. This is one of the advantages of the present invention to provide a method to produce infectious, recombinant, non-segmented negative-strand RNA viruses that is easy to carry out, faster and cheaper than the conventional methods and enabling the recovery of recombinant infectious viruses free of contaminants. This can be achieved with the recombinant cells of the invention that have the features of:
  stably producing a RNA polymerase, a nucleoprotein (N) of a non-segmented negative-strand RNA virus and a phosphoprotein (P) of a non-segmented negative-strand RNA virus, and
  from which infectious recombinant viruses can be efficiently recovered, without contaminations by unwanted viruses and/or other type of cells.

The "Recovery of infectious recombinant virus" as used herein refers to any means by which the infectious viruses, previously produced by the cells, are released from the cells, and isolated from the cultured cells. The recovery is said to be "direct" when the infectious recombinant viruses are recovered from recombinant cells of the invention, without involvement of other cell type(s). In contrast, the recovery is said to be "indirect" when the infectious recombinant viruses are recovered via another cell type than the recombinant cells of the invention. As mentioned earlier, the present invention is the first to report the direct recovery of infectious, recombinant, non-segmented negative-strand RNA virus.

In particular methods of the invention, the recombining step does not comprise the steps of recombining a cell or a culture of cells stably producing a RNA polymerase, a nucleoprotein (N) of a non-segmented negative-strand RNA virus and a polymerase cofactor phosphoprotein (P) of a non-segmented negative-strand RNA virus, with a vector comprising a nucleic acid encoding a RNA polymerase large protein (L) of a non-segmented negative-strand RNA virus. In that case, the recombinant cells of the invention have been selected for their capacity to express the L protein and especially have been previously recombined with a vector comprising a nucleic acid encoding a RNA polymerase large protein (L), the nucleic acid encoding the L protein being integrated in the cell genome or not.

When appropriate vectors bearing accessory proteins (non-P, non-L or non-N proteins, or non-RNA polymerase) may optionally be used in the methods of the invention, particularly when a genome or a cDNA clone, deleted for these proteins, is used. Such accessory proteins are the C protein, the V protein, the NS1 protein, the NS2 protein, the M protein, the M2 protein and/or the SH proteins. The vector(s) bearing the coding sequences of these accessory proteins may optionally comprises a cDNA flap as defined above.

The stability of the production of the RNA polymerase, N protein and P protein in the recombinant cells of the invention leads to some advantages according to the methods previously described in the art:
  the method of the invention does not necessarily comprise a transfer step;
  the method does not comprise heat shock step as reported in Parks et al. (1999). Indeed, this step has been shown to improve the efficiency of the synthesis of viral N and P proteins, as well as RNA polymerase, which proteins are synthesized from nucleic acids borne on plasmids. In the present invention, however, the nucleic acids are integrated into the cell genome, and the expression of these proteins has been shown to be stable, and/or at a level appropriate to initiate the de novo encapsidation.
  the method produces large quantities of infectious viruses, since the production of the RNA polymerase, N protein and P protein is stable, and not dependent on their expression from plasmids. Therefore, about 100-400 out of $10^6$ recombined cells transmit infectious viruses after recombination (number of rescue events). This is mostly superior to the 1-6 out of $10^6$ transfected cells obtained with the method of Radecke et al. (1995). In a particular embodiment of the method, the number of rescue events, for $10^6$ recombined cells, is more than 20, more than 50, more than 100, more than 200, more than 300, more than 400 or more than 500.

Finally, another advantage of the invention is the large variety of cells that can be recombined, and used to perform the invention. Indeed, the recombinant cells can be any eukaryotic cell, particularly any mammalian cell, either non-human cell or human cell. In a particular embodiment, the recombinant cells of the invention are human fibroblasts, especially MRC5 cell line (human lung fibroblasts). The invention is particularly useful for cells that do not divide.

According to the invention, the cDNA clone of a non-segmented negative-strand of a RNA virus is from a MV virus, particularly an attenuated virus in particular an attenuated non immunosuppressive strain, e.g. an approved strain for a vaccine, such as the Schwarz MV strain. A cDNA clone is a DNA sequence encoding the full-length antigenome of a non-segmented negative-strand RNA virus.

In a particular embodiment of the invention, the N, P and L proteins as well as the cDNA clone are from the same virus, that can be any virus of Table I, particularly a MV virus as disclosed above such as the Schwarz MV strain of measles virus. The nucleotide sequences of the Edmonston B. strain and of the Schwarz strain have been disclosed in WO 98/13505. Independently of the nature of the N, P and L proteins and the cDNA clone of the non-segmented negative-strand RNA virus, the RNA polymerase is the T7 RNA polymerase. A particular cDNA sequence is the sequence of the cDNA of the Schwarz strain as defined in SEQ ID NO: 18. Such a cDNA can be obtained from pTM-MVSchw, that is a plasmid derived from Bluescript containing the complete sequence of the measles virus, vaccine strain Schwarz, under the control of the promoter of the T7 RNA polymerase. Its size is 18967 nt.

Alternatively, the cDNA clone of a non-segmented negative strand RNA virus is derived from any virus of Table I. A particular recombinant measles virus from which the cDNA clone is derived from is the Schwarz strain and especially an approved vaccine Schwarz strain such as that produced under the trademark Rouvax, available from Aventis Pasteur (France).

An "attenuated strain" is defined herein as a strain that is avirulent or less virulent than the parent strain in the same host, while maintaining immunogenicity and possibly adjuvanticity when administered in a host i.e., preserving immunodominant T and B cell epitopes and possibly the adjuvanticity such as the induction of T cell costimulatory proteins or the cytokine IL-12. In a particular embodiment, the attenuated strain is an "approved vaccine strain" i.e., a strain certified for use in vaccine production by one national or regional health authority having granted a marketing approval for this product (legal designation). Accordingly, an "approved vaccine strain" has been shown to be safe, stable and able to provide effective protection (immunogenicity and adjuvanticity). Stability of a strain is measured by assessing that the properties of the strain remain substantially unchanged after numerous passages on the same certified cell line.

"Derived from" as used herein means any cDNA clone whose nucleotide sequence is modified as compared to the one of the wild type virus or strain. This modification may be at least one substitution, deletion or insertion in the nucleotide sequence and particularly in the coding sequence of a protein of the virus or strain. In another embodiment, the nucleotide sequence is modified by the insertion of at least one heterologous nucleic acid(s) i.e., a sequence that is not naturally present in the virus or the strain in which the at least one nucleic acid(s) is inserted or a sequence which is not derived from the antigens of measles viruses. Moreover, the cDNA clone may be modified by deletion of part(s) of the wild-type viral genome, and insertion of heterologous nucleic acids.

In a preferred embodiment, it is pointed out that the derived cDNA clone, consisting or comprising one or several heterologous nucleic acid(s), meets the so-called rule of 6. Therefore, the derived cDNA clone is a polyhexameric length, i.e., is a multiple of six. This requirement is especially achieved for cDNA clones derived from *Paramyxoviridae*, and in particular measles viruses. Some non-segmented negative-strand RNA viruses do not comply with this rule, as known from the skilled person in the art.

Any heterologous nucleic acid can be inserted in the nucleotide sequence of the cDNA clone, as far as the insertion does not prevent the production of infectious recombinant non-segmented negative-strand virus (permissive sites). In a particular embodiment, the insertion or deletion of the native viral genome provides a polynucleotide which is a multiple of six. Therefore, even though the genome length is not a multiple of six, the modification consists of six or multiple of six deletions and/or insertions.

Therefore, the heterologous nucleic acid sequences may encode one or several peptides able to elicit a humoral and/or cellular immune response (such as CTL or CD4 response) in a determined host, against the organism or organisms especially the pathogenic organism(s), for example the virus, especially retrovirus, flavivirus or coronavirus, of the bacterium or parasites from which it (they) originate(s). Accordingly, the amino acid sequence of such peptide is one which comprises at least one epitope of an antigen, especially a conserved epitope, which epitope is exposed naturally on the antigen or is obtained or exposed as a result of a mutation or modification or combination of antigens. Heterologous nucleic acids, which can be inserted in the cDNA clones, encode especially structural antigens (including antigenic fragments thereof or derivatives of said antigens or fragments) of viruses including retroviruses such as human retroviruses especially lentivirus, in particular HIV-1 or HIV-2, flavivirus or coronavirus envelope, such as envelop or capsid antigen. Particularly, such antigens are especially from envelopes of AIDS viruses including HIV-1 or HIV-2, from capsid of HIV or from envelopes of the Yellow Fever Virus or envelopes from the West Nile Virus, or from envelopes of the Dengue virus (DV), envelopes of the Japanese encephalitis virus (JEV) or envelope of the SARS-associated coronavirus. Other retroviral, flaviviral or coronavirus antigens may however be advantageously used in order to derive recombinant measles viruses capable of eliciting antibodies against said retroviruses or flaviviruses, and/or capable of eliciting the production of neutralizing antibodies against the retrovirus or flaviviruses. In another embodiment, the peptide encoded or encompassed by the heterologous nucleic acid sequences is tumoral antigen or an antigen specifically expressed on the cell surface of cancer cells. According to another embodiment of the invention, the sequences encode multiepitopes or antigens that alternatively or additionally also elicit a cellular immune response against the retrovirus or flaviviruses.

Advantageously, the recombinant measles viruses produced by the method of the invention may also elicit a humoral and/or cellular immune response against measles virus. This response is however not mandatory provided the immune response against the epitope, or multiepitopes or antigens disclosed above is indeed obtained.

In a preferred embodiment of the invention, the heterologous nucleic acid encodes a protein from an HIV retrovirus, particularly an envelope antigen of HIV and especially a peptide derived from an envelope protein or glycoprotein of HIV-1 or HIV-2. The antigens of interest in this respect are especially gp160, gp120 and gp41 of HIV-1 or gp140, GAG or TAT of HIV-1. In a particular embodiment of the invention, the heterologous amino acid sequence is derived from a recombinant gp160, gp120 of HIV-1 or gp140, GAG or TAT of HIV-1.

In another embodiment, the V1, V2 and/or V3 loops of the gp120 (or gp160) antigen are deleted or deleted in part, individually or in combination in such a way that conserved epitopes are exposed on the obtained recombinant gp120 antigen. The V1, V2 and V3 loops of the gp120 (or gp160) antigen of HIV-1 have been especially disclosed in Fields virology (Fields B. N. et al. Lippincott Raven publishers 1996, p. 1953-1977).

In another embodiment, the heterologous nucleic acid encodes a peptide that is derived from the gp120 (or gp160) antigen of HIV-1, wherein the V1, V2 and/or V3 loops of the gp120 (or gp160) antigen are substituted or substituted in part, individually or in combination, in such a way that conserved epitopes are exposed on the obtained recombinant gp120 (or gp160) antigen.

In another embodiment, the heterologous nucleic acid encodes a peptide that is derived from an envelope antigen of HIV-1 especially is derived from the gp120 antigen in such a way that the V1 and V2 loops are deleted and the V3 loop is substituted for the sequence AAELDKWASAA.

In another embodiment, the heterologous nucleic acid encodes a peptide that is gp160ΔV3, gp160ΔV1V2, gp160ΔV1V2V3, gp140ΔV3, gp140ΔV1V2, gp140ΔV1V2V3.

Preferred cDNA clones containing epitopes from HIV, WNV, YFV, DV or JEV are vectors defined in Table II deposited at the CNCM (Collection Nationale de Culture de Microorganismes—Institut Pasteur—Paris, France), and whose features are given below.

I-2886 (pMV3(EdB)gp140[delta]V3HIV89.6P) is a plasmid derived from Bluescript containing the complete sequence of the measles virus (Edmonston strain B), under the control of the T7 RNA polymerase promoter and containing the gene of the gp140ΔV3(ELDKWAS) of the SVIH virus strain 89.6P inserted in an ATU at position 2 (between the N and P genes of measles virus). The size of the plasmid is 21058 nt.

I-2887 (pMV2(EdB)-NS1YFV17D) is a plasmid derived from Bluescript containing the complete sequence of the measles virus (Edmonston strain B), under the control of the T7 RNA polymerase promoter and containing the NS1 gene of the Yellow Fever virus (YFV 17D) inserted in an ATU at position 2 (between the N and P genes of measles virus). The size of the plasmid is 20163 nt.

I-2888 (pMV2(EdB)-EnvYFV17D) is a plasmid derived from Bluescript containing the complete sequence of the measles virus (Edmonston strain B), under the control of the T7 RNA polymerase promoter and containing the Env gene of the Yellow Fever virus (YFV 17D) inserted in an ATU at position 2 (between the N and P genes of measles virus). The size of the plasmid is 20505 nucleotides.

TABLE II

| Strain from which the sequence is derived from | Vector name | Deposit number | Date of deposit |
|---|---|---|---|
| Edmonston B. strain | pMV2(EdB)gp160[delta]V3HIV89.6P | CNCM I-2883 | Jun. 12, 2002 |
| | pMV2(EdB)gp160HIV89.6P | CNCM I-2884 | |
| | pMV2(EdB)gp140HIV89.6P | CNCM I-2885 | |
| | pMV3(EdB)gp140[delta]V3HIV89.6P | CNCM I-2886 | |
| | pMV2(EdB)-NS1YFV17D | CNCM I-2887 | |
| | pMV2(EdB)-EnvYFV17D | CNCM I-2888 | |
| Schwarz strain | pTM-MVSchw2-Es(WNV) | CNCM I-3033 | May 26, 2003 |
| | pTM-MVSchw2-GFPbis | CNCM I-3034 | |
| | pTM-MVSchw2-p17p24[delta]myr(HIVB) | CNCM I-3035 | |
| | pTM-MVSchw3-Tat(HIV89-6p) | CNCM I-3036 | |
| | pTM-MVSchw3-GFP | CNCM I-3037 | |
| | pTM-MVSchw2-Es (YFV) | CNCM I-3038 | |
| | pTM-MVSchw2-gp140 [delta] V1 V2 V3 (HIV89-6) | CNCM I-3054 | Jun. 19, 2003 |
| | pTM-MVSchw2-gp140 [delta] V3 (HIV89-6) | CNCM I-3055 | |
| | pTM-MVSchw2-gp160 [delta] V1 V2 V3 (HIV89-6) | CNCM I-3056 | |
| | pTM-MVSchw2-gp160 [delta] V1 V2 (HIV89-6) | CNCM I-3057 | |
| | pTM-MVSchw2-Gag SIV239 p17-p24 [delta] myr-3-gp140 (HIV89-6) | CNCM I-3058 | |
| | pTM-MVSchw2 [EDIII + M$^{1-40}$]WNV (IS-98-ST1) | CNCM I-3440 | May 26, 2005 |
| | pTM-MVSchw2 [EDIII + apoptoM]DV1 (FGA89) | CNCM I-3442 | |
| | pTM-MVSchw2 [EDIII] JEV (Nakayama) | CNCM I-3441 | |

I-2883 (pMV2(EdB)gp160[delta]V3HIV89.6P) is a plasmid derived from Bluescript containing the complete sequence of the measles virus (Edmonston strain B), under the control of the T7 RNA polymerase promoter and containing the gene of the gp160ΔV3+ELDKWAS of the virus SVIH strain 89.6P inserted in an ATU at position 2 (between the N and P genes of measles virus). The size of the plasmid is 21264 nt.

I-2884 (pMV2(EdB)gp160HIV89.6P) is a plasmid derived from Bluescript containing the complete sequence of the measles virus (Edmonston strain B), under the control of the T7 RNA polymerase promoter and containing the gene of the gp160 of the SVIH virus strain 89.6P inserted in an ATU at position 2 (between the N and P genes of measles virus). The size of the plasmid is 21658 nt.

I-2885 (pMV2(EdB)gp140HIV89.6P) is a plasmid derived from Bluescript containing the complete sequence of the measles virus (Edmonston strain B), under the control of the T7 RNA polymerase promoter and containing the gene of the gp140 of the SVIH virus strain 89.6P inserted in an ATU at position 2 (between the N and P genes of measles virus). The size of the plasmid is 21094 nt.

I-3033 (pTM-MVSchw2-Es(WNV)) is a plasmid derived from Bluescript containing a cDNA sequence of the complete infectious genome of the measles virus (Schwarz strain), under the control of the T7 RNA polymerase promoter and expressing the gene of the secreted envelope, (E) of the West Nile virus (WNV), inserted in an ATU.

I-3034 (pTM-MVSchw2-GFPbis) is a plasmid derived from Bluescript containing a cDNA sequence of the complete infectious genome of the measles virus (Schwarz strain), under the control of the T7 RNA polymerase promoter and expressing the gene of the GFP inserted in an ATU.

I-3035 (pTM-MVSchw2-p17p24[delta]myr(HIVB)) is a plasmid derived from Bluescript containing a cDNA sequence of the complete infectious genome of the measles virus (Schwarz strain), under the control of the T7 RNA polymerase promoter and expressing the gene of the gag gene encoding p17p24Amyrproteins of the HIVB virus inserted in an ATU.

I-3036 (pTMVSchw3-Tat(HIV89-6p)) is a plasmid derived from Bluescript containing a cDNA sequence of the complete infectious genome of the measles virus (Schwarz strain), under the control of the T7 RNA polymerase promoter and expressing the gene of the Tat gene of the virus strain 89.6P inserted in an ATU.

I-3037 (pTM-MVSchw3-GFP) is a plasmid derived from Bluescript containing a cDNA sequence of the complete infectious genome of the measles virus (Schwarz strain) under the control of the T7 RNA polymerase promoter and expressing the gene of the GFP gene inserted in an ATU having a deletion of one nucleotide.

I-3038 (pTM-MVSchw2-Es) (YFV) is a plasmid derived from Bluescript containing a cDNA sequence of the complete infectious genome of the measles virus (Schwarz strain) under the control of the T7 RNA polymerase promoter and expressing the gene of the secreted protein of the Fever virus (YFV) inserted in an ATU.

I-3054 (pTM-MVSchw2-gp140 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp140 [delta] V1 V2 (HIV 89-6) inserted in an ATU.

I-3055 (pTM-MVSchw2-gp140 [delta] V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp14 [delta] V3 (HIV 89-6) inserted in an ATU.

I-3056 (pTM-MVSchw2-gp160 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 V3 (HIV 89-6) inserted in an ATU.

I-3057 (pTM-MVSchw2-gp160 [delta] V1 V2 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 (HIV 89-6) inserted in an ATU.

I-3058 (pTM-MVSchw2-Gag SIV239 p17-p24 [delta] myr-3-gp140 (HIV89-6)) is a plasmid derived from Bluescript containing a cDNA sequence of the complete infectious genome of the measles virus (Schwarz strain), under the control of the T7 RNA polymerase promoter and expressing the gene encoding Gag SIV239 p17-p24 [delta] myr-3-gp140 (HIV89-6) inserted in an ATU.

I-3440 (pTM-MvSchw2-[EDIII+$M^{1-40}$] WNV (IS-98-ST1)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of the West Nile virus (WNV) (WNV IS-98-ST1) fused to the sequence 1-40 of the membrane protein M.

I-3442 (pTM-MvSchw2-[EDIII+ApoptoM] DV1 (FGA89)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of dengue-1 virus (strain FGA89) fused to the apoptotic sequence of the membrane protein M.

I-3441 (pTM-MvSchw2-[EDIII] JEV (Nakayama)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of the Japanese encephalitis virus (JEV), strain Nakayama.

In a particular embodiment, the heterologous nucleic acid encodes a peptide that is derived from an antigen of the Yellow Fever virus selected among the envelope (Env), the NS1 proteins or immunogenic mutants thereof. When the heterologous DNA sequence present in the recombinant measles virus vector of the invention is derived from the Yellow Fever Virus (YFV), it is advantageously selected among YFV 17D 204 commercialized by Aventis Pasteur under the trademark Stamaril®.

In another particular embodiment, the heterologous nucleic acid encodes a peptide that is derived from an antigen of the West Nile virus selected among the envelope (E), premembrane (preM) or immunogenic mutants thereof. When the heterologous DNA sequence present in the recombinant measles virus vector of the invention is derived from the West Nile Virus (WNV), it is advantageously selected among the neurovirulent strain IS 98-ST1.

The heterogeneous nucleic acid may encode a tumour-specific antigen (TSA) or a tumour-associated antigen (TAA).

Another advantage of the invention is the possibility to insert in the cDNA clone of a non-segmented negative-strand RNA virus, long heterologous nucleic acid or a large number of heterologous nucleic acids. Therefore, the cDNA clone may be modified by insertion of one or several heterologous nucleic acids whose total sequence is at least 5 kb.

The invention relates to each and any nucleotide fragment contained in the polynucleotides inserted in the deposited plasmids referred to herein, and especially to each and any region suitable to design the insert, according to the present disclosure. It relates also to the use of these fragments for the construction of plasmids of the invention.

The invention also relates to methods to produce recombinant cells stably expressing the three or at least the three following proteins, a RNA polymerase, a nucleoprotein (N) of a non-segmented negative-strand RNA virus and a phosphoprotein (P) of a non-segmented negative-strand RNA virus, or functional derivatives thereof, comprising or consisting in either:

a. recombining a cell with at least:
   an expression vector comprising a DNA flap, and at least one copy of a nucleic acid encoding a RNA polymerase,
   an expression vector comprising a DNA flap, and at least one copy of a nucleic acid encoding a N protein of a non-segmented negative-strand RNA virus, and
   an expression vector comprising a DNA flap, and at least one copy of a nucleic acid encoding a P protein of a non-segmented negative-strand RNA virus, and
b. selecting the cells that stably produce at least a RNA polymerase, a nucleoprotein (N) of a non-segmented negative-strand RNA virus and a phosphoprotein (P) of a non-segmented negative-strand RNA virus, or functional derivatives thereof.

or a. recombining a cell with at least an expression vector comprising:
   at least one copy of a nucleic acid encoding a RNA polymerase under the control of a promoter,
   at least one copy of a nucleic acid encoding a N protein of a non-segmented negative-strand RNA virus under the control of a promoter, a. at least one copy of a nucleic acid encoding a P protein of a non-segmented negative-strand RNA virus under the control of a promoter, and a DNA flap, and
b. selecting the cells that stably produce at least a RNA polymerase, a nucleoprotein (N) of a non-segmented negative-strand RNA virus and a phosphoprotein (P) of a non-segmented negative-strand RNA virus, or functional derivatives thereof.

In a particular embodiment of the invention, the method to produce recombinant cells comprises further recombining the recombinant cells obtained in the a. step of the method above with an expression vector comprising a nucleic acid encoding a RNA polymerase large protein (L) or a functional derivative thereof of a non-segmented negative-strand RNA virus and selecting the cells that stably produce at least a RNA polymerase, a nucleoprotein (N) of a non-segmented negative-strand RNA virus and a phosphoprotein (P) of a non-segmented negative-strand RNA virus, and that produce a large protein (L) of a non-segmented negative-strand RNA virus or functional derivatives thereof.

The present invention is also directed to the use of recombinant cells of the invention, as described in the present specification, as helper cells, especially as helper cells in the production of infectious, recombinant, non-segmented negative-strand RNA virus.

Further embodiments and characteristics of the invention defined are found in the following examples and figures.

EXAMPLES

The invention will be further described in the following examples, which do not limit the scope of the invention described in the claims.

Cells and Viruses

Vero (African green monkey kidney) cells were grown as monolayers in Dulbecco's modified Eagle's medium (DMEM) supplemented with 5% fetal calf serum (FCS). Human kidney 293 (HEK-293) cells were grown in DMEM supplemented with 10% FCS. Human diploid MRC5 cells were grown as monolayers in DMEM supplemented with 10% FCS. Chicken embryo fibroblastic cells (CEF) were prepared as follows: fertilized chicken eggs (Morizeau, Dangers, France) were incubated at 38° C. for 9 days. Embryos were collected under sterile conditions. Head, limbs and viscera were removed and embryos were chopped then trypsinized for 5-10 minutes at 37° C. (Trypsin/EDTA 2.5 g/L). After filtration (70 µm) and several washes in DMEM high glucose/10% FCS, cells were seeded (5-7 10$^6$ cells per Petri dish) and incubated overnight at 37° C. before use for virus infection.

Plasmid Constructions

To allow the easy recombination of additional sequences using the Gateway® recombination system (Invitrogen), the Gateway® cassette (attb1/attb2 Seq) was introduced by ligation into the HIV-1-TRIP-ΔU3-BSX plasmid vector (Zennou et al., 2000) linearized by SmaI digestion. The T7 RNA polymerase gene was amplified from pAR-1173 plasmid (Brookhaven National Laboratory, ref) by PCR using PfuTurbo DNA polymerase (Stratagene) and the following primers containing the Gateway® recombination sequences (underlined):

AttB1-T7Pol:
5'-GGGGACAAGTTTGTACAAAAAAGCAGGCTCCACCATGGAATTCTCT

GACATCGAACTGGCT-3'

AttB2-retourT7Pol:
5'-GGGGACCACTTTGTACAAGAAAGCTGGGTTATCACGCGAACGCGAA

GTCCGACTCTAAGATGTC-3'

A nuclear form of T7 RNA polymerase (nlsT7) was also amplified from pAR-3288 plasmid (Brookhaven National Laboratory, ref) using the following primers containing a nuclear localization signal (in bold) and the Gateway® recombination sequences (underlined):

AttB1-SV40nls:
5'-GGGGACAAGTTTGTACAAAAAAGCAGGCTCCACCATGGCACCAAAA

AAGAAGAGAAAGGTA-3'

AttB2-retourT7Pol:
5'-GGGGACCACTTTGTACAAGAAAGCTGGGTTATCACGCGAACGCGAA

GTCCGACTCTAAGATGTC-3'

Using the same approach, the Schwarz MV N and P genes were amplified by PCR from pTM-MVSchw plasmid, which contains a full-length infectious Schwarz MV antigenome (Combredet et al., 2003). The following primers containing the Gateway® recombination sequences (underlined) were used:

AttB1-N:
5'-GGGGACAAGTTTGTACAAAAAAGCAGGCTCCATGGCCACACTTTTA

AGGAGCTTAGCA-3'

AttB2-N:
5'-GGGACCACTTTGTACAAGAAAGCTGGGTGTGTACTAGTCTAGAAGA

TTTCTGTCATTGTA-3'

AttB1-P:
5'-GGGGACAAGTTTGTACAAAAAAGCAGGCTCCATGGCAGAAGAGCAG

GCACGCCAT-3'

AttB2-P:
5'-GGGGACCACTTTGTACAAGAAAGCTGGGTGTTACTACTTCATTATT

ATCTTCATCAGCATCTGGTGGA-3'

The different PCR fragments encoding the T7 RNA polymerase, the nlsT7 RNA polymerase and the MV N and P proteins were then introduced into the pDONR™207 entry plasmid (Invitrogen) and recombined in the modified HIV-1-TRIP-AU3-BSX plasmid using the Gateway® recombination system (Invitrogen). The different recombinant vector plasmids obtained (HIV-1-TRIP delta U3.CMV-T7, HIV-1-TRIP delta U3.CMV-nlsT7, HIV-1-TRIP delta U3.CMV-N and HIV-1-TRIP delta U3.CMV-P) were fully sequenced. These vectors were deposited with the CNCM on Dec. 14, 2006, under respectively number I-3702, I-3703, I-3700 and I-3701.

The plasmid pEMC-LSchw expressing the large polymerase (L) protein from Schwarz MV was constructed in a similar way as described in Radecke et al. (1995). The 6552 nucleotide long sequence of the Schwarz L gene was taken from pTM-MVSchw plasmid (Combredet et al., 2003) and inserted into the pEMC-La plasmid previously described in Radecke et al. (1995), using classical cloning procedures. This plasmid was deposited with the CNCM on Dec. 18, 2007 under number I-3881.

Production of Vector Particles

Vector particles have been produced by co-transfection of HEK-293 cells using calcium-phosphate procedure with either HIV-1-TRIP delta U3.CMV-T7, HIV-1-TRIP delta U3.CMV-nlsT7, HIV-1-TRIP delta U3.CMV-N, or HIV-1-TRIP delta U3.CMV-P vector plasmids, an encapsidation plasmid expressing HIV-1 gag and pol genes, and a plasmid expressing the VSV-G envelope glycoprotein (pHCMV-G) as described in (Zennou et al., 2000). The amount of Gag p24 antigen in stocks of vector particles concentrated by ultracentrifugation was determined using HIV-1 p24 ELISA (Perkin Elmer LifeSciences).

Generation of Cell Lines 293-T7-MV

Cells (HEK-293) were seeded into 35 mm wells one day before transduction by TRIP-T7 and TRIP-nlsT7 lentiviral vectors. Vectors (500 ng/ml p24) were added in DMEM supplemented with 10% FCS. During 8 days, the same amount of vector was repeatedly added every day on cells. Cells were expanded every two days. After each passage, the T7 RNA polymerase activity of the cells was determined. A 35 mm cell culture was transfected with 5 μg of pEMC-Luc using the calcium-phosphate procedure, and the luciferase activity in 1/20 of the cleared cell lysate harvested one day after transfection was measured in a luminometer. The luciferase activity increased after each additional transduction and remained maximal between the $7^{th}$ and the $8^{th}$ transduction. The absence of cytotoxicity of T7 RNA polymerase expression was demonstrated after each transduction by quantifying cell viability using the trypan blue-exclusion method and comparison to non-transduced cells. After 8 steps of transduction, two cell populations were generated with a very high T7 RNA polymerase activity, either cytoplasmic (293-T7) or nuclear (293-nlsT7).

Figure 2A:
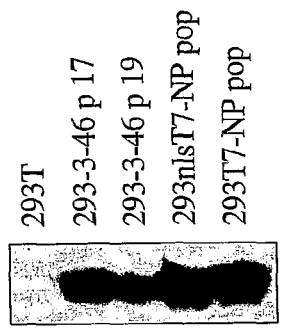
FIG. 2: Western blot showing the expression of the MV N and P proteins in different cell lysates; (A) non transduced 293T, previously described 293-3-46 cell line at two different passages (17 and 19), 293nlsT7-NP and 293T7-NP cell populations generated after transduction with lentiviral vectors; (B) MV-infected Vero cells, 293-3-46 cell line at two different passages (17 and 27), eight 293T7-NP cell clones; (C) MV-infected Vero cells, 293-3-46 cell line (passage 17), eight 293nlsT7-NP cell clones, uninfected Vero cells. Blots were probed with anti-MV NP antibody (1/500) and HRP anti-mouse Ig secondary antibody (1/1000).
Figure 2B:
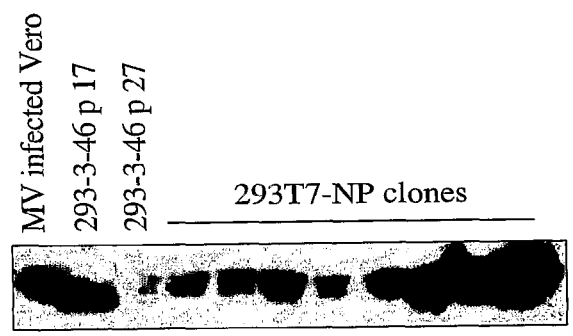
Figure 2C:
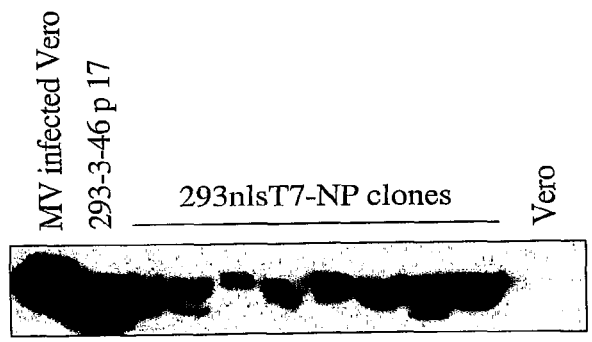

The two cell populations (293-T7 and 293-nlsT7) were then co transduced simultaneously by TRIP-N and TRIP-P vectors. Vectors (TRIP N: 390 ng/ml p24 and TRIP P: 330 ng/ml p24) were added on cells seeded in 35 mm wells. During 10 days, the same amount of both vectors was repeatedly added every day on cells. Cells were expanded every two days, After 10 rounds of transduction, the expression of MV N and P proteins was analyzed on the total cell populations by western blotting using 1/20 of the total lyzate of a 35 mm well. The expression of both proteins was comparable to that of similar number of infected Vero cells (FIG. 2). Transduced cells were then cloned by limiting dilution. Cells were seeded in 96-well plates at a dilution of 1/3 cell per well. After 2 weeks, the first clones were selected. About 100 clones of each 293-T7-NP and 293-nlsT7-NP cells were expanded to 24-well plates, then to 35 mm wells. The expression of MV N and P proteins was analyzed on 20 clones by western blotting using 1/20 of the total lyzate of a 35 mm well. The expression of both proteins was comparable to that of similar number of infected Vero cells (FIG. 2). The T7 RNA polymerase activity was measured for each clone as described above, A number of clones with a very high luciferase activity and a similar level of MV N and P expression were selected. The clones, listed below, were amplified and frozen at −180° C. in DMEM/30% FCS/10% DMSO at a density of $10^7$ cells/ml: 293-T7-NP1, 293-T7-NP3, 293-T7-NP5, 293-T7-NP7, 293-T7-NP8, 293-T7-NP10, 293-T7-NP13, 293-T7-NP14, 293-T7-NP20, 293-T7-NP28, 293-T7-NP31, 293-T7-NP33, 293-nlsT7-NP1, 293-nlsT7-NP5, 293-nlsT7-NP6, 293-nlsT7-NP13, 293-nlsT7-NP14, 293-nlsT7-NP15, 293-nlsT7-NP30 and 293-nlsT7-NP40.

Rescue of Schwarz MV Using 293-T7-NP and 293-nls T7-NP Helper Cells

To evaluate the capacity of the different helper 293-T7-NP and 293-nlsT7-NP cell clones generated to efficiently rescue MV from cDNA, we used the plasmid pTM-MVSchw-eGFP (Combredet et al., 2003) to rescue a recombinant Schwarz MV expressing the green fluorescent protein (eGFP). We used a similar system as described previously (Radecke et al., 1995; Parks et al., 1999; Combredet et al., 2003). Helper cells 293-T7-NP or 293-nlsT7-NP were transfected using the calcium phosphate procedure with pTM-MVSchw-eGFP (5 μg) and the plasmid pEMC-LSchw expressing the Schwarz MV polymerase (L) gene (20-100 ng). After overnight incubation at 37° C., the transfection medium was replaced by fresh medium and the cells were heat-shocked at 43° C. for 3 hours, then returned to 37° C. (22). After two days of incubation at 37° C., transfected cells were transferred onto monolayers of Vero, CEF or MRC5 cells and incubated at 37° C. in 10 cm dishes, except for CEF which were incubated at 32° C. Fluorescent cells appeared rapidly after 2-3 days of co culture on Vero, CEF or MRC5 cells. Infected cells expanded rapidly in focuses. The recombinant virus was highly syncytial in Vero cells and non-syncytial on CEF and MRC5 cells. Single syncytia or infectious focuses were transferred to 35 mm wells of Vero, CEF or MRC5 cells, then expanded to larger dishes by adding fresh cells. Virus was harvested from CEF or MRC5 cells after 5 days of infection, and from Vero cells when syncytia involved 80-90% of the culture (usually after 2 days) by scraping infected cells, freeze-thawing of cells and medium, and centrifugation to remove cellular debris. Such viral productions were titrated using the $TCID_{50}$ titration method. Briefly, Vero cells were seeded into 96-well plate (7500 cells/well) and infected by serial 1:10 dilutions of virus sample in DMEM/5% FCS. After incubation at 37° C. for 7 days, cells were stained with crystal violet and the virus dilution that resulted in infection in 50% of test unit was determined. The 50% end point described as tissue culture infectious dose ($TCID_{50}$) was calculated by the Kärber method (3). Recombinant virus rescued and grown on Vero cells had titers of $10^7$-$10^8$ $TCID_{50}$/ml, and virus rescued and grown on CEF or MRC5 cells had lower titers of $10^4$-$10^6$ $TCID_{50}$/ml.

The invention provides the technology for the construction and production of recombinant vectors, especially Human Immunodeficiency Virus (HIV)-TRIP lentiviral vectors, expressing the T7 RNA polymerase and measles Schwarz N and P proteins under the control of the cytomegalovirus (CMV) promoter. These vectors can be used to efficiently transduce in vitro at high level almost all cells, particularly human or mammalian cells. Such cells can be used as helper/transcomplementary cells able to generate de novo recombinant measles viruses after transfection by full-length infectious viral antigenomic cDNA or by modified cDNA clones as defined above.

The present invention allows rescuing any non-segmented negative-strand RNA viruses, such as measles viruses, from cDNA, optionally modified, without contamination by any other helper virus such as vaccinia virus, Due to the high transduction efficiency of lentiviral vectors, this method allows to generate cells expressing a very high level of helper proteins. Because retrovirus-based recombination, particularly lentiviral-based recombination, of foreign DNA into chromosomic DNA is genuine as compared to the illicit plasmid-based recombination, the helper cells generated by this method are very stable and their high efficiency to rescue non-segmented negative-strand RNA viruses from cDNA is maintained after multiple serial passages.

BIBLIOGRAPHY

Arneborn, P., G. Biberfeld, M. Forsgren, and L. V. von Stedingk. 1983. Specific and non-specific B cell activation in measles and varicella. Clin Exp Immunol 51:165-72.

Baron, M. D., and T. Barrett. 199T Rescue of rinderpest virus from cloned cDNA. J Virol 71:1265-71.

Buchholz, U. J., H. Granzow, K. Schuldt, S. S. Whitehead, B. R. Murphy, and P. L. Collins. 2000. Chimeric bovine respiratory syncytial virus with glycoprotein gene substitutions from human respiratory syncytial virus (HRSV): effects on host range and evaluation as a live-attenuated HRSV vaccine. J Virol 74:1187-99.

C.D.C. 2005. Progress in reducing measles mortality—worldwide, 1999-2003. MMWR Morb Mortal Wkly Rep. 54:200-203.

Calain, P., and L. Roux. 1993. The rule of six, a basic feature for efficient replication of Sendai virus defective interfering RNA. J Virol 67:4822-30.

Clarke, D. K., M. S. Sidhu, J. E. Johnson, and S. A. Udem. 2000. Rescue of mumps virus from cDNA. J Virol 74:4831-8.

Collins, P. L., M. G. Hill, E. Camargo, H. Grosfeld, R. M. Chanock, and B. R. Murphy. 1995. Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci USA 92:11563-7.

Combredet, C., V. Labrousse-Najburg, L. Mollet, C. Lorin, F. Delebecque, B. Hurtrel, H. McClure, M. Feinberg, M. Brahic, and F. Tangy. 2003. A molecularly cloned Schwarz strain of measles virus vaccine induces strong immune responses in macaques and transgenic mice. Journal of Virology 77:11546-11554.

Das, S.C., M. D. Baron, and T. Barrett. 2000. Recovery and characterization of a chimeric rinderpest virus with the glycoproteins of peste-des-petits-ruminants virus: homologous F and H proteins are required for virus viability. J Virol 74:9039-47.

Durbin, A. P., S. L. Hall, J. W. Siew, S. S. Whitehead, P. L. Collins, and B. R. Murphy. 1997. Recovery of infectious human parainfluenza virus type 3 from cDNA. Virology 235:323-32.

Enders, J. F., and T. C. Peebles. 1954. Propagation in tissue cultures od cytopathogenic agents from patients with measles. Proc. Soc. Exp. Biol. Med. 86:277-286.

Finke, S., and K. K. Conzelmann. 1999. Virus promoters determine interference by defective RNAs: selective amplification of mini-RNA vectors and rescue from cDNA by a 3' copy-back ambisense rabies virus. J Virol 73:3818-25.

Fujii, Y., T. Sakaguchi, K. Kiyotani, C. Huang, N. Fukuhara, Y. Egi, and T. Yoshida. 2002. Involvement of the leader sequence in Sendai virus pathogenesis revealed by recovery of a pathogenic field isolate from cDNA. Virol 76:8540-7.

Garcin, D., P. Latorre, and D. Kolakofsky. 1999. Sendai virus C proteins counteract the interferon-mediated induction of an antiviral state. J Virol 73:6559-65.

Gassen, U., F. M. Collins, W. P. Duprex, and B. K. Rima. 2000. Establishment of a rescue system for canine distemper virus. J Virol 74:10737-44.

Griffin, D. 2001. Measles virus, p. 1401-1441. In D. Knipe and P. Howley (ed.), Field's Virology, 4th Edition, vol. 2. Lippincott—Raven Publishers, Philadelphia.

Harty, R. N., M. E. Brown, F. P. Hayes, N. T. Wright, and M. J. Schnell. 2001. Vaccinia virus-free recovery of vesicular stomatitis virus. J Mol Microbiol Biotechnol 3:513-7.

He, B., R. G. Paterson, C. D. Ward, and R. A. Lamb. 1997. Recovery of infectious SV5 from cloned DNA and expression of a foreign gene. Virology 237:249-60.

Hilleman, M. 2002. Current overview of the pathogenesis and prophylaxis of measles with focus on practical implications. Vaccine 20:651-665.

Hoffman, M. A., and A. K. Banerjee. 1997. An infectious clone of human parainfluenza virus type 3. J Virol 71:4272-7.

Ito, N., M. Takayama, K. Yamada, M. Sugiyama, and N. Minamoto. 2001. Rescue of rabies virus from cloned cDNA and identification of the pathogenicity-related gene: glycoprotein gene is associated with virulence for adult mice. J Virol 75:9121-8.

Kato, A., Y. Sakai, T. Shioda, T. Kondo, M. Nakanishi, and Y. Nagai. 1996. Initiation of Sendai virus multiplication from transfected cDNA or RNA with negative or positive sense. Genes Cells 1:569-79.

Kawano, M., M. Kaito, Y. Kozuka, H. Komada, N. Noda, K. Nanba, M. Tsurudome, M. Ito, M. Nishio, and Y. Ito. 2001. Recovery of infectious human parainfluenza type 2 virus from cDNA clones and properties of the defective virus without V-specific cysteine-rich domain. Virology 284:99-112.

Kim, E. A., K. S. Lee, S. L. Primack, H. K. Yoon, H. S. Byun, T. S. Kim, G. Y. Suh, O. J. Kwon, and J. Han. 2002. Viral pneumonias in adults: radiologic and pathologic findings. Radiographics 22 Spec No:S137-49.

Lawson, N. D., E. A. Stillman, M. A. Whitt, and J. K. Rose. 1995. Recombinant vesicular stomatitis viruses from DNA. Proc Natl Acad Sci USA 92:4477-81.

Leyrer, S., W. J. Neubert, and R. Sedlmeier. 1998. Rapid and efficient recovery of Sendai virus from cDNA: factors influencing recombinant virus rescue. J Virol Methods 75:47-58.

Okada, H., F. Kobune, T. A. Sato, T. Kohama, Y. Takeuchi, T. Abe, N. Takayama, T. Tsuchiya, and M. Tashiro. 2000. Extensive lymphopenia due to apoptosis of uninfected lymphocytes in acute measles patients. Arch Virol 145:905-20.

Okada, H., T. A. Sato, A. Katayama, K. Higuchi, K. Shichijo, T. Tsuchiya, N. Takayama, Y. Takeuchi, T. Abe, N. Okabe, and M. Tashiro. 2001. Comparative analysis of host responses related to immunosuppression between measles patients and vaccine recipients with live attenuated measles vaccines. Arch Virol 146:859-74.

Ovsyannikova, I., N. Dhiman, R. Jacobson, R. Vierkant, and G. Poland. 2003. Frequency of measles virus-specific CD4+ and CD8+ T cells in subjects seronegative or highly seropositive for measles vaccine. Clinical and Diagnostic Laboratory Immunology 10:411-416.

Parks, C. L, R. A. Lerch, P. Walpita, M. S. Sidhu, and S. A. Udem. 1999. Enhanced measles virus cDNA rescue and gene expression after heat shock. J Virol 73:3560-6.

Parks, C. L., R. A. Lerch, P. Walpita, H. P. Wang, M. S. Sidhu, and S. A. Udem. 2001a. Analysis of the noncoding regions of measles virus strains in the Edmonston vaccine lineage. J Virol 75:921-33.

Parks, C. L., R. A. Lerch, P. Walpita, H. P. Wang, M. S. Sidhu, and S. A. Udem. 2001b. Comparison of predicted amino acid sequences of measles virus strains in the Edmonston vaccine lineage. J Virol 75:910-20.

Peeters, B. P., O. S. de Leeuw, G. Koch, and A. L. Gielkens. 1999. Rescue of Newcastle disease virus from cloned cDNA: evidence that cleavability of the fusion protein is a major determinant for virulence. J Virol 73:5001-9.

Radecke, F., P. Spielhofer, H. Schneider, K. Kaelin, M. Huber, C. Dotsch, G. Christiansen, and M. A. Billeter. 1995. Rescue of measles viruses from cloned DNA. Embo J 14:5773-84.

Romer-Oberdorfer, A., E. Mundt, T. Mebatsion, U. J. Buchholz, and T. C. Mettenleiter. 1999. Generation of recombinant lentogenic Newcastle disease virus from cDNA. J Gen Virol 80 (Pt 11):2987-95.

Schmidt, A. C., J. M. McAuliffe, A. Huang, S. R. Surman, J. E. Bailly, W. R. Elkins, P. L. Collins, B. R. Murphy, and M. H. Skiadopoulos. 2000. Bovine parainfluenza virus type 3 (BPIV3) fusion and hemagglutinin-neuraminidase glycoproteins make an important contribution to the restricted replication of BPIV3 in primates. J Virol 74:8922-9.

Schneider, H., P. Spielhofer, K. Kaelin, C. Dotsch, F. Radecke, G. Sutter, and M. A. Billeter. 1997. Rescue of measles virus using a replication-deficient vaccinia-T7 vector. J Virol Methods 64:57-64.

Schnell, M. J., L. Buonocore, E. Kretzschmar, E. Johnson, and J. K. Rose. 1996. Foreign glycoproteins expressed from recombinant vesicular stomatitis viruses are incorporated efficiently into virus particles. Proc Natl Acad Sci USA 93:11359-65.

Schnell, M. J., T. Mebatsion, and K. K. Conzelmann. 1994. Infectious rabies viruses from cloned cDNA. Embo J 13:4195-203.

Schwarz, A. 1962. Preliminary tests of a highly attenuated measles vaccine. Am. J. Dis. Child. 103:216-219.

Sirven, A., E. Ravet, P. Charneau, V. Zennou, L. Coulombel, D. Guetard, F. Pflumio, and A. Dubart-Kupperschmitt. 2001. Enhanced transgene expression in cord blood CD34 (+)-derived hematopoietic cells, including developing T cells and NOD/SCID mouse repopulating cells, following transduction with modified trip lentiviral vectors. Mol Ther 3:438-48.

Takeda, M., K. Takeuchi, N. Miyajima, F. Kobune, Y. Ami, N. Nagata, Y. Suzaki, Y. Nagai, and M. Tashiro. 2000. Recovery of pathogenic measles virus from cloned cDNA. J Virol 74:6643-7.

Volchkov, V. E., V. A. Volchkova, E. Muhlberger, L. V. Kolesnikova, M. Weik, O. Dolnik, and H. D. Klenk. 2001. Recovery of infectious Ebola virus from complementary DNA: RNA editing of the GP gene and viral cytotoxicity. Science 291:1965-9.

Whelan, S. P., L. A. Ball, J. N. Barr, and G. T. Wertz. 1995. Efficient recovery of infectious vesicular stomatitis virus entirely from cDNA clones. Proc Natl Acad Sci USA 92:8388-92.

Zennou, V., C. Petit, D. Guetard, U. Nerhbass, L. Montagnier, and P. Charneau. 2000. HIV-1 genome nuclear import is mediated by a central DNA flap. Cell 101:173-85.

Zennou, V., C. Serguera, C. Sarkis, P. Colin, E. Perret, J. Mallet, and P. Charneau. 2001. The HIV-1 DNA flap stimulates HIV vector-mediated cell transduction in the brain. Nat Biotechnol 19:446-50.

The invention claimed is:

1. A method to produce an infectious non-segmented negative-strand RNA virus, comprising:
   a) providing a cell line comprising:
      i) a stably integrated retroviral vector comprising a coding sequence for an RNA polymerase;
      ii) a stably integrated retroviral vector comprising a coding sequence for a nucleoprotein (N) of a non-segmented negative-strand RNA virus; and
      iii) a stably integrated retroviral vector comprising a coding sequence for a polymerase cofactor phosphoprotein (P) of a non-segmented negative-strand RNA virus;
      wherein the cell line stably expresses the RNA polymerase, N and P proteins;
   b) transfecting the cell line of a) with (i) a vector comprising the coding sequence for a RNA polymerase large protein (L) of a non-segmented negative-strand RNA virus, and (ii) a vector comprising a cDNA clone of a non-segmented negative-strand RNA virus;
   c) combining transfected cells of b) with cells competent to sustain the replication and production of the non-segmented negative-strand RNA virus to form a co-culture; and
   d) recovering the infectious non-segmented negative-strand RNA virus from the co-culture;
   wherein the method does not comprise continuous selection.

2. The method of claim 1, wherein the N, P, and L proteins are from the same type of non-segmented negative-strand RNA virus.

3. The method of claim 1, wherein the N, P, and L proteins are from a measles virus.

4. The method of claim 3, wherein the measles virus is a Schwarz strain measles virus.

5. The method of claim 1, wherein the cDNA clone of a non-segmented negative-strand RNA virus is a cDNA clone of a measles virus.

6. The method of claim 5, wherein the measles virus is a Schwarz strain measles virus.

7. The method of claim 3, wherein the cDNA clone of a non-segmented negative-strand RNA virus is a cDNA clone of a measles virus.

8. The method of claim 7, wherein the measles virus is a Schwarz strain measles virus.

9. The method of claim 1, wherein the competent cells in c) are Vero (African green monkey kidney) cells, CEF (chick embryo fibroblast) cells or MRC5 cells.

10. The method according to claim 1, wherein the nucleotide sequence of the cDNA clone of the measles virus is modified by insertion, at a permissive site, of at least one heterologous nucleic acid.

11. The method according to claim 10, wherein the at least one heterologous nucleic acid encodes at least one epitope.

12. A method to produce an infectious non-segmented negative-strand RNA virus, comprising:
   a) providing a cell line comprising:
      i) a stably integrated retroviral vector comprising a coding sequence for an RNA polymerase;
      ii) a stably integrated retroviral vector comprising a coding sequence for a nucleoprotein (N) of a non-segmented negative-strand RNA virus;
      iii) a stably integrated retroviral vector comprising a coding sequence for a polymerase cofactor phosphoprotein (P) of a non-segmented negative-strand RNA virus; and
      iv) a stably integrated retroviral vector comprising a coding sequence for an RNA polymerase large protein (L) of a non-segmented negative-strand RNA virus;
      wherein the cell line stably expresses the RNA polymerase, N, P and L proteins;
   b) transfecting the cell line of a) with a vector comprising a cDNA clone of a non-segmented negative-strand RNA virus;
   c) combining transfected cells of b) with cells competent to sustain the replication and production of the non-segmented negative-strand RNA virus to form a co-culture; and
   d) recovering the infectious non-segmented negative-strand RNA virus from the co-culture;
   wherein the method does not comprise continuous selection.

13. The method of claim 12, wherein the N, P, and L proteins are from the same type of non-segmented negative-strand RNA virus.

14. The method of claim 12, wherein the N, P, and L proteins are from a measles virus.

15. The method of claim 14, wherein the measles virus is a Schwarz strain measles virus.

16. The method of claim 12, wherein the cDNA clone of a non-segmented negative-strand RNA virus is a cDNA clone of a measles virus.

17. The method of claim 16, wherein the measles virus is a Schwarz strain measles virus.

18. The method of claim 14, wherein the cDNA clone of a non-segmented negative-strand RNA virus is a cDNA clone of a measles virus.

19. The method of claim 18, wherein the measles virus is a Schwarz strain measles virus.

20. The method of claim 12, wherein the competent cells in c) are Vero (African green monkey kidney) cells, CEF (chick embryo fibroblast) cells or MRC5 cells.

21. The method according to claim 12, wherein the nucleotide sequence of the cDNA clone of the measles virus is modified by insertion, at a permissive site, of at least one heterologous nucleic acid.

22. The method according to claim 21, wherein the at least one heterologous nucleic acid encodes at least one epitope.

* * * * *

SEQUENCE LISTING

```
<160> NUMBER OF SEQ ID NOS: 26

<210> SEQ ID NO 1
<211> LENGTH: 200
<212> TYPE: DNA
<213> ORGANISM: Artificial
<220> FEATURE:
<223> OTHER INFORMATION: CAEV FLAP

<400> SEQUENCE: 1
gttccagcca caatttgtcg ctgtagaatc agccatagca gcagccctag tcgccataaa      60
tataaaaaga aagggtgggc tggggacaag ccctatggat atttttatat ataataaaga     120
acagaaaaga ataaataata aatataataa aaattctcaa aaaattcaat tctgttatta     180
cagaataagg aaaagaggac                                                 200

<210> SEQ ID NO 2
<211> LENGTH: 200
<212> TYPE: DNA
<213> ORGANISM: Artificial
<220> FEATURE:
<223> OTHER INFORMATION: EIAV FLAP

<400> SEQUENCE: 2
cttgtaacaa agggagggaa agtatgggag gacagacacc atgggaagta tttatcacta      60
atcaagcaca agtaatacat gagaaacttt tactacagca agcacaatcc tccaaaaaat     120
tttgttttta caaaatccct ggtgaacatg attggaaggg acctactagg gtgctgtgga     180
agggtgatgg tgcagtagta                                                 200
```

-continued

<210> SEQ ID NO 3
<211> LENGTH: 200
<212> TYPE: DNA
<213> ORGANISM: Artificial
<220> FEATURE:
<223> OTHER INFORMATION: VISNA FLAP

<400> SEQUENCE: 3

```
ggaccctcat tactctaaat ataaaaagaa agggtgggct agggacaagc cctatggata        60
tatttatatt taataaggaa caacaaagaa tacagcaaca agtaaatca aaacaagaaa       120 aaattcgatt ttgttattac agaacaagaa aagagggca tccaggagag tggcaaggac       180
caacacaggt actttggggc                                                  200
```

<210> SEQ ID NO 4
<211> LENGTH: 200
<212> TYPE: DNA
<213> ORGANISM: Artificial
<220> FEATURE:
<223> OTHER INFORMATION: SIV AGM FLAP

<400> SEQUENCE: 4

```
tactgatggc ttgcatactt cacaattta aagaaaggg aggaataggg ggacagactt        60
cagcagagag actaattaat ataataacaa cacaattaga aatacaacat ttacaaacca      120
aaattcaaaa aattttaaat tttagagtct actacagaga agggagagac cctgtgtgga      180
aaggaccggc acaattaatc                                                  200
```

<210> SEQ ID NO 5
<211> LENGTH: 200
<212> TYPE: DNA
<213> ORGANISM: Artificial
<220> FEATURE:
<223> OTHER INFORMATION: HIV-2 ROD FLAP

<400> SEQUENCE: 5

```
tgcatgaatt ttaaaagaag ggggggaata ggggatatga ctccatcaga aagattaatc       60
aatatgatca ccacagaaca agagatacaa ttcctccaag ccaaaaattc aaattaaaa      120 gattttcggg tctatttcag agaaggcaga gatcagttgt ggaaaggacc tggggaacta      180
ctgtggaaag gagaaggagc                                                  200
```

<210> SEQ ID NO 6
<211> LENGTH: 200
<212> TYPE: DNA
<213> ORGANISM: Artificial
<220> FEATURE:
<223> OTHER INFORMATION: HIV-1 LAI FLAP

<400> SEQUENCE: 6

```
cagtattcat ccacaatttt aaaagaaaag gggggattgg ggggtacagt gcagggaaa        60 gaatagtaga cataatagca acagacatac aaactaaaga attacaaaaa caaattacaa      120
aaattcaaaa ttttcgggtt tattacaggg acagcagaga tccactttgg aaaggaccag      180
caaagctcct ctggaaaggt                                                  200
```

<210> SEQ ID NO 7
<211> LENGTH: 119
<212> TYPE: DNA
<213> ORGANISM: Artificial
<220> FEATURE:

<223> OTHER INFORMATION: HIV-1 FLAP

<400> SEQUENCE: 7

```
ttttaaaaga aaggggggga ttgggggggta cagtgcaggg gaaagaatag tagacataat      60
agcaacagac atacaaacta aagaattaca aaaacaaatt acaaaaattc aaaattttc      119
```

```
<210> SEQ ID NO 8
<211> LENGTH: 2640
<212> TYPE: DNA
<213> ORGANISM: Bacteriophage T7
<220> FEATURE:
<221> NAME/KEY: misc_feature
<222> LOCATION: (1)..(2640)
<223> OTHER INFORMATION: T7 RNA polymerase gene
<220> FEATURE:
<221> NAME/KEY: CDS
<222> LOCATION: (10)..(2637)
```

<400> SEQUENCE: 8

```
ggctccacc atg gaa ttc tct gac atc gaa ctg gct gct atc ccg ttc aac      51
          Met Glu Phe Ser Asp Ile Glu Leu Ala Ala Ile Pro Phe Asn
          1               5                   10 act ctg gct gac cat tac ggt gag cgt tta gct cgc gaa cag ttg gcc         99
Thr Leu Ala Asp His Tyr Gly Glu Arg Leu Ala Arg Glu Gln Leu Ala
15                  20                  25                  30 ctt gag cat gag tct tac gag atg ggt gaa gca cgc ttc cgc aag atg        147
Leu Glu His Glu Ser Tyr Glu Met Gly Glu Ala Arg Phe Arg Lys Met
                35                  40                  45 ttt gag cgt caa ctt aaa gct ggt gag gtt gcg gat aac gct gcc gcc        195
Phe Glu Arg Gln Leu Lys Ala Gly Glu Val Ala Asp Asn Ala Ala Ala
            50                  55                  60 aag cct ctc atc act acc cta ctc cct aag atg att gca cgc atc aac        243
Lys Pro Leu Ile Thr Thr Leu Leu Pro Lys Met Ile Ala Arg Ile Asn
65                  70                  75 gac tgg ttt gag gaa gtg aaa gct aag cgc ggc aag cgc ccg aca gcc        291
Asp Trp Phe Glu Glu Val Lys Ala Lys Arg Gly Lys Arg Pro Thr Ala
80                  85                  90 ttc cag ttc ctg caa gaa atc aag ccg gaa gcc gta gcg tac atc acc        339
Phe Gln Phe Leu Gln Glu Ile Lys Pro Glu Ala Val Ala Tyr Ile Thr
95                  100                 105                 110 att aag acc act ctg gct tgc cta acc agt gct gac aat aca acc gtt        387
Ile Lys Thr Thr Leu Ala Cys Leu Thr Ser Ala Asp Asn Thr Thr Val
                115                 120                 125 cag gct gta gca agc gca atc ggt cgg gcc att gag gac gag gct cgc        435
Gln Ala Val Ala Ser Ala Ile Gly Arg Ala Ile Glu Asp Glu Ala Arg
            130                 135                 140 ttc ggt cgt atc cgt gac ctt gaa gct aag cac ttc aag aaa aac gtt        483
Phe Gly Arg Ile Arg Asp Leu Glu Ala Lys His Phe Lys Lys Asn Val
        145                 150                 155 gag gaa caa ctc aac aag cgc gta ggg cac gtc tac aag aaa gca ttt        531
Glu Glu Gln Leu Asn Lys Arg Val Gly His Val Tyr Lys Lys Ala Phe
160                 165                 170 atg caa gtt gtc gag gct gac atg ctc tct aag ggt cta ctc ggt ggc        579
Met Gln Val Val Glu Ala Asp Met Leu Ser Lys Gly Leu Leu Gly Gly
175                 180                 185                 190 gag gcg tgg tct tcg tgg cat aag gaa gac tct att cat gta gga gta        627
Glu Ala Trp Ser Ser Trp His Lys Glu Asp Ser Ile His Val Gly Val
                195                 200                 205 cgc tgc atc gag atg ctc att gag tca acc gga atg gtt agc tta cac        675
Arg Cys Ile Glu Met Leu Ile Glu Ser Thr Gly Met Val Ser Leu His
            210                 215                 220
```

-continued

| | |
|---|---|
| cgc caa aat gct ggt gta gta ggt caa gac tct gag act atc gaa ctc<br>Arg Gln Asn Ala Gly Val Val Gly Gln Asp Ser Glu Thr Ile Glu Leu<br>225                230                  235 | 723 |
| gca cct gaa tac gct gag gct atc gca acc cgt gca ggt gcg ctg gct<br>Ala Pro Glu Tyr Ala Glu Ala Ile Ala Thr Arg Ala Gly Ala Leu Ala<br>240                245                  250 | 771 |
| ggc atc tct ccg atg ttc caa cct tgc gta gtt cct cct aag ccg tgg<br>Gly Ile Ser Pro Met Phe Gln Pro Cys Val Val Pro Pro Lys Pro Trp<br>255                260                265                270 | 819 |
| act ggc att act ggt ggt ggc tat tgg gct aac ggt cgt cgt cct ctg<br>Thr Gly Ile Thr Gly Gly Gly Tyr Trp Ala Asn Gly Arg Arg Pro Leu<br>                275                280                  285 | 867 |
| gcg ctg gtg cgt act cac agt aag aaa gca ctg atg cgc tac gaa gac<br>Ala Leu Val Arg Thr His Ser Lys Lys Ala Leu Met Arg Tyr Glu Asp<br>290                295                  300 | 915 |
| gtt tac atg cct gag gtg tac aaa gcg att aac att gcg caa aac acc<br>Val Tyr Met Pro Glu Val Tyr Lys Ala Ile Asn Ile Ala Gln Asn Thr<br>                305                310                  315 | 963 |
| gca tgg aaa atc aac aag aaa gtc cta gcg gtc gcc aac gta atc acc<br>Ala Trp Lys Ile Asn Lys Lys Val Leu Ala Val Ala Asn Val Ile Thr<br>320                325                  330 | 1011 |
| aag tgg aag cat tgt ccg gtc gag gac atc cct gcg att gag cgt gaa<br>Lys Trp Lys His Cys Pro Val Glu Asp Ile Pro Ala Ile Glu Arg Glu<br>335                340                345                350 | 1059 |
| gaa ctc ccg atg aaa ccg gaa gac atc gac atg aat cct gag gct ctc<br>Glu Leu Pro Met Lys Pro Glu Asp Ile Asp Met Asn Pro Glu Ala Leu<br>                355                360                  365 | 1107 |
| acc gcg tgg aaa cgt gct gcc gct gct gtg tac cgc aag gac agg gct<br>Thr Ala Trp Lys Arg Ala Ala Ala Ala Val Tyr Arg Lys Asp Arg Ala<br>                       370                375                380 | 1155 |
| cgc aag tct cgc cgt atc agc ctt gag ttc atg ctt gag caa gcc aat<br>Arg Lys Ser Arg Arg Ile Ser Leu Glu Phe Met Leu Glu Gln Ala Asn<br>385                390                395 | 1203 |
| aag ttt gct aac cat aag gcc atc tgg ttc cct tac aac atg gac tgg<br>Lys Phe Ala Asn His Lys Ala Ile Trp Phe Pro Tyr Asn Met Asp Trp<br>400                405                  410 | 1251 |
| cgc ggt cgt gtt tac gcc gtg tca atg ttc aac ccg caa ggt aac gat<br>Arg Gly Arg Val Tyr Ala Val Ser Met Phe Asn Pro Gln Gly Asn Asp<br>415                420                425                430 | 1299 |
| atg acc aaa gga ctg ctt acg ctg gcg aaa ggt aaa cca atc ggt aag<br>Met Thr Lys Gly Leu Leu Thr Leu Ala Lys Gly Lys Pro Ile Gly Lys<br>                435                440                  445 | 1347 |
| gaa ggt tac tac tgg ctg aaa atc cac ggt gca aac tgt gcg ggt gtc<br>Glu Gly Tyr Tyr Trp Leu Lys Ile His Gly Ala Asn Cys Ala Gly Val<br>450                455                  460 | 1395 |
| gat aag gtt ccg ttc cct gag cgc atc aag ttc att gag gaa aac cac<br>Asp Lys Val Pro Phe Pro Glu Arg Ile Lys Phe Ile Glu Glu Asn His<br>465                470                475 | 1443 |
| gag aac atc atg gct tgc gct aag tct cca ctg gag aac act tgg tgg<br>Glu Asn Ile Met Ala Cys Ala Lys Ser Pro Leu Glu Asn Thr Trp Trp<br>480                485                  490 | 1491 |
| gct gag caa gat tct ccg ttc tgc ttc ctt gcg ttc tgc ttt gag tac<br>Ala Glu Gln Asp Ser Pro Phe Cys Phe Leu Ala Phe Cys Phe Glu Tyr<br>495                500                505                510 | 1539 |
| gct ggg gta cag cac cac ggc ctg agc tat aac tgc tcc ctt ccg ctg<br>Ala Gly Val Gln His His Gly Leu Ser Tyr Asn Cys Ser Leu Pro Leu<br>                515                520                  525 | 1587 |
| gcg ttt gac ggg tct tgc tct ggc atc cag cac ttc tcc gcg atg ctc<br>Ala Phe Asp Gly Ser Cys Ser Gly Ile Gln His Phe Ser Ala Met Leu<br>530                535                540 | 1635 |

| | | | | | | | | | | | | | | | | |
|---|---|---|---|---|---|---|---|---|---|---|---|---|---|---|---|---|
| cga | gat | gag | gta | ggt | ggt | cgc | gcg | gtt | aac | ttg | ctt | cct | agt | gag | acc | 1683 |
| Arg | Asp | Glu | Val | Gly | Gly | Arg | Ala | Val | Asn | Leu | Leu | Pro | Ser | Glu | Thr | |
| | | 545 | | | | 550 | | | | | 555 | | | | | |
| gtt | cag | gac | atc | tac | ggg | att | gtt | gct | aag | aaa | gtc | aac | gag | att | cta | 1731 |
| Val | Gln | Asp | Ile | Tyr | Gly | Ile | Val | Ala | Lys | Lys | Val | Asn | Glu | Ile | Leu | |
| | | | 560 | | | | | 565 | | | | | 570 | | | |
| caa | gca | gac | gca | atc | aat | ggg | acc | gat | aac | gaa | gta | gtt | acc | gtg | acc | 1779 |
| Gln | Ala | Asp | Ala | Ile | Asn | Gly | Thr | Asp | Asn | Glu | Val | Val | Thr | Val | Thr | |
| 575 | | | | | 580 | | | | | 585 | | | | | 590 | |
| gat | gag | aac | act | ggt | gaa | atc | tct | gag | aaa | gtc | aag | ctg | ggc | act | aag | 1827 |
| Asp | Glu | Asn | Thr | Gly | Glu | Ile | Ser | Glu | Lys | Val | Lys | Leu | Gly | Thr | Lys | |
| | | | | 595 | | | | | 600 | | | | | 605 | | |
| gca | ctg | gct | ggt | caa | tgg | ctg | gct | cac | ggt | gtt | act | cgc | agt | gtg | act | 1875 |
| Ala | Leu | Ala | Gly | Gln | Trp | Leu | Ala | His | Gly | Val | Thr | Arg | Ser | Val | Thr | |
| | | | 610 | | | | | 615 | | | | | 620 | | | |
| aag | cgt | tca | gtc | atg | acg | ctg | gct | tac | ggg | tcc | aaa | gag | ttc | ggc | ttc | 1923 |
| Lys | Arg | Ser | Val | Met | Thr | Leu | Ala | Tyr | Gly | Ser | Lys | Glu | Phe | Gly | Phe | |
| | | 625 | | | | 630 | | | | | 635 | | | | | |
| cgt | caa | caa | gtg | ctg | gaa | gat | acc | att | cag | cca | gct | att | gat | tcc | ggc | 1971 |
| Arg | Gln | Gln | Val | Leu | Glu | Asp | Thr | Ile | Gln | Pro | Ala | Ile | Asp | Ser | Gly | |
| | | 640 | | | | 645 | | | | | 650 | | | | | |
| aag | ggt | ccg | atg | ttc | act | cag | ccg | aat | cag | gct | gct | gga | tac | atg | gct | 2019 |
| Lys | Gly | Pro | Met | Phe | Thr | Gln | Pro | Asn | Gln | Ala | Ala | Gly | Tyr | Met | Ala | |
| 655 | | | | | 660 | | | | | 665 | | | | | 670 | |
| aag | ctg | att | tgg | gaa | tct | gtg | agc | gtg | acg | gtg | gta | gct | gcg | gtt | gaa | 2067 |
| Lys | Leu | Ile | Trp | Glu | Ser | Val | Ser | Val | Thr | Val | Val | Ala | Ala | Val | Glu | |
| | | | | 675 | | | | | 680 | | | | | 685 | | |
| gca | atg | aac | tgg | ctt | aag | tct | gct | gct | aag | ctg | ctg | gct | gct | gag | gtc | 2115 |
| Ala | Met | Asn | Trp | Leu | Lys | Ser | Ala | Ala | Lys | Leu | Leu | Ala | Ala | Glu | Val | |
| | | | 690 | | | | | 695 | | | | | 700 | | | |
| aaa | gat | aag | aag | act | gga | gag | att | ctt | cgc | aag | cgt | tgc | gct | gtg | cat | 2163 |
| Lys | Asp | Lys | Lys | Thr | Gly | Glu | Ile | Leu | Arg | Lys | Arg | Cys | Ala | Val | His | |
| | | 705 | | | | 710 | | | | | 715 | | | | | |
| tgg | gta | act | cct | gat | ggt | ttc | cct | gtg | tgg | cag | gaa | tac | aag | aag | cct | 2211 |
| Trp | Val | Thr | Pro | Asp | Gly | Phe | Pro | Val | Trp | Gln | Glu | Tyr | Lys | Lys | Pro | |
| | | 720 | | | | 725 | | | | | 730 | | | | | |
| att | cag | acg | cgc | ttg | aac | ctg | atg | ttc | ctc | ggt | cag | ttc | cgc | tta | cag | 2259 |
| Ile | Gln | Thr | Arg | Leu | Asn | Leu | Met | Phe | Leu | Gly | Gln | Phe | Arg | Leu | Gln | |
| 735 | | | | | 740 | | | | | 745 | | | | | 750 | |
| cct | acc | att | aac | acc | aac | aaa | gat | agc | gag | att | gat | gca | cac | aaa | cag | 2307 |
| Pro | Thr | Ile | Asn | Thr | Asn | Lys | Asp | Ser | Glu | Ile | Asp | Ala | His | Lys | Gln | |
| | | | | 755 | | | | | 760 | | | | | 765 | | |
| gag | tct | ggt | atc | gct | cct | aac | ttt | gta | cac | agc | caa | gac | ggt | agc | cac | 2355 |
| Glu | Ser | Gly | Ile | Ala | Pro | Asn | Phe | Val | His | Ser | Gln | Asp | Gly | Ser | His | |
| | | | 770 | | | | | 775 | | | | | 780 | | | |
| ctt | cgt | aag | act | gta | gtg | tgg | gca | cac | gag | aag | tac | gga | atc | gaa | tct | 2403 |
| Leu | Arg | Lys | Thr | Val | Val | Trp | Ala | His | Glu | Lys | Tyr | Gly | Ile | Glu | Ser | |
| | | 785 | | | | 790 | | | | | 795 | | | | | |
| ttt | gca | ctg | att | cac | gac | tcc | ttc | ggt | acc | att | ccg | gct | gac | gct | gcg | 2451 |
| Phe | Ala | Leu | Ile | His | Asp | Ser | Phe | Gly | Thr | Ile | Pro | Ala | Asp | Ala | Ala | |
| | | 800 | | | | 805 | | | | | 810 | | | | | |
| aac | ctg | ttc | aaa | gca | gtg | cgc | gaa | act | atg | gtt | gac | aca | tat | gag | tct | 2499 |
| Asn | Leu | Phe | Lys | Ala | Val | Arg | Glu | Thr | Met | Val | Asp | Thr | Tyr | Glu | Ser | |
| 815 | | | | | 820 | | | | | 825 | | | | | 830 | |
| tgt | gat | gta | ctg | gct | gat | ttc | tac | gac | cag | ttc | gct | gac | cag | ttg | cac | 2547 |
| Cys | Asp | Val | Leu | Ala | Asp | Phe | Tyr | Asp | Gln | Phe | Ala | Asp | Gln | Leu | His | |
| | | | | 835 | | | | | 840 | | | | | 845 | | |
| gag | tct | caa | ttg | gac | aaa | atg | cca | gca | ctt | ccg | gct | aaa | ggt | aac | ttg | 2595 |
| Glu | Ser | Gln | Leu | Asp | Lys | Met | Pro | Ala | Leu | Pro | Ala | Lys | Gly | Asn | Leu | |

-continued

```
                      850                 855                 860
       aac ctc cgt gac atc tta gag tcg gac ttc gcg ttc gcg tga taa        2640
       Asn Leu Arg Asp Ile Leu Glu Ser Asp Phe Ala Phe Ala
                      865                 870                 875
```

<210> SEQ ID NO 9
<211> LENGTH: 875
<212> TYPE: PRT
<213> ORGANISM: Bacteriophage T7

<400> SEQUENCE: 9

```
Met Glu Phe Ser Asp Ile Glu Leu Ala Ala Ile Pro Phe Asn Thr Leu
1               5                   10                  15

Ala Asp His Tyr Gly Glu Arg Leu Ala Arg Glu Gln Leu Ala Leu Glu
                20                  25                  30

His Glu Ser Tyr Glu Met Gly Glu Ala Arg Phe Arg Lys Met Phe Glu
            35                  40                  45

Arg Gln Leu Lys Ala Gly Glu Val Ala Asp Asn Ala Ala Ala Lys Pro
        50                  55                  60

Leu Ile Thr Thr Leu Leu Pro Lys Met Ile Ala Arg Ile Asn Asp Trp
65                  70                  75                  80

Phe Glu Glu Val Lys Ala Lys Arg Gly Lys Arg Pro Thr Ala Phe Gln
                85                  90                  95

Phe Leu Gln Glu Ile Lys Pro Glu Ala Val Ala Tyr Ile Thr Ile Lys
            100                 105                 110

Thr Thr Leu Ala Cys Leu Thr Ser Ala Asp Asn Thr Thr Val Gln Ala
        115                 120                 125

Val Ala Ser Ala Ile Gly Arg Ala Ile Glu Asp Glu Ala Arg Phe Gly
    130                 135                 140

Arg Ile Arg Asp Leu Glu Ala Lys His Phe Lys Lys Asn Val Glu Glu
145                 150                 155                 160

Gln Leu Asn Lys Arg Val Gly His Val Tyr Lys Lys Ala Phe Met Gln
                165                 170                 175

Val Val Glu Ala Asp Met Leu Ser Lys Gly Leu Leu Gly Gly Glu Ala
            180                 185                 190

Trp Ser Ser Trp His Lys Glu Asp Ser Ile His Val Gly Val Arg Cys
        195                 200                 205

Ile Glu Met Leu Ile Glu Ser Thr Gly Met Val Ser Leu His Arg Gln
    210                 215                 220

Asn Ala Gly Val Val Gly Gln Asp Ser Glu Thr Ile Glu Leu Ala Pro
225                 230                 235                 240

Glu Tyr Ala Glu Ala Ile Ala Thr Arg Ala Gly Ala Leu Ala Gly Ile
                245                 250                 255

Ser Pro Met Phe Gln Pro Cys Val Val Pro Pro Lys Pro Trp Thr Gly
            260                 265                 270

Ile Thr Gly Gly Gly Tyr Trp Ala Asn Gly Arg Arg Pro Leu Ala Leu
        275                 280                 285

Val Arg Thr His Ser Lys Lys Ala Leu Met Arg Tyr Glu Asp Val Tyr
    290                 295                 300

Met Pro Glu Val Tyr Lys Ala Ile Asn Ile Ala Gln Asn Thr Ala Trp
305                 310                 315                 320

Lys Ile Asn Lys Lys Val Leu Ala Val Ala Asn Val Ile Thr Lys Trp
                325                 330                 335

Lys His Cys Pro Val Glu Asp Ile Pro Ala Ile Glu Arg Glu Glu Leu
            340                 345                 350
```

-continued

```
Pro Met Lys Pro Glu Asp Ile Asp Met Asn Pro Glu Ala Leu Thr Ala
    355                 360                 365
Trp Lys Arg Ala Ala Ala Val Tyr Arg Lys Asp Arg Ala Arg Lys
370                 375                 380
Ser Arg Arg Ile Ser Leu Glu Phe Met Leu Glu Gln Ala Asn Lys Phe
385                 390                 395                 400
Ala Asn His Lys Ala Ile Trp Phe Pro Tyr Asn Met Asp Trp Arg Gly
                405                 410                 415
Arg Val Tyr Ala Val Ser Met Phe Asn Pro Gln Gly Asn Asp Met Thr
            420                 425                 430
Lys Gly Leu Leu Thr Leu Ala Lys Gly Lys Pro Ile Gly Lys Glu Gly
        435                 440                 445
Tyr Tyr Trp Leu Lys Ile His Gly Ala Asn Cys Ala Gly Val Asp Lys
    450                 455                 460
Val Pro Phe Pro Glu Arg Ile Lys Phe Ile Glu Glu Asn His Glu Asn
465                 470                 475                 480
Ile Met Ala Cys Ala Lys Ser Pro Leu Glu Asn Thr Trp Trp Ala Glu
                485                 490                 495
Gln Asp Ser Pro Phe Cys Phe Leu Ala Phe Cys Phe Glu Tyr Ala Gly
            500                 505                 510
Val Gln His His Gly Leu Ser Tyr Asn Cys Ser Leu Pro Leu Ala Phe
        515                 520                 525
Asp Gly Ser Cys Ser Gly Ile Gln His Phe Ser Ala Met Leu Arg Asp
    530                 535                 540
Glu Val Gly Gly Arg Ala Val Asn Leu Leu Pro Ser Glu Thr Val Gln
545                 550                 555                 560
Asp Ile Tyr Gly Ile Val Ala Lys Lys Val Asn Glu Ile Leu Gln Ala
                565                 570                 575
Asp Ala Ile Asn Gly Thr Asp Asn Glu Val Val Thr Val Thr Asp Glu
            580                 585                 590
Asn Thr Gly Glu Ile Ser Glu Lys Val Lys Leu Gly Thr Lys Ala Leu
        595                 600                 605
Ala Gly Gln Trp Leu Ala His Gly Val Thr Arg Ser Val Thr Lys Arg
    610                 615                 620
Ser Val Met Thr Leu Ala Tyr Gly Ser Lys Glu Phe Gly Phe Arg Gln
625                 630                 635                 640
Gln Val Leu Glu Asp Thr Ile Gln Pro Ala Ile Asp Ser Gly Lys Gly
                645                 650                 655
Pro Met Phe Thr Gln Pro Asn Gln Ala Ala Gly Tyr Met Ala Lys Leu
            660                 665                 670
Ile Trp Glu Ser Val Ser Val Thr Val Val Ala Ala Val Glu Ala Met
    675                 680                 685
Asn Trp Leu Lys Ser Ala Ala Lys Leu Leu Ala Glu Val Lys Asp
        690                 695                 700
Lys Lys Thr Gly Glu Ile Leu Arg Lys Arg Cys Ala Val His Trp Val
705                 710                 715                 720
Thr Pro Asp Gly Phe Pro Val Trp Gln Glu Tyr Lys Lys Pro Ile Gln
                725                 730                 735
Thr Arg Leu Asn Leu Met Phe Leu Gly Gln Phe Arg Leu Gln Pro Thr
            740                 745                 750
Ile Asn Thr Asn Lys Asp Ser Glu Ile Asp Ala His Lys Gln Glu Ser
        755                 760                 765
```

```
Gly Ile Ala Pro Asn Phe Val His Ser Gln Asp Gly Ser His Leu Arg
    770             775                 780

Lys Thr Val Val Trp Ala His Glu Lys Tyr Gly Ile Glu Ser Phe Ala
785                 790                 795                 800

Leu Ile His Asp Ser Phe Gly Thr Ile Pro Ala Asp Ala Ala Asn Leu
                805                 810                 815

Phe Lys Ala Val Arg Glu Thr Met Val Asp Thr Tyr Glu Ser Cys Asp
                820                 825                 830

Val Leu Ala Asp Phe Tyr Asp Gln Phe Ala Asp Gln Leu His Glu Ser
                835                 840                 845

Gln Leu Asp Lys Met Pro Ala Leu Pro Ala Lys Gly Asn Leu Asn Leu
850                 855                 860

Arg Asp Ile Leu Glu Ser Asp Phe Ala Phe Ala
865                 870                 875

<210> SEQ ID NO 10
<211> LENGTH: 2676
<212> TYPE: DNA
<213> ORGANISM: Bacteriophage T7
<220> FEATURE:
<221> NAME/KEY: misc_feature
<222> LOCATION: (1)..(2676)
<223> OTHER INFORMATION: nls T7 RNA polymerase gene
<220> FEATURE:
<221> NAME/KEY: CDS
<222> LOCATION: (10)..(2673)

<400> SEQUENCE: 10 ggctccacc atg gca cca aaa aag aag aga aag gta gaa gac ccc aag gaa      51
          Met Ala Pro Lys Lys Lys Arg Lys Val Glu Asp Pro Lys Glu
          1               5                   10 ttc tct gac atc gaa ctg gct gct atc ccg ttc aac act ctg gct gac      99
Phe Ser Asp Ile Glu Leu Ala Ala Ile Pro Phe Asn Thr Leu Ala Asp
15                  20                  25                  30 cat tac ggt gag cgt tta gct cgc gaa cag ttg gcc ctt gag cat gag     147
His Tyr Gly Glu Arg Leu Ala Arg Glu Gln Leu Ala Leu Glu His Glu
                35                  40                  45 tct tac gag atg ggt gaa gca cgc ttc cgc aag atg ttt gag cgt caa     195
Ser Tyr Glu Met Gly Glu Ala Arg Phe Arg Lys Met Phe Glu Arg Gln
            50                  55                  60 ctt aaa gct ggt gag gtt gcg gat aac gct gcc gcc aag cct ctc atc     243
Leu Lys Ala Gly Glu Val Ala Asp Asn Ala Ala Ala Lys Pro Leu Ile
        65                  70                  75 act acc cta ctc cct aag atg att gca cgc atc aac gac tgg ttt gag     291
Thr Thr Leu Leu Pro Lys Met Ile Ala Arg Ile Asn Asp Trp Phe Glu
80                  85                  90 gaa gtg aaa gct aag cgc ggc aag cgc ccg aca gcc ttc cag ttc ctg     339
Glu Val Lys Ala Lys Arg Gly Lys Arg Pro Thr Ala Phe Gln Phe Leu
95                  100                 105                 110 caa gaa atc aag ccg gaa gcc gta gcg tac atc acc att aag acc act     387
Gln Glu Ile Lys Pro Glu Ala Val Ala Tyr Ile Thr Ile Lys Thr Thr
                115                 120                 125 ctg gct tgc cta acc agt gct gac aat aca acc gtt cag gct gta gca     435
Leu Ala Cys Leu Thr Ser Ala Asp Asn Thr Thr Val Gln Ala Val Ala
            130                 135                 140 agc gca atc ggt cgg gcc att gag gac gag gct cgc ttc ggt cgt atc     483
Ser Ala Ile Gly Arg Ala Ile Glu Asp Glu Ala Arg Phe Gly Arg Ile
        145                 150                 155 cgt gac ctt gaa gct aag cac ttc aag aaa aac gtt gag gaa caa ctc     531
Arg Asp Leu Glu Ala Lys His Phe Lys Lys Asn Val Glu Glu Gln Leu
    160                 165                 170
```

| | | |
|---|---|---|
| aac aag cgc gta ggg cac gtc tac aag aaa gca ttt atg caa gtt gtc<br>Asn Lys Arg Val Gly His Val Tyr Lys Lys Ala Phe Met Gln Val Val<br>175                   180                 185                 190 | 579 |
| gag gct gac atg ctc tct aag ggt cta ctc ggt ggc gag gcg tgg tct<br>Glu Ala Asp Met Leu Ser Lys Gly Leu Leu Gly Gly Glu Ala Trp Ser<br>                   195                 200                 205 | 627 |
| tcg tgg cat aag gaa gac tct att cat gta gga gta cgc tgc atc gag<br>Ser Trp His Lys Glu Asp Ser Ile His Val Gly Val Arg Cys Ile Glu<br>             210                 215                 220 | 675 |
| atg ctc att gag tca acc gga atg gtt agc tta cac cgc caa aat gct<br>Met Leu Ile Glu Ser Thr Gly Met Val Ser Leu His Arg Gln Asn Ala<br>225                 230                 235 | 723 |
| ggc gta gta ggt caa gac tct gag act atc gaa ctc gca cct gaa tac<br>Gly Val Val Gly Gln Asp Ser Glu Thr Ile Glu Leu Ala Pro Glu Tyr<br>         240                 245                 250 | 771 |
| gct gag gct atc gca acc cgt gca ggt gcg ctg gct ggc atc tct ccg<br>Ala Glu Ala Ile Ala Thr Arg Ala Gly Ala Leu Ala Gly Ile Ser Pro<br>255                 260                 265                 270 | 819 |
| atg ttc caa cct tgc gta gtt cct cct aag ccg tgg act ggc att act<br>Met Phe Gln Pro Cys Val Val Pro Pro Lys Pro Trp Thr Gly Ile Thr<br>                   275                 280                 285 | 867 |
| ggt ggt ggc tat tgg gct aac ggt cgt cgt cct ctg gcg ctg gtg cgt<br>Gly Gly Gly Tyr Trp Ala Asn Gly Arg Arg Pro Leu Ala Leu Val Arg<br>             290                 295                 300 | 915 |
| act cac agt aag aaa gca ctg atg cgc tac gaa gac gtt tac atg cct<br>Thr His Ser Lys Lys Ala Leu Met Arg Tyr Glu Asp Val Tyr Met Pro<br>         305                 310                 315 | 963 |
| gag gtg tac aaa gcg att aac att gcg caa aac acc gca tgg aaa atc<br>Glu Val Tyr Lys Ala Ile Asn Ile Ala Gln Asn Thr Ala Trp Lys Ile<br>320                 325                 330 | 1011 |
| aac aag aaa gtc cta gcg gtc gcc aac gta atc acc aag tgg aag cat<br>Asn Lys Lys Val Leu Ala Val Ala Asn Val Ile Thr Lys Trp Lys His<br>335                 340                 345                 350 | 1059 |
| tgt ccg gtc gag gac atc cct gcg att gag cgt gaa gaa ctc ccg atg<br>Cys Pro Val Glu Asp Ile Pro Ala Ile Glu Arg Glu Glu Leu Pro Met<br>                   355                 360                 365 | 1107 |
| aaa ccg gaa gac atc gac atg aat cct gag gct ctc acc gcg tgg aaa<br>Lys Pro Glu Asp Ile Asp Met Asn Pro Glu Ala Leu Thr Ala Trp Lys<br>             370                 375                 380 | 1155 |
| cgt gct gcc gct gct gtg tac cgc aag gac agg gct cgc aag tct cgc<br>Arg Ala Ala Ala Ala Val Tyr Arg Lys Asp Arg Ala Arg Lys Ser Arg<br>         385                 390                 395 | 1203 |
| cgt atc agc ctt gag ttc atg ctt gag caa gcc aat aag ttt gct aac<br>Arg Ile Ser Leu Glu Phe Met Leu Glu Gln Ala Asn Lys Phe Ala Asn<br>400                 405                 410 | 1251 |
| cat aag gcc atc tgg ttc cct tac aac atg gac tgg cgc ggt cgt gtt<br>His Lys Ala Ile Trp Phe Pro Tyr Asn Met Asp Trp Arg Gly Arg Val<br>415                 420                 425                 430 | 1299 |
| tac gcc gtg tca atg ttc aac ccg caa ggt aac gat atg acc aaa gga<br>Tyr Ala Val Ser Met Phe Asn Pro Gln Gly Asn Asp Met Thr Lys Gly<br>                   435                 440                 445 | 1347 |
| ctg ctt acg ctg gcg aaa ggt aaa cca atc ggt aag gaa ggt tac tac<br>Leu Leu Thr Leu Ala Lys Gly Lys Pro Ile Gly Lys Glu Gly Tyr Tyr<br>             450                 455                 460 | 1395 |
| tgg ctg aaa atc cac ggt gca aac tgt gcg ggt gtc gat aag gtt ccg<br>Trp Leu Lys Ile His Gly Ala Asn Cys Ala Gly Val Asp Lys Val Pro<br>465                 470                 475 | 1443 |
| ttc cct gag cgc atc aag ttc att gag gaa aac cac gag aac atc atg<br>Phe Pro Glu Arg Ile Lys Phe Ile Glu Glu Asn His Glu Asn Ile Met | 1491 |

```
                480             485             490
gct tgc gct aag tct cca ctg gag aac act tgg tgg gct gag caa gat    1539
Ala Cys Ala Lys Ser Pro Leu Glu Asn Thr Trp Trp Ala Glu Gln Asp
495             500             505             510 tct ccg ttc tgc ttc ctt gcg ttc tgc ttt gag tac gct ggg gta cag    1587
Ser Pro Phe Cys Phe Leu Ala Phe Cys Phe Glu Tyr Ala Gly Val Gln
            515             520             525 cac cac ggc ctg agc tat aac tgc tcc ctt ccg ctg gcg ttt gac ggg    1635
His His Gly Leu Ser Tyr Asn Cys Ser Leu Pro Leu Ala Phe Asp Gly
        530             535             540 tct tgc tct ggc atc cag cac ttc tcc gcg atg ctc cga gat gag gta    1683
Ser Cys Ser Gly Ile Gln His Phe Ser Ala Met Leu Arg Asp Glu Val
    545             550             555 ggt ggt cgc gcg gtt aac ttg ctt cct agt gag acc gtt cag gac atc    1731
Gly Gly Arg Ala Val Asn Leu Leu Pro Ser Glu Thr Val Gln Asp Ile
560             565             570 tac ggg att gtt gct aag aaa gtc aac gag att cta caa gca gac gca    1779
Tyr Gly Ile Val Ala Lys Lys Val Asn Glu Ile Leu Gln Ala Asp Ala
575             580             585             590 atc aat ggg acc gat aac gaa gta gtt acc gtg acc gat gag aac act    1827
Ile Asn Gly Thr Asp Asn Glu Val Val Thr Val Thr Asp Glu Asn Thr
            595             600             605 ggt gaa atc tct gag aaa gtc aag ctg ggc act aag gca ctg gct ggt    1875
Gly Glu Ile Ser Glu Lys Val Lys Leu Gly Thr Lys Ala Leu Ala Gly
        610             615             620 caa tgg ctg gct cac ggt gtt act cgc agt gtg act aag cgt tca gtc    1923
Gln Trp Leu Ala His Gly Val Thr Arg Ser Val Thr Lys Arg Ser Val
    625             630             635 atg acg ctg gct tac ggg tcc aaa gag ttc ggc ttc cgt caa caa gtg    1971
Met Thr Leu Ala Tyr Gly Ser Lys Glu Phe Gly Phe Arg Gln Gln Val
640             645             650 ctg gaa gat acc att cag cca gct att gat tcc ggc aag ggt ccg atg    2019
Leu Glu Asp Thr Ile Gln Pro Ala Ile Asp Ser Gly Lys Gly Pro Met
655             660             665             670 ttc act cag ccg aat cag gct gct gga tac atg gct aag ctg att tgg    2067
Phe Thr Gln Pro Asn Gln Ala Ala Gly Tyr Met Ala Lys Leu Ile Trp
            675             680             685 gaa tct gtg agc gtg acg gtg gta gct gcg gtt gaa gca atg aac tgg    2115
Glu Ser Val Ser Val Thr Val Val Ala Ala Val Glu Ala Met Asn Trp
        690             695             700 ctt aag tct gct gct aag ctg ctg gct gct gag gtc aaa gat aag aag    2163
Leu Lys Ser Ala Ala Lys Leu Leu Ala Ala Glu Val Lys Asp Lys Lys
    705             710             715 act gga gag att ctt cgc aag cgt tgc gct gtg cat tgg gta act cct    2211
Thr Gly Glu Ile Leu Arg Lys Arg Cys Ala Val His Trp Val Thr Pro
720             725             730 gat ggt ttc cct gtg tgg cag gaa tac aag aag cct att cag acg cgc    2259
Asp Gly Phe Pro Val Trp Gln Glu Tyr Lys Lys Pro Ile Gln Thr Arg
735             740             745             750 ttg aac ctg atg ttc ctc ggt cag ttc cgc tta cag cct acc att aac    2307
Leu Asn Leu Met Phe Leu Gly Gln Phe Arg Leu Gln Pro Thr Ile Asn
            755             760             765 acc aac aaa gat agc gag att gat gca cac aaa cag gag tct ggt atc    2355
Thr Asn Lys Asp Ser Glu Ile Asp Ala His Lys Gln Glu Ser Gly Ile
        770             775             780 gct cct aac ttt gta cac agc caa gac ggt agc cac ctt cgt aag act    2403
Ala Pro Asn Phe Val His Ser Gln Asp Gly Ser His Leu Arg Lys Thr
    785             790             795 gta gtg tgg gca cac gag aag tac gga atc gaa tct ttt gca ctg att    2451
Val Val Trp Ala His Glu Lys Tyr Gly Ile Glu Ser Phe Ala Leu Ile
```

```
Val Val Trp Ala His Glu Lys Tyr Gly Ile Glu Ser Phe Ala Leu Ile
    800                 805                 810 cac gac tcc ttc ggt acc att ccg gct gac gct gcg aac ctg ttc aaa      2499
His Asp Ser Phe Gly Thr Ile Pro Ala Asp Ala Ala Asn Leu Phe Lys
815                 820                 825                 830 gca gtg cgc gaa act atg gtt gac aca tat gag tct tgt gat gta ctg      2547
Ala Val Arg Glu Thr Met Val Asp Thr Tyr Glu Ser Cys Asp Val Leu
                835                 840                 845 gct gat ttc tac gac cag ttc gct gac cag ttg cac gag tct caa ttg      2595
Ala Asp Phe Tyr Asp Gln Phe Ala Asp Gln Leu His Glu Ser Gln Leu
        850                 855                 860 gac aaa atg cca gca ctt ccg gct aaa ggt aac ttg aac ctc cgt gac      2643
Asp Lys Met Pro Ala Leu Pro Ala Lys Gly Asn Leu Asn Leu Arg Asp
    865                 870                 875 atc tta gag tcg gac ttc gcg ttc gcg tga taa                          2676
Ile Leu Glu Ser Asp Phe Ala Phe Ala
    880                 885

<210> SEQ ID NO 11
<211> LENGTH: 887
<212> TYPE: PRT
<213> ORGANISM: Bacteriophage T7

<400> SEQUENCE: 11

Met Ala Pro Lys Lys Arg Lys Val Glu Asp Pro Lys Glu Phe Ser
1               5                   10                  15

Asp Ile Glu Leu Ala Ala Ile Pro Phe Asn Thr Leu Ala Asp His Tyr
                20                  25                  30

Gly Glu Arg Leu Ala Arg Glu Gln Leu Ala Leu Glu His Glu Ser Tyr
            35                  40                  45

Glu Met Gly Glu Ala Arg Phe Arg Lys Met Phe Glu Arg Gln Leu Lys
50                  55                  60

Ala Gly Glu Val Ala Asp Asn Ala Ala Ala Lys Pro Leu Ile Thr Thr
65                  70                  75                  80

Leu Leu Pro Lys Met Ile Ala Arg Ile Asn Asp Trp Phe Glu Glu Val
                85                  90                  95

Lys Ala Lys Arg Gly Lys Arg Pro Thr Ala Phe Gln Phe Leu Gln Glu
            100                 105                 110

Ile Lys Pro Glu Ala Val Ala Tyr Ile Thr Ile Lys Thr Thr Leu Ala
        115                 120                 125

Cys Leu Thr Ser Ala Asp Asn Thr Thr Val Gln Ala Val Ala Ser Ala
130                 135                 140

Ile Gly Arg Ala Ile Glu Asp Glu Ala Arg Phe Gly Arg Ile Arg Asp
145                 150                 155                 160

Leu Glu Ala Lys His Phe Lys Lys Asn Val Glu Glu Gln Leu Asn Lys
                165                 170                 175

Arg Val Gly His Val Tyr Lys Lys Ala Phe Met Gln Val Val Glu Ala
            180                 185                 190

Asp Met Leu Ser Lys Gly Leu Leu Gly Gly Glu Ala Trp Ser Ser Trp
        195                 200                 205

His Lys Glu Asp Ser Ile His Val Gly Val Arg Cys Ile Glu Met Leu
210                 215                 220

Ile Glu Ser Thr Gly Met Val Ser Leu His Arg Gln Asn Ala Gly Val
225                 230                 235                 240

Val Gly Gln Asp Ser Glu Thr Ile Glu Leu Ala Pro Glu Tyr Ala Glu
                245                 250                 255
```

-continued

Ala Ile Ala Thr Arg Ala Gly Ala Leu Ala Gly Ile Ser Pro Met Phe
            260                 265                 270

Gln Pro Cys Val Val Pro Lys Pro Trp Thr Gly Ile Thr Gly Gly
        275                 280                 285

Gly Tyr Trp Ala Asn Gly Arg Arg Pro Leu Ala Leu Val Arg Thr His
    290                 295                 300

Ser Lys Lys Ala Leu Met Arg Tyr Glu Asp Val Tyr Met Pro Glu Val
305                 310                 315                 320

Tyr Lys Ala Ile Asn Ile Ala Gln Asn Thr Ala Trp Lys Ile Asn Lys
                325                 330                 335

Lys Val Leu Ala Val Ala Asn Val Ile Thr Lys Trp Lys His Cys Pro
            340                 345                 350

Val Glu Asp Ile Pro Ala Ile Glu Arg Glu Glu Leu Pro Met Lys Pro
        355                 360                 365

Glu Asp Ile Asp Met Asn Pro Glu Ala Leu Thr Ala Trp Lys Arg Ala
    370                 375                 380

Ala Ala Ala Val Tyr Arg Lys Asp Arg Ala Arg Lys Ser Arg Arg Ile
385                 390                 395                 400

Ser Leu Glu Phe Met Leu Glu Gln Ala Asn Lys Phe Ala Asn His Lys
                405                 410                 415

Ala Ile Trp Phe Pro Tyr Asn Met Asp Trp Arg Gly Arg Val Tyr Ala
            420                 425                 430

Val Ser Met Phe Asn Pro Gln Gly Asn Asp Met Thr Lys Gly Leu Leu
        435                 440                 445

Thr Leu Ala Lys Gly Lys Pro Ile Gly Lys Glu Gly Tyr Tyr Trp Leu
    450                 455                 460

Lys Ile His Gly Ala Asn Cys Ala Gly Val Asp Lys Val Pro Phe Pro
465                 470                 475                 480

Glu Arg Ile Lys Phe Ile Glu Asn His Glu Asn Ile Met Ala Cys
                485                 490                 495

Ala Lys Ser Pro Leu Glu Asn Thr Trp Trp Ala Glu Gln Asp Ser Pro
            500                 505                 510

Phe Cys Phe Leu Ala Phe Cys Phe Glu Tyr Ala Gly Val Gln His His
        515                 520                 525

Gly Leu Ser Tyr Asn Cys Ser Leu Pro Leu Ala Phe Asp Gly Ser Cys
    530                 535                 540

Ser Gly Ile Gln His Phe Ser Ala Met Leu Arg Asp Glu Val Gly Gly
545                 550                 555                 560

Arg Ala Val Asn Leu Leu Pro Ser Glu Thr Val Gln Asp Ile Tyr Gly
                565                 570                 575

Ile Val Ala Lys Lys Val Asn Glu Ile Leu Gln Ala Asp Ala Ile Asn
            580                 585                 590

Gly Thr Asp Asn Glu Val Val Thr Val Thr Asp Glu Asn Thr Gly Glu
        595                 600                 605

Ile Ser Glu Lys Val Lys Leu Gly Thr Lys Ala Leu Ala Gly Gln Trp
    610                 615                 620

Leu Ala His Gly Val Thr Arg Ser Val Thr Lys Arg Ser Val Met Thr
625                 630                 635                 640

Leu Ala Tyr Gly Ser Lys Glu Phe Gly Phe Arg Gln Gln Val Leu Glu
                645                 650                 655

Asp Thr Ile Gln Pro Ala Ile Asp Ser Gly Lys Gly Pro Met Phe Thr
            660                 665                 670

Gln Pro Asn Gln Ala Ala Gly Tyr Met Ala Lys Leu Ile Trp Glu Ser

```
              675                 680                 685
Val Ser Val Thr Val Val Ala Val Glu Ala Met Asn Trp Leu Lys
    690                 695                 700

Ser Ala Ala Lys Leu Leu Ala Ala Glu Val Lys Asp Lys Lys Thr Gly
705                 710                 715                 720

Glu Ile Leu Arg Lys Arg Cys Ala Val His Trp Val Thr Pro Asp Gly
                725                 730                 735

Phe Pro Val Trp Gln Glu Tyr Lys Lys Pro Ile Gln Thr Arg Leu Asn
            740                 745                 750

Leu Met Phe Leu Gly Gln Phe Arg Leu Gln Pro Thr Ile Asn Thr Asn
        755                 760                 765

Lys Asp Ser Glu Ile Asp Ala His Lys Gln Glu Ser Gly Ile Ala Pro
    770                 775                 780

Asn Phe Val His Ser Gln Asp Gly Ser His Leu Arg Lys Thr Val Val
785                 790                 795                 800

Trp Ala His Glu Lys Tyr Gly Ile Glu Ser Phe Ala Leu Ile His Asp
                805                 810                 815

Ser Phe Gly Thr Ile Pro Ala Asp Ala Ala Asn Leu Phe Lys Ala Val
            820                 825                 830

Arg Glu Thr Met Val Asp Thr Tyr Glu Ser Cys Asp Val Leu Ala Asp
        835                 840                 845

Phe Tyr Asp Gln Phe Ala Asp Gln Leu His Glu Ser Gln Leu Asp Lys
    850                 855                 860

Met Pro Ala Leu Pro Ala Lys Gly Asn Leu Asn Leu Arg Asp Ile Leu
865                 870                 875                 880

Glu Ser Asp Phe Ala Phe Ala
                885

<210> SEQ ID NO 12
<211> LENGTH: 1578
<212> TYPE: DNA
<213> ORGANISM: Measles virus
<220> FEATURE:
<221> NAME/KEY: CDS
<222> LOCATION: (1)..(1578)
<220> FEATURE:
<221> NAME/KEY: misc_feature
<222> LOCATION: (1)..(1578)
<223> OTHER INFORMATION: Schwarz MV N gene

<400> SEQUENCE: 12 atg gcc aca ctt tta agg agc tta gca ttg ttc aaa aga aac aag gac       48
Met Ala Thr Leu Leu Arg Ser Leu Ala Leu Phe Lys Arg Asn Lys Asp
1               5                   10                  15 aaa cca ccc att aca tca gga tcc ggt gga gcc atc aga gga atc aaa       96
Lys Pro Pro Ile Thr Ser Gly Ser Gly Gly Ala Ile Arg Gly Ile Lys
            20                  25                  30 cac att att ata gta cca atc cct gga gat tcc tca att acc act cga      144
His Ile Ile Ile Val Pro Ile Pro Gly Asp Ser Ser Ile Thr Thr Arg
        35                  40                  45 tcc aga ctt ctg gac cgg ttg gtg agg tta att gga aac ccg gat gtg      192
Ser Arg Leu Leu Asp Arg Leu Val Arg Leu Ile Gly Asn Pro Asp Val
    50                  55                  60 agc ggg ccc aaa cta aca ggg gca cta ata ggt ata tta tcc tta ttt      240
Ser Gly Pro Lys Leu Thr Gly Ala Leu Ile Gly Ile Leu Ser Leu Phe
65                  70                  75                  80 gtg gag tct cca ggt caa ttg att cag agg atc acc gat gac cct gac      288
Val Glu Ser Pro Gly Gln Leu Ile Gln Arg Ile Thr Asp Asp Pro Asp
                85                  90                  95
```

```
gtt agc ata agg ctg tta gag gtt gtc cag agt gac cag tca caa tct    336
Val Ser Ile Arg Leu Leu Glu Val Val Gln Ser Asp Gln Ser Gln Ser
            100                 105                 110 ggc ctt acc ttc gca tca aga ggt acc aac atg gag gat gag gcg gac    384
Gly Leu Thr Phe Ala Ser Arg Gly Thr Asn Met Glu Asp Glu Ala Asp
        115                 120                 125 caa tac ttt tca cat gat gat cca att agt agt gat caa tcc agg ttc    432
Gln Tyr Phe Ser His Asp Asp Pro Ile Ser Ser Asp Gln Ser Arg Phe
    130                 135                 140 gga tgg ttc ggg aac aag gaa atc tca gat att gaa gtg caa gac cct    480
Gly Trp Phe Gly Asn Lys Glu Ile Ser Asp Ile Glu Val Gln Asp Pro
145                 150                 155                 160 gag gga ttc aac atg att ctg ggt acc atc cta gcc caa att tgg gtc    528
Glu Gly Phe Asn Met Ile Leu Gly Thr Ile Leu Ala Gln Ile Trp Val
                165                 170                 175 ttg ctc gca aag gcg gtt acg gcc cca gac acg gca gct gat tcg gag    576
Leu Leu Ala Lys Ala Val Thr Ala Pro Asp Thr Ala Ala Asp Ser Glu
            180                 185                 190 cta aga agg tgg ata aag tac acc caa caa aga agg gta gtt ggt gaa    624
Leu Arg Arg Trp Ile Lys Tyr Thr Gln Gln Arg Arg Val Val Gly Glu
        195                 200                 205 ttt aga ttg gag aga aaa tgg ttg gat gtg gtg agg aac agg att gcc    672
Phe Arg Leu Glu Arg Lys Trp Leu Asp Val Val Arg Asn Arg Ile Ala
    210                 215                 220 gag gac ctc tcc tta cgc cga ttc atg gtc gct cta atc ctg gat atc    720
Glu Asp Leu Ser Leu Arg Arg Phe Met Val Ala Leu Ile Leu Asp Ile
225                 230                 235                 240 aag aga aca ccc gga aac aaa ccc agg att gct gaa atg ata tgt gac    768
Lys Arg Thr Pro Gly Asn Lys Pro Arg Ile Ala Glu Met Ile Cys Asp
                245                 250                 255 att gat aca tat atc gta gag gca gga tta gcc agt ttt atc ctg act    816
Ile Asp Thr Tyr Ile Val Glu Ala Gly Leu Ala Ser Phe Ile Leu Thr
            260                 265                 270 att aag ttt ggg ata gaa act atg tat cct gct ctt gga ctg cat gaa    864
Ile Lys Phe Gly Ile Glu Thr Met Tyr Pro Ala Leu Gly Leu His Glu
        275                 280                 285 ttt gct ggt gag tta tcc aca ctt gag tcc ttg atg aac ctt tac cag    912
Phe Ala Gly Glu Leu Ser Thr Leu Glu Ser Leu Met Asn Leu Tyr Gln
    290                 295                 300 caa atg ggg gaa act gca ccc tac atg gta atc ctg gag aac tca att    960
Gln Met Gly Glu Thr Ala Pro Tyr Met Val Ile Leu Glu Asn Ser Ile
305                 310                 315                 320 cag aac aag ttc agt gca gga tca tac cct ctg ctc tgg agc tat gcc   1008
Gln Asn Lys Phe Ser Ala Gly Ser Tyr Pro Leu Leu Trp Ser Tyr Ala
                325                 330                 335 atg gga gta gga gtg gaa ctt gaa aac tcc atg gga ggt ttg aac ttt   1056
Met Gly Val Gly Val Glu Leu Glu Asn Ser Met Gly Gly Leu Asn Phe
            340                 345                 350 ggc cga tct tac ttt gat cca gca tat ttt aga tta ggg caa gag atg   1104
Gly Arg Ser Tyr Phe Asp Pro Ala Tyr Phe Arg Leu Gly Gln Glu Met
        355                 360                 365 gta agg agg tca gct gga aag gtc agt tcc aca ttg gca tct gaa ctc   1152
Val Arg Arg Ser Ala Gly Lys Val Ser Ser Thr Leu Ala Ser Glu Leu
    370                 375                 380 ggt atc act gcc gag gat gca agg ctt gtt tca gag att gca atg cat   1200
Gly Ile Thr Ala Glu Asp Ala Arg Leu Val Ser Glu Ile Ala Met His
385                 390                 395                 400 act act gag gac aag atc agt aga gcg gtt gga ccc aga caa gcc caa   1248
Thr Thr Glu Asp Lys Ile Ser Arg Ala Val Gly Pro Arg Gln Ala Gln
```

```
                        405                 410                 415
gta tca ttt cta cac ggt gat caa agt gag aat gag cta ccg aga ttg      1296
Val Ser Phe Leu His Gly Asp Gln Ser Glu Asn Glu Leu Pro Arg Leu
            420                 425                 430 ggg ggc aag gaa gat agg agg gtc aaa cag agt cga gga gaa gcc agg      1344
Gly Gly Lys Glu Asp Arg Arg Val Lys Gln Ser Arg Gly Glu Ala Arg
        435                 440                 445 gag agc tac aga gaa acc ggg ccc agc aga gca agt gat gcg aga gct      1392
Glu Ser Tyr Arg Glu Thr Gly Pro Ser Arg Ala Ser Asp Ala Arg Ala
    450                 455                 460 gcc cat ctt cca acc ggc aca ccc cta gac att gac act gca acg gag      1440
Ala His Leu Pro Thr Gly Thr Pro Leu Asp Ile Asp Thr Ala Thr Glu
465                 470                 475                 480 tcc agc caa gat ccg cag gac agt cga agg tca gct gac gcc ctg ctt      1488
Ser Ser Gln Asp Pro Gln Asp Ser Arg Arg Ser Ala Asp Ala Leu Leu
                485                 490                 495 agg ctg caa gcc atg gca gga atc tcg gaa gaa caa ggc tca gac acg      1536
Arg Leu Gln Ala Met Ala Gly Ile Ser Glu Glu Gln Gly Ser Asp Thr
            500                 505                 510 gac acc cct ata gtg tac aat gac aga aat ctt cta gac tag              1578
Asp Thr Pro Ile Val Tyr Asn Asp Arg Asn Leu Leu Asp
        515                 520                 525

<210> SEQ ID NO 13
<211> LENGTH: 525
<212> TYPE: PRT
<213> ORGANISM: Measles virus

<400> SEQUENCE: 13

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220
```

```
Glu Asp Leu Ser Leu Arg Arg Phe Met Val Ala Ile Leu Asp Ile
225                 230                 235                 240

Lys Arg Thr Pro Gly Asn Lys Pro Arg Ile Ala Glu Met Ile Cys Asp
        245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
            325                 330                 335

Met Gly Val Gly Val Glu Leu Glu Asn Ser Met Gly Gly Leu Asn Phe
        340                 345                 350

Gly Arg Ser Tyr Phe Asp Pro Ala Tyr Phe Arg Leu Gly Gln Glu Met
    355                 360                 365

Val Arg Arg Ser Ala Gly Lys Val Ser Ser Thr Leu Ala Ser Glu Leu
370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
            405                 410                 415

Val Ser Phe Leu His Gly Asp Gln Ser Glu Asn Glu Leu Pro Arg Leu
        420                 425                 430

Gly Gly Lys Glu Asp Arg Arg Val Lys Gln Ser Arg Gly Glu Ala Arg
    435                 440                 445

Glu Ser Tyr Arg Glu Thr Gly Pro Ser Arg Ala Ser Asp Ala Arg Ala
450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
            485                 490                 495

Arg Leu Gln Ala Met Ala Gly Ile Ser Glu Glu Gln Gly Ser Asp Thr
        500                 505                 510

Asp Thr Pro Ile Val Tyr Asn Asp Arg Asn Leu Leu Asp
        515                 520                 525

<210> SEQ ID NO 14
<211> LENGTH: 1524
<212> TYPE: DNA
<213> ORGANISM: Measles virus
<220> FEATURE:
<221> NAME/KEY: CDS
<222> LOCATION: (1)..(1524)
<220> FEATURE:
<221> NAME/KEY: misc_feature
<222> LOCATION: (1)..(1524)
<223> OTHER INFORMATION: Schw -continued

```
               20                  25                  30
atg gca gca tgg tca gaa ata tca gac aac cca gga cag gag cga gcc      144
Met Ala Ala Trp Ser Glu Ile Ser Asp Asn Pro Gly Gln Glu Arg Ala
         35                  40                  45 acc tgc agg gaa gag aag gca ggc agt tcg ggt ctc agc aaa cca tgc      192
Thr Cys Arg Glu Glu Lys Ala Gly Ser Ser Gly Leu Ser Lys Pro Cys
 50                  55                  60 ctc tca gca att gga tca act gaa ggc ggt gca cct cgc atc cgc ggt      240
Leu Ser Ala Ile Gly Ser Thr Glu Gly Gly Ala Pro Arg Ile Arg Gly
 65                  70                  75                  80 cag gga cct gga gag agc gat gac gac gct gaa act ttg gga atc ccc      288
Gln Gly Pro Gly Glu Ser Asp Asp Asp Ala Glu Thr Leu Gly Ile Pro
                 85                  90                  95 cca aga aat ctc cag gca tca agc act ggg tta cag tgt tat tac gtt      336
Pro Arg Asn Leu Gln Ala Ser Ser Thr Gly Leu Gln Cys Tyr Tyr Val
            100                 105                 110 tat gat cac agc ggt gaa gcg gtt aag gga atc caa gat gct gac tct      384
Tyr Asp His Ser Gly Glu Ala Val Lys Gly Ile Gln Asp Ala Asp Ser
        115                 120                 125 atc atg gtt caa tca ggc ctt gat ggt gat agc acc ctc tca gga gga      432
Ile Met Val Gln Ser Gly Leu Asp Gly Asp Ser Thr Leu Ser Gly Gly
130                 135                 140 gac aat gaa tct gaa aac agc gat gtg gat att ggc gaa cct gat acc      480
Asp Asn Glu Ser Glu Asn Ser Asp Val Asp Ile Gly Glu Pro Asp Thr
145                 150                 155                 160 gag gga tat gct atc act gac cgg gga tct gct ccc atc tct atg ggg      528
Glu Gly Tyr Ala Ile Thr Asp Arg Gly Ser Ala Pro Ile Ser Met Gly
                165                 170                 175 ttc agg gct tct gat gtt gaa act gca gaa gga ggg gag atc cac gag      576
Phe Arg Ala Ser Asp Val Glu Thr Ala Glu Gly Gly Glu Ile His Glu
            180                 185                 190 ctc ctg aga ctc caa tcc aga ggc aac aac ttt ccg aag ctt ggg aaa      624
Leu Leu Arg Leu Gln Ser Arg Gly Asn Asn Phe Pro Lys Leu Gly Lys
        195                 200                 205 act ctc aat gtt cct ccg ccc ccg gac ccc ggt agg gcc agc act tcc      672
Thr Leu Asn Val Pro Pro Pro Pro Asp Pro Gly Arg Ala Ser Thr Ser
    210                 215                 220 ggg aca ccc att aaa aag ggc aca gac gcg aga tta gcc tca ttt gga      720
Gly Thr Pro Ile Lys Lys Gly Thr Asp Ala Arg Leu Ala Ser Phe Gly
225                 230                 235                 240 acg gag atc gcg tct tta ttg aca ggt ggt gca acc caa tgt gct cga      768
Thr Glu Ile Ala Ser Leu Leu Thr Gly Gly Ala Thr Gln Cys Ala Arg
                245                 250                 255 aag tca ccc tcg gaa cca tca ggg cca ggt gca cct gcg ggg aat gtc      816
Lys Ser Pro Ser Glu Pro Ser Gly Pro Gly Ala Pro Ala Gly Asn Val
            260                 265                 270 ccc gag tgt gtg agc aat gcc gca ctg ata cag gag tgg aca ccc gaa      864
Pro Glu Cys Val Ser Asn Ala Ala Leu Ile Gln Glu Trp Thr Pro Glu
        275                 280                 285 tct ggt acc aca atc tcc ccg aga tcc cag aat aat gaa gaa ggg gga      912
Ser Gly Thr Thr Ile Ser Pro Arg Ser Gln Asn Asn Glu Glu Gly Gly
    290                 295                 300 gac tat tat gat gat gag ctg ttc tct gat gtc caa gat att aaa aca      960
Asp Tyr Tyr Asp Asp Glu Leu Phe Ser Asp Val Gln Asp Ile Lys Thr
305                 310                 315                 320 gcc ttg gcc aaa ata cac gag gat aat cag aag ata atc tcc aag cta     1008
Ala Leu Ala Lys Ile His Glu Asp Asn Gln Lys Ile Ile Ser Lys Leu
                325                 330                 335 gaa tca ctg ctg tta ttg aag gga gaa gtt gag tca att aag aag cag     1056
```

```
Glu Ser Leu Leu Leu Lys Gly Glu Val Glu Ser Ile Lys Lys Gln
                340                 345                 350 atc aac agg caa aat atc agc ata tcc acc ctg gaa gga cac ctc tca      1104
Ile Asn Arg Gln Asn Ile Ser Ile Ser Thr Leu Glu Gly His Leu Ser
                355                 360                 365 agc atc atg atc gcc att cct gga ctt ggg aag gat ccc aac gac ccc      1152
Ser Ile Met Ile Ala Ile Pro Gly Leu Gly Lys Asp Pro Asn Asp Pro
            370                 375                 380 act gca gat gtc gaa atc aat ccc gac ttg aaa ccc atc ata ggc aga      1200
Thr Ala Asp Val Glu Ile Asn Pro Asp Leu Lys Pro Ile Ile Gly Arg
385                 390                 395                 400 gat tca ggc cga gca ctg gcc gaa gtt ctc aag aaa ccc gtt gcc agc      1248
Asp Ser Gly Arg Ala Leu Ala Glu Val Leu Lys Lys Pro Val Ala Ser
                405                 410                 415 cga caa ctc caa gga atg aca aat gga cgg acc agt tcc aga gga cag      1296
Arg Gln Leu Gln Gly Met Thr Asn Gly Arg Thr Ser Ser Arg Gly Gln
            420                 425                 430 ctg ctg aag gaa ttt cag cta aag ccg atc ggg aaa aag atg agc tca      1344
Leu Leu Lys Glu Phe Gln Leu Lys Pro Ile Gly Lys Lys Met Ser Ser
        435                 440                 445 gcc gtc ggg ttt gtt cct gac acc ggc cct gca tca cgc agt gta atc      1392
Ala Val Gly Phe Val Pro Asp Thr Gly Pro Ala Ser Arg Ser Val Ile
450                 455                 460 cgc tcc att ata aaa tcc agc cgg cta gag gag gat cgg aag cgt tac      1440
Arg Ser Ile Ile Lys Ser Ser Arg Leu Glu Glu Asp Arg Lys Arg Tyr
465                 470                 475                 480 ctg atg act ctc ctt gat gat atc aaa gga gcc aat gat ctt gcc aag      1488
Leu Met Thr Leu Leu Asp Asp Ile Lys Gly Ala Asn Asp Leu Ala Lys
                485                 490                 495 ttc cac cag atg ctg atg aag ata ata atg aag tag                      1524
Phe His Gln Met Leu Met Lys Ile Ile Met Lys
            500                 505

<210> SEQ ID NO 15
<211> LENGTH: 507
<212> TYPE: PRT
<213> ORGANISM: Measles virus

<400> SEQUENCE: 15

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
                20                  25                  30

Met Ala Ala Trp Ser Glu Ile Ser Asp Asn Pro Gly Gln Glu Arg Ala
            35                  40                  45

Thr Cys Arg Glu Glu Lys Ala Gly Ser Ser Gly Leu Ser Lys Pro Cys
        50                  55                  60

Leu Ser Ala Ile Gly Ser Thr Glu Gly Gly Ala Pro Arg Ile Arg Gly
65                  70                  75                  80

Gln Gly Pro Gly Glu Ser Asp Asp Ala Glu Thr Leu Gly Ile Pro Pro
                85                  90                  95

Pro Arg Asn Leu Gln Ala Ser Ser Thr Gly Leu Gln Cys Tyr Tyr Val
            100                 105                 110

Tyr Asp His Ser Gly Glu Ala Val Lys Gly Ile Gln Asp Ala Asp Ser
        115                 120                 125

Ile Met Val Gln Ser Gly Leu Asp Gly Asp Ser Thr Leu Ser Gly Gly
    130                 135                 140

Asp Asn Glu Ser Glu Asn Ser Asp Val Asp Ile Gly Glu Pro Asp Thr
```

```
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Arg Leu Gln Ser Arg Gly Asn Asn Phe Pro Lys Leu Gly Lys
        195                 200                 205

Thr Leu Asn Val Pro Pro Pro Pro Asp Pro Gly Arg Ala Ser Thr Ser
    210                 215                 220

Gly Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
        275                 280                 285

Ser Gly Thr Thr Ile Ser Pro Arg Ser Gln Asn Asn Glu Glu Gly Gly
    290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                325                 330                 335

Glu Ser Leu Leu Leu Leu Lys Gly Glu Val Glu Ser Ile Lys Lys Gln
            340                 345                 350

Ile Asn Arg Gln Asn Ile Ser Ile Ser Thr Leu Glu Gly His Leu Ser
        355                 360                 365

Ser Ile Met Ile Ala Ile Pro Gly Leu Gly Lys Asp Pro Asn Asp Pro
    370                 375                 380

Thr Ala Asp Val Glu Ile Asn Pro Asp Leu Lys Pro Ile Ile Gly Arg
385                 390                 395                 400

Asp Ser Gly Arg Ala Leu Ala Glu Val Leu Lys Lys Pro Val Ala Ser
                405                 410                 415

Arg Gln Leu Gln Gly Met Thr Asn Gly Arg Thr Ser Ser Arg Gly Gln
            420                 425                 430

Leu Leu Lys Glu Phe Gln Leu Lys Pro Ile Gly Lys Lys Met Ser Ser
        435                 440                 445

Ala Val Gly Phe Val Pro Asp Thr Gly Pro Ala Ser Arg Ser Val Ile
    450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
                485                 490                 495

Phe His Gln Met Leu Met Lys Ile Ile Met Lys
            500                 505
```

<210> SEQ ID NO 16
<211> LENGTH: 6552
<212> TYPE: DNA
<213> ORGANISM: Measles virus
<220> FEATURE:
<221> NAME/KEY: CDS
<222> LOCATION: (1)..(6552)
<220> FEATURE:
<221> NAME/KEY: misc_feature
<222> LOCATION: (1)..(6555)

<223> OTHER INFORMATION: Schwarz MV L gene

<400> SEQUENCE: 16

```
atg gac tcg cta tct gtc aac cag atc tta tac cct gaa gtt cac cta      48
Met Asp Ser Leu Ser Val Asn Gln Ile Leu Tyr Pro Glu Val His Leu
1               5                   10                  15 gat agc ccg ata gtt acc aat aag ata gta gcc atc ctg gag tat gct      96
Asp Ser Pro Ile Val Thr Asn Lys Ile Val Ala Ile Leu Glu Tyr Ala
            20                  25                  30 cga gtc cct cac gct tac agc ctg gag gac cct aca ctg tgt cag aac     144
Arg Val Pro His Ala Tyr Ser Leu Glu Asp Pro Thr Leu Cys Gln Asn
        35                  40                  45 atc aag cac cgc cta aaa aac gga ttt tcc aac caa atg att ata aac     192
Ile Lys His Arg Leu Lys Asn Gly Phe Ser Asn Gln Met Ile Ile Asn
    50                  55                  60 aat gtg gaa gtt ggg aat gtc atc aag tcc aag ctt agg agt tat ccg     240
Asn Val Glu Val Gly Asn Val Ile Lys Ser Lys Leu Arg Ser Tyr Pro
65                  70                  75                  80 gcc cac tct cat att cca tat cca aat tgt aat cag gat tta ttt aac     288
Ala His Ser His Ile Pro Tyr Pro Asn Cys Asn Gln Asp Leu Phe Asn
                85                  90                  95 ata gaa gac aaa gag tca acg agg aag atc cgt gaa ctc ctc aaa aag     336
Ile Glu Asp Lys Glu Ser Thr Arg Lys Ile Arg Glu Leu Leu Lys Lys
            100                 105                 110 ggg aat tcg ctg tac tcc aaa gtc agt gat aag gtt ttc caa tgc tta     384
Gly Asn Ser Leu Tyr Ser Lys Val Ser Asp Lys Val Phe Gln Cys Leu
        115                 120                 125 agg gac act aac tca cgg ctt ggc cta ggc tcc gaa ttg agg gag gac     432
Arg Asp Thr Asn Ser Arg Leu Gly Leu Gly Ser Glu Leu Arg Glu Asp
    130                 135                 140 atc aag gag aaa gtt att aac ttg gga gtt tac atg cac agc tcc cag     480
Ile Lys Glu Lys Val Ile Asn Leu Gly Val Tyr Met His Ser Ser Gln
145                 150                 155                 160 tgg ttt gag ccc ttt ctg ttt tgg ttt aca gtc aag act gag atg agg     528
Trp Phe Glu Pro Phe Leu Phe Trp Phe Thr Val Lys Thr Glu Met Arg
                165                 170                 175 tca gtg att aaa tca caa acc cat act tgc cat agg agg aga cac aca     576
Ser Val Ile Lys Ser Gln Thr His Thr Cys His Arg Arg Arg His Thr
            180                 185                 190 cct gta ttc ttc act ggt agt tca gtt gag ttg cta atc tct cgt gac     624
Pro Val Phe Phe Thr Gly Ser Ser Val Glu Leu Leu Ile Ser Arg Asp
        195                 200                 205 ctt gtt gct ata atc agt aaa gag tct caa cat gta tat tac ctg aca     672
Leu Val Ala Ile Ile Ser Lys Glu Ser Gln His Val Tyr Tyr Leu Thr
    210                 215                 220 ttt gaa ctg gtt ttg atg tat tgt gat gtc ata gag ggg agg tta atg     720
Phe Glu Leu Val Leu Met Tyr Cys Asp Val Ile Glu Gly Arg Leu Met
225                 230                 235                 240 aca gag acc gct atg act att gat gct agg tat aca gag ctt cta gga     768
Thr Glu Thr Ala Met Thr Ile Asp Ala Arg Tyr Thr Glu Leu Leu Gly
                245                 250                 255 aga gtc aga tac atg tgg aaa ctg ata gat ggt ttc ttc cct gca ctc     816
Arg Val Arg Tyr Met Trp Lys Leu Ile Asp Gly Phe Phe Pro Ala Leu
            260                 265                 270 ggg aat cca act tat caa att gta gcc atg ctg gag cct ctt tca ctt     864
Gly Asn Pro Thr Tyr Gln Ile Val Ala Met Leu Glu Pro Leu Ser Leu
        275                 280                 285 gct tac ctg cag ctg agg gat ata aca gta gaa ctc aga ggt gct ttc     912
Ala Tyr Leu Gln Leu Arg Asp Ile Thr Val Glu Leu Arg Gly Ala Phe
    290                 295                 300
```

-continued

```
ctt aac cac tgc ttt act gaa ata cat gat gtt ctt gac caa aac ggg       960
Leu Asn His Cys Phe Thr Glu Ile His Asp Val Leu Asp Gln Asn Gly
305                 310                 315                 320 ttt tct gat gaa ggt act tat cat gag tta act gaa gct cta gat tac      1008
Phe Ser Asp Glu Gly Thr Tyr His Glu Leu Thr Glu Ala Leu Asp Tyr
                325                 330                 335 att ttc ata act gat gac ata cat ctg aca ggg gag att ttc tca ttt      1056
Ile Phe Ile Thr Asp Asp Ile His Leu Thr Gly Glu Ile Phe Ser Phe
            340                 345                 350 ttc aga agt ttc ggc cac ccc aga ctt gaa gca gta acg gct gct gaa      1104
Phe Arg Ser Phe Gly His Pro Arg Leu Glu Ala Val Thr Ala Ala Glu
        355                 360                 365 aat gtt agg aaa tac atg aat cag cct aaa gtc att gtg tat gag act      1152
Asn Val Arg Lys Tyr Met Asn Gln Pro Lys Val Ile Val Tyr Glu Thr
    370                 375                 380 ctg atg aaa ggt cat gcc ata ttt tgt gga atc ata atc aac ggc tat      1200
Leu Met Lys Gly His Ala Ile Phe Cys Gly Ile Ile Ile Asn Gly Tyr
385                 390                 395                 400 cgt gac agg cac gga ggc agt tgg cca ccg ctg acc ctc ccc ctg cat      1248
Arg Asp Arg His Gly Gly Ser Trp Pro Pro Leu Thr Leu Pro Leu His
                405                 410                 415 gct gca gac aca atc cgg aat gct caa gct tca ggt gaa ggg tta aca      1296
Ala Ala Asp Thr Ile Arg Asn Ala Gln Ala Ser Gly Glu Gly Leu Thr
            420                 425                 430 cat gag cag tgc gtt gat aac tgg aaa tct ttt gct gga gtg aaa ttt      1344
His Glu Gln Cys Val Asp Asn Trp Lys Ser Phe Ala Gly Val Lys Phe
        435                 440                 445 ggc tgc ttt atg cct ctt agc ctg gat agt gat ctg aca atg tac cta      1392
Gly Cys Phe Met Pro Leu Ser Leu Asp Ser Asp Leu Thr Met Tyr Leu
    450                 455                 460 aag gac aag gca ctt gct gct ctc caa agg gaa tgg gat tca gtt tac      1440
Lys Asp Lys Ala Leu Ala Ala Leu Gln Arg Glu Trp Asp Ser Val Tyr
465                 470                 475                 480 ccg aaa gag ttc ctg cgt tac gac cct ccc aag gga acc ggg tca cgg      1488
Pro Lys Glu Phe Leu Arg Tyr Asp Pro Pro Lys Gly Thr Gly Ser Arg
                485                 490                 495 agg ctt gta gat gtt ttc ctt aat gat tcg agc ttt gac cca tat gat      1536
Arg Leu Val Asp Val Phe Leu Asn Asp Ser Ser Phe Asp Pro Tyr Asp
            500                 505                 510 gtg ata atg tat gtt gta agt gga gct tac ctc cat gac cct gag ttc      1584
Val Ile Met Tyr Val Val Ser Gly Ala Tyr Leu His Asp Pro Glu Phe
        515                 520                 525 aac ctg tct tac agc ctg aaa gaa aag gag atc aag gaa aca ggt aga      1632
Asn Leu Ser Tyr Ser Leu Lys Glu Lys Glu Ile Lys Glu Thr Gly Arg
    530                 535                 540 ctt ttt gct aaa atg act tac aaa atg agg gca tgc caa gtg att gct      1680
Leu Phe Ala Lys Met Thr Tyr Lys Met Arg Ala Cys Gln Val Ile Ala
545                 550                 555                 560 gaa aat cta atc tca aac ggg att ggc aaa tat ttt aag gac aat ggg      1728
Glu Asn Leu Ile Ser Asn Gly Ile Gly Lys Tyr Phe Lys Asp Asn Gly
                565                 570                 575 atg gcc aag gat gag cac gat ttg act aag gca ctc cac act cta gct      1776
Met Ala Lys Asp Glu His Asp Leu Thr Lys Ala Leu His Thr Leu Ala
            580                 585                 590 gtc tca gga gtc ccc aaa gat ctc aaa gaa agt cac agg ggg gga cca      1824
Val Ser Gly Val Pro Lys Asp Leu Lys Glu Ser His Arg Gly Gly Pro
        595                 600                 605 gtc tta aaa acc tac tcc cga agc cca gtc cac aca agt acc agg aac      1872
Val Leu Lys Thr Tyr Ser Arg Ser Pro Val His Thr Ser Thr Arg Asn
```

```
                610                 615                 620
gtg aga gca gca aaa ggg ttt ata ggg ttc cct caa gta att cgg cag     1920
Val Arg Ala Ala Lys Gly Phe Ile Gly Phe Pro Gln Val Ile Arg Gln
625                 630                 635                 640 gac caa gac act gat cat ccg gag aat atg gaa gct tac gag aca gtc     1968
Asp Gln Asp Thr Asp His Pro Glu Asn Met Glu Ala Tyr Glu Thr Val
                    645                 650                 655 agt gca ttt atc acg act gat ctc aag aag tac tgc ctt aat tgg aga     2016
Ser Ala Phe Ile Thr Thr Asp Leu Lys Lys Tyr Cys Leu Asn Trp Arg
                660                 665                 670 tat gag acc atc agc ttg ttt gca cag agg cta aat gag att tac gga     2064
Tyr Glu Thr Ile Ser Leu Phe Ala Gln Arg Leu Asn Glu Ile Tyr Gly
675                 680                 685 ttg ccc tca ttt ttc cag tgg ctg cat aag agg ctt gag acc tct gtc     2112
Leu Pro Ser Phe Phe Gln Trp Leu His Lys Arg Leu Glu Thr Ser Val
690                 695                 700 ctg tat gta agt gac cct cat tgc ccc ccc gac ctt gac gcc cat atc     2160
Leu Tyr Val Ser Asp Pro His Cys Pro Pro Asp Leu Asp Ala His Ile
705                 710                 715                 720 ccg tta tat aaa gtc ccc aat gat caa atc ttc att aag tac cct atg     2208
Pro Leu Tyr Lys Val Pro Asn Asp Gln Ile Phe Ile Lys Tyr Pro Met
                725                 730                 735 gga ggt ata gaa ggg tat tgt cag aag ctg tgg acc atc agc acc att     2256
Gly Gly Ile Glu Gly Tyr Cys Gln Lys Leu Trp Thr Ile Ser Thr Ile
                740                 745                 750 ccc tat cta tac ctg gct gct tat gag agc gga gta agg att gct tcg     2304
Pro Tyr Leu Tyr Leu Ala Ala Tyr Glu Ser Gly Val Arg Ile Ala Ser
                755                 760                 765 tta gtg caa ggg gac aat cag acc ata gcc gta aca aaa agg gta ccc     2352
Leu Val Gln Gly Asp Asn Gln Thr Ile Ala Val Thr Lys Arg Val Pro
770                 775                 780 agc aca tgg ccc tac aac ctt aag aaa cgg gaa gct gct aga gta act     2400
Ser Thr Trp Pro Tyr Asn Leu Lys Lys Arg Glu Ala Ala Arg Val Thr
785                 790                 795                 800 aga gat tac ttt gta att ctt agg caa agg cta cat gat att ggc cat     2448
Arg Asp Tyr Phe Val Ile Leu Arg Gln Arg Leu His Asp Ile Gly His
                805                 810                 815 cac ctc aag gca aat gag aca att gtt tca tca cat ttt ttt gtc tat     2496
His Leu Lys Ala Asn Glu Thr Ile Val Ser Ser His Phe Phe Val Tyr
                820                 825                 830 tca aaa gga ata tat tat gat ggg cta ctt gtg tcc caa tca ctc aag     2544
Ser Lys Gly Ile Tyr Tyr Asp Gly Leu Leu Val Ser Gln Ser Leu Lys
            835                 840                 845 agc atc gca aga tgt gta ttc tgg tca gag act ata gtt gat gaa aca     2592
Ser Ile Ala Arg Cys Val Phe Trp Ser Glu Thr Ile Val Asp Glu Thr
850                 855                 860 agg gca gca tgc agt aat att gct aca aca atg gct aaa agc atc gag     2640
Arg Ala Ala Cys Ser Asn Ile Ala Thr Thr Met Ala Lys Ser Ile Glu
865                 870                 875                 880 aga ggt tat gac cgt tac ctt gca tat tcc ctg aac gtc cta aaa gtg     2688
Arg Gly Tyr Asp Arg Tyr Leu Ala Tyr Ser Leu Asn Val Leu Lys Val
                885                 890                 895 ata cag caa att ctg atc tct ctt ggc ttc aca atc aat tca acc atg     2736
Ile Gln Gln Ile Leu Ile Ser Leu Gly Phe Thr Ile Asn Ser Thr Met
            900                 905                 910 acc cgg gat gta gtc ata ccc ctc ctc aca aac aac gac ctc tta ata     2784
Thr Arg Asp Val Val Ile Pro Leu Leu Thr Asn Asn Asp Leu Leu Ile
            915                 920                 925 agg atg gca ctg ttg ccc gct cct att ggg ggg atg aat tat ctg aat     2832
```

```
                                         -continued

Arg Met Ala Leu Leu Pro Ala Pro Ile Gly Gly Met Asn Tyr Leu Asn
    930                 935                 940 atg agc agg ctg ttt gtc aga aac atc ggt gat cca gta aca tca tca      2880
Met Ser Arg Leu Phe Val Arg Asn Ile Gly Asp Pro Val Thr Ser Ser
945                 950                 955                 960 att gct gat ctc aag aga atg att ctc gcc tca cta atg cct gaa gag      2928
Ile Ala Asp Leu Lys Arg Met Ile Leu Ala Ser Leu Met Pro Glu Glu
                965                 970                 975 acc ctc cat caa gta atg aca caa caa ccg ggg gac tct tca ttc cta      2976
Thr Leu His Gln Val Met Thr Gln Gln Pro Gly Asp Ser Ser Phe Leu
            980                 985                 990 gac tgg gct agc gac cct tac tca gca aat ctt gta tgt gtc cag agc      3024
Asp Trp Ala Ser Asp Pro Tyr Ser Ala Asn Leu Val Cys Val Gln Ser
        995                 1000                1005 atc act aga ctc ctc aag aac ata act gca agg ttt gtc ctg atc          3069
Ile Thr Arg Leu Leu Lys Asn Ile Thr Ala Arg Phe Val Leu Ile
    1010                1015                1020 cat agt cca aac cca atg tta aaa gga tta ttc cat gat gac agt          3114
His Ser Pro Asn Pro Met Leu Lys Gly Leu Phe His Asp Asp Ser
    1025                1030                1035 aaa gaa gag gac gag gga ctg gcg gca ttc ctc atg gac agg cat          3159
Lys Glu Glu Asp Glu Gly Leu Ala Ala Phe Leu Met Asp Arg His
    1040                1045                1050 att ata gta cct agg gca gct cat gaa atc ctg gat cat agt gtc          3204
Ile Ile Val Pro Arg Ala Ala His Glu Ile Leu Asp His Ser Val
    1055                1060                1065 aca ggg gca aga gag tct att gca ggc atg ctg gat acc aca aaa          3249
Thr Gly Ala Arg Glu Ser Ile Ala Gly Met Leu Asp Thr Thr Lys
    1070                1075                1080 ggc ttg att cga gcc agc atg agg aag ggg gga tta acc tct cga          3294
Gly Leu Ile Arg Ala Ser Met Arg Lys Gly Gly Leu Thr Ser Arg
    1085                1090                1095 gtg ata acc aga ttg tcc aat tat gac tat gaa caa ttc aga gca          3339
Val Ile Thr Arg Leu Ser Asn Tyr Asp Tyr Glu Gln Phe Arg Ala
    1100                1105                1110 ggg atg gtg cta ttg aca gga aga aag aga aat gtc ctc att gac          3384
Gly Met Val Leu Leu Thr Gly Arg Lys Arg Asn Val Leu Ile Asp
    1115                1120                1125 aaa gag tca tgt tca gtg cag ctg gcg aga gct cta aga agc cat          3429
Lys Glu Ser Cys Ser Val Gln Leu Ala Arg Ala Leu Arg Ser His
    1130                1135                1140 atg tgg gcg agg cta gct cga gga cgg cct att tac ggc ctt gag          3474
Met Trp Ala Arg Leu Ala Arg Gly Arg Pro Ile Tyr Gly Leu Glu
    1145                1150                1155 gtc cct gat gta cta gaa tct atg cga ggc cac ctt att cgg cgt          3519
Val Pro Asp Val Leu Glu Ser Met Arg Gly His Leu Ile Arg Arg
    1160                1165                1170 cat gag aca tgt gtc atc tgc gag tgt gga tca gtc aac tac gga          3564
His Glu Thr Cys Val Ile Cys Glu Cys Gly Ser Val Asn Tyr Gly
    1175                1180                1185 tgg ttt ttt gtc ccc tcg ggt tgc caa ctg gat gat att gac aag          3609
Trp Phe Phe Val Pro Ser Gly Cys Gln Leu Asp Asp Ile Asp Lys
    1190                1195                1200 gaa aca tca tcc ttg aga gtc cca tat att ggt tct acc act gat          3654
Glu Thr Ser Ser Leu Arg Val Pro Tyr Ile Gly Ser Thr Thr Asp
    1205                1210                1215 gag aga aca gac atg aag ctt gcc ttc gta aga gcc cca agt cga          3699
Glu Arg Thr Asp Met Lys Leu Ala Phe Val Arg Ala Pro Ser Arg
    1220                1225                1230
```

-continued

| | | | | | | | | | | | | |
|---|---|---|---|---|---|---|---|---|---|---|---|---|
| tcc | ttg | cga | tct | gct | gtt | aga | ata | gca | aca | gtg | tac | tca | tgg | gct | 3744 |
| Ser | Leu | Arg | Ser | Ala | Val | Arg | Ile | Ala | Thr | Val | Tyr | Ser | Trp | Ala | |
| 1235 | | | | | 1240 | | | | | 1245 | | | | | |

| tac | ggt | gat | gat | gat | agc | tct | tgg | aac | gaa | gcc | tgg | ttg | ttg | gct | 3789 |
| Tyr | Gly | Asp | Asp | Asp | Ser | Ser | Trp | Asn | Glu | Ala | Trp | Leu | Leu | Ala | |
| 1250 | | | | | 1255 | | | | | 1260 | | | | | |

| agg | caa | agg | gcc | aat | gtg | agc | ctg | gag | gag | cta | agg | gtg | atc | act | 3834 |
| Arg | Gln | Arg | Ala | Asn | Val | Ser | Leu | Glu | Glu | Leu | Arg | Val | Ile | Thr | |
| 1265 | | | | | 1270 | | | | | 1275 | | | | | |

| ccc | atc | tca | act | tcg | act | aat | tta | gcg | cat | agg | ttg | agg | gat | cgt | 3879 |
| Pro | Ile | Ser | Thr | Ser | Thr | Asn | Leu | Ala | His | Arg | Leu | Arg | Asp | Arg | |
| 1280 | | | | | 1285 | | | | | 1290 | | | | | |

| agc | act | caa | gtg | aaa | tac | tca | ggt | aca | tcc | ctt | gtc | cga | gtg | gcg | 3924 |
| Ser | Thr | Gln | Val | Lys | Tyr | Ser | Gly | Thr | Ser | Leu | Val | Arg | Val | Ala | |
| 1295 | | | | | 1300 | | | | | 1305 | | | | | |

| agg | tat | acc | aca | atc | tcc | aac | gac | aat | ctc | tca | ttt | gtc | ata | tca | 3969 |
| Arg | Tyr | Thr | Thr | Ile | Ser | Asn | Asp | Asn | Leu | Ser | Phe | Val | Ile | Ser | |
| 1310 | | | | | 1315 | | | | | 1320 | | | | | |

| gat | aag | aag | gtt | gat | act | aac | ttt | ata | tac | caa | caa | gga | atg | ctt | 4014 |
| Asp | Lys | Lys | Val | Asp | Thr | Asn | Phe | Ile | Tyr | Gln | Gln | Gly | Met | Leu | |
| 1325 | | | | | 1330 | | | | | 1335 | | | | | |

| cta | ggg | ttg | ggt | gtt | tta | gaa | aca | ttg | ttt | cga | ctc | gag | aaa | gat | 4059 |
| Leu | Gly | Leu | Gly | Val | Leu | Glu | Thr | Leu | Phe | Arg | Leu | Glu | Lys | Asp | |
| 1340 | | | | | 1345 | | | | | 1350 | | | | | |

| acc | gga | tca | tct | aac | acg | gta | tta | cat | ctt | cac | gtc | gaa | aca | gat | 4104 |
| Thr | Gly | Ser | Ser | Asn | Thr | Val | Leu | His | Leu | His | Val | Glu | Thr | Asp | |
| 1355 | | | | | 1360 | | | | | 1365 | | | | | |

| tgt | tgc | gtg | atc | ccg | atg | ata | gat | cat | ccc | agg | ata | ccc | agc | tcc | 4149 |
| Cys | Cys | Val | Ile | Pro | Met | Ile | Asp | His | Pro | Arg | Ile | Pro | Ser | Ser | |
| 1370 | | | | | 1375 | | | | | 1380 | | | | | |

| cgc | aag | cta | gag | ctg | agg | gca | gag | cta | tgt | acc | aac | cca | ttg | ata | 4194 |
| Arg | Lys | Leu | Glu | Leu | Arg | Ala | Glu | Leu | Cys | Thr | Asn | Pro | Leu | Ile | |
| 1385 | | | | | 1390 | | | | | 1395 | | | | | |

| tat | gat | aat | gca | cct | tta | att | gac | aga | gat | gca | aca | agg | cta | tac | 4239 |
| Tyr | Asp | Asn | Ala | Pro | Leu | Ile | Asp | Arg | Asp | Ala | Thr | Arg | Leu | Tyr | |
| 1400 | | | | | 1405 | | | | | 1410 | | | | | |

| acc | cag | agc | cat | agg | agg | cac | ctt | gtg | gaa | ttt | gtt | aca | tgg | tcc | 4284 |
| Thr | Gln | Ser | His | Arg | Arg | His | Leu | Val | Glu | Phe | Val | Thr | Trp | Ser | |
| 1415 | | | | | 1420 | | | | | 1425 | | | | | |

| aca | ccc | caa | cta | tat | cac | att | tta | gct | aag | tcc | aca | gca | cta | tct | 4329 |
| Thr | Pro | Gln | Leu | Tyr | His | Ile | Leu | Ala | Lys | Ser | Thr | Ala | Leu | Ser | |
| 1430 | | | | | 1435 | | | | | 1440 | | | | | |

| atg | att | gac | ctg | gta | aca | aaa | ttt | gag | aag | gac | cat | atg | aat | gaa | 4374 |
| Met | Ile | Asp | Leu | Val | Thr | Lys | Phe | Glu | Lys | Asp | His | Met | Asn | Glu | |
| 1445 | | | | | 1450 | | | | | 1455 | | | | | |

| att | tca | gct | ctc | ata | ggg | gat | gac | gat | atc | aat | agt | ttc | ata | act | 4419 |
| Ile | Ser | Ala | Leu | Ile | Gly | Asp | Asp | Asp | Ile | Asn | Ser | Phe | Ile | Thr | |
| 1460 | | | | | 1465 | | | | | 1470 | | | | | |

| gag | ttt | ctg | ctc | ata | gag | cca | aga | tta | ttc | act | atc | tac | ttg | ggc | 4464 |
| Glu | Phe | Leu | Leu | Ile | Glu | Pro | Arg | Leu | Phe | Thr | Ile | Tyr | Leu | Gly | |
| 1475 | | | | | 1480 | | | | | 1485 | | | | | |

| cag | tgt | gcg | gcc | atc | aat | tgg | gca | ttt | gat | gta | cat | tat | cat | aga | 4509 |
| Gln | Cys | Ala | Ala | Ile | Asn | Trp | Ala | Phe | Asp | Val | His | Tyr | His | Arg | |
| 1490 | | | | | 1495 | | | | | 1500 | | | | | |

| cca | tca | ggg | aaa | tat | cag | atg | ggt | gag | ctg | ttg | tca | tcg | ttc | ctt | 4554 |
| Pro | Ser | Gly | Lys | Tyr | Gln | Met | Gly | Glu | Leu | Leu | Ser | Ser | Phe | Leu | |
| 1505 | | | | | 1510 | | | | | 1515 | | | | | |

| tct | aga | atg | agc | aaa | gga | gtg | ttt | aag | gtg | ctt | gtc | aat | gct | cta | 4599 |
| Ser | Arg | Met | Ser | Lys | Gly | Val | Phe | Lys | Val | Leu | Val | Asn | Ala | Leu | |
| 1520 | | | | | 1525 | | | | | 1530 | | | | | |

| | | | | | | | | | | | |
|---|---|---|---|---|---|---|---|---|---|---|---|
| agc | cac | cca | aag | atc | tac | aag | aaa | ttc | tgg | cat | tgt | ggt | att | ata | 4644 |
| Ser | His | Pro | Lys | Ile | Tyr | Lys | Lys | Phe | Trp | His | Cys | Gly | Ile | Ile | |
| | 1535 | | | | 1540 | | | | | 1545 | | | | | |

```
agc cac cca aag atc tac aag aaa ttc tgg cat tgt ggt att ata      4644
Ser His Pro Lys Ile Tyr Lys Lys Phe Trp His Cys Gly Ile Ile
    1535            1540                1545 gag cct atc cat ggt cct tca ctt gat gct caa aac ttg cac aca      4689
Glu Pro Ile His Gly Pro Ser Leu Asp Ala Gln Asn Leu His Thr
1550            1555                1560 act gtg tgc aac atg gtt tac aca tgc tat atg acc tac ctc gac      4734
Thr Val Cys Asn Met Val Tyr Thr Cys Tyr Met Thr Tyr Leu Asp
    1565            1570                1575 ctg ttg ttg aat gaa gag tta gaa gag ttc aca ttt ctc ttg tgt      4779
Leu Leu Leu Asn Glu Glu Leu Glu Glu Phe Thr Phe Leu Leu Cys
1580            1585                1590 gaa agc gac gag gat gta gta ccg gac aga ttc gac aac atc cag      4824
Glu Ser Asp Glu Asp Val Val Pro Asp Arg Phe Asp Asn Ile Gln
    1595            1600                1605 gca aaa cac tta tgt gtt ctg gca gat ttg tac tgt caa cca ggg      4869
Ala Lys His Leu Cys Val Leu Ala Asp Leu Tyr Cys Gln Pro Gly
1610            1615                1620 acc tgc cca cca att cga ggt cta aga ccg gta gag aaa tgt gca      4914
Thr Cys Pro Pro Ile Arg Gly Leu Arg Pro Val Glu Lys Cys Ala
    1625            1630                1635 gtt cta acc gac cat atc aag gca gag gct atg tta tct cca gca      4959
Val Leu Thr Asp His Ile Lys Ala Glu Ala Met Leu Ser Pro Ala
1640            1645                1650 gga tct tcg tgg aac ata aat cca att att gta gac cat tac tca      5004
Gly Ser Ser Trp Asn Ile Asn Pro Ile Ile Val Asp His Tyr Ser
    1655            1660                1665 tgc tct ctg act tat ctc cgg cga gga tcg atc aaa cag ata aga      5049
Cys Ser Leu Thr Tyr Leu Arg Arg Gly Ser Ile Lys Gln Ile Arg
1670            1675                1680 ttg aga gtt gat cca gga ttc att ttc gac gcc ctc gct gag gta      5094
Leu Arg Val Asp Pro Gly Phe Ile Phe Asp Ala Leu Ala Glu Val
    1685            1690                1695 aat gtc agt cag cca aag atc ggc agc aac aac atc tca aat atg      5139
Asn Val Ser Gln Pro Lys Ile Gly Ser Asn Asn Ile Ser Asn Met
1700            1705                1710 agc atc aag gct ttc aga ccc cca cac gat gat gtt gca aaa ttg      5184
Ser Ile Lys Ala Phe Arg Pro Pro His Asp Asp Val Ala Lys Leu
    1715            1720                1725 ctc aaa gat atc aac aca agc aag cac aat ctt ccc att tca ggg      5229
Leu Lys Asp Ile Asn Thr Ser Lys His Asn Leu Pro Ile Ser Gly
1730            1735                1740 ggc aat ctc gcc aat tat gaa atc cat gct ttc cgc aga atc ggg      5274
Gly Asn Leu Ala Asn Tyr Glu Ile His Ala Phe Arg Arg Ile Gly
    1745            1750                1755 ttg aac tca tct gct tgc tac aaa gct gtt gag ata tca aca tta      5319
Leu Asn Ser Ser Ala Cys Tyr Lys Ala Val Glu Ile Ser Thr Leu
1760            1765                1770 att agg aga tgc ctt gag cca ggg gag gac ggc ttg ttc ttg ggt      5364
Ile Arg Arg Cys Leu Glu Pro Gly Glu Asp Gly Leu Phe Leu Gly
    1775            1780                1785 gag gga tcg ggt tct atg ttg atc act tat aaa gag ata ctt aaa      5409
Glu Gly Ser Gly Ser Met Leu Ile Thr Tyr Lys Glu Ile Leu Lys
1790            1795                1800 cta aac aag tgc ttc tat aat agt ggg gtt tcc gcc aat tct aga      5454
Leu Asn Lys Cys Phe Tyr Asn Ser Gly Val Ser Ala Asn Ser Arg
    1805            1810                1815 tct ggt caa agg gaa tta gca ccc tat ccc tcc gaa gtt ggc ctt      5499
Ser Gly Gln Arg Glu Leu Ala Pro Tyr Pro Ser Glu Val Gly Leu
```

```
                        1820                    1825                    1830
          gtc gaa cac aga atg gga gta ggt aat att gtc aaa gtg ctc ttt       5544
          Val Glu His Arg Met Gly Val Gly Asn Ile Val Lys Val Leu Phe
          1835                    1840                    1845 aac ggg agg ccc gaa gtc acg tgg gta ggc agt gta gat tgc ttc       5589
          Asn Gly Arg Pro Glu Val Thr Trp Val Gly Ser Val Asp Cys Phe
          1850                    1855                    1860 aat ttc ata gtt agt aat atc cct acc tct agt gtg ggg ttt atc       5634
          Asn Phe Ile Val Ser Asn Ile Pro Thr Ser Ser Val Gly Phe Ile
          1865                    1870                    1875 cat tca gat ata gag acc ttg cct gac aaa gat act ata gag aag       5679
          His Ser Asp Ile Glu Thr Leu Pro Asp Lys Asp Thr Ile Glu Lys
          1880                    1885                    1890 cta gag gaa ttg gca gcc atc tta tcg atg gct ctg ctc ctg ggc       5724
          Leu Glu Glu Leu Ala Ala Ile Leu Ser Met Ala Leu Leu Leu Gly
          1895                    1900                    1905 aaa ata gga tca ata ctg gtg att aag ctt atg cct ttc agc ggg       5769
          Lys Ile Gly Ser Ile Leu Val Ile Lys Leu Met Pro Phe Ser Gly
          1910                    1915                    1920 gat ttt gtt cag gga ttt ata agt tat gta ggg tct cat tat aga       5814
          Asp Phe Val Gln Gly Phe Ile Ser Tyr Val Gly Ser His Tyr Arg
          1925                    1930                    1935 gaa gtg aac ctt gta tac cct aga tac agc aac ttc atc tct act       5859
          Glu Val Asn Leu Val Tyr Pro Arg Tyr Ser Asn Phe Ile Ser Thr
          1940                    1945                    1950 gaa tct tat ttg gtt atg aca gat ctc aag gct aac cgg cta atg       5904
          Glu Ser Tyr Leu Val Met Thr Asp Leu Lys Ala Asn Arg Leu Met
          1955                    1960                    1965 aat cct gaa aag att aag cag cag ata att gaa tca tct gtg agg       5949
          Asn Pro Glu Lys Ile Lys Gln Gln Ile Ile Glu Ser Ser Val Arg
          1970                    1975                    1980 act tca cct gga ctt ata ggt cac atc cta tcc att aag caa cta       5994
          Thr Ser Pro Gly Leu Ile Gly His Ile Leu Ser Ile Lys Gln Leu
          1985                    1990                    1995 agc tgc ata caa gca att gtg gga gac gca gtt agt aga ggt gat       6039
          Ser Cys Ile Gln Ala Ile Val Gly Asp Ala Val Ser Arg Gly Asp
          2000                    2005                    2010 atc aat cct act ctg aaa aaa ctt aca cct ata gag cag gtg ctg       6084
          Ile Asn Pro Thr Leu Lys Lys Leu Thr Pro Ile Glu Gln Val Leu
          2015                    2020                    2025 atc aat tgc ggg ttg gca att aac gga cct aag ctg tgc aaa gaa       6129
          Ile Asn Cys Gly Leu Ala Ile Asn Gly Pro Lys Leu Cys Lys Glu
          2030                    2035                    2040 ttg atc cac cat gat gtt gcc tca ggg caa gat gga ttg ctt aat       6174
          Leu Ile His His Asp Val Ala Ser Gly Gln Asp Gly Leu Leu Asn
          2045                    2050                    2055 tct ata ctc atc ctc tac agg gag ttg gca aga ttc aaa gac aac       6219
          Ser Ile Leu Ile Leu Tyr Arg Glu Leu Ala Arg Phe Lys Asp Asn
          2060                    2065                    2070 caa aga agt caa caa ggg atg ttc cac gct tac ccc gta ttg gta       6264
          Gln Arg Ser Gln Gln Gly Met Phe His Ala Tyr Pro Val Leu Val
          2075                    2080                    2085 agt agc agg caa cga gaa ctt ata tct agg atc acc cgc aaa ttc       6309
          Ser Ser Arg Gln Arg Glu Leu Ile Ser Arg Ile Thr Arg Lys Phe
          2090                    2095                    2100 tgg ggg cac att ctt ctt tac tcc ggg aac aaa aag ttg ata aat       6354
          Trp Gly His Ile Leu Leu Tyr Ser Gly Asn Lys Lys Leu Ile Asn
          2105                    2110                    2115 aag ttt atc cag aat ctc aag tcc ggc tat ctg ata cta gac tta       6399
```

```
Lys Phe  Ile Gln Asn Leu Lys  Ser Gly Tyr Leu Ile  Leu Asp Leu
    2120                2125                2130 cac cag  aat atc ttc gtt aag  aat cta tcc aag tca  gag aaa cag      6444
His Gln  Asn Ile Phe Val Lys  Asn Leu Ser Lys Ser  Glu Lys Gln
    2135                2140                2145 att att  atg acg ggg ggt ttg  aaa cgt gag tgg gtt  ttt aag gta      6489
Ile Ile  Met Thr Gly Gly Leu  Lys Arg Glu Trp Val  Phe Lys Val
    2150                2155                2160 aca gtc  aag gag acc aaa gaa  tgg tat aag tta gtc  gga tac agt      6534
Thr Val  Lys Glu Thr Lys Glu  Trp Tyr Lys Leu Val  Gly Tyr Ser
    2165                2170                2175 gcc ctg  att aag gac taa                                            6552
Ala Leu  Ile Lys Asp
    2180

<210> SEQ ID NO 17
<211> LENGTH: 2183
<212> TYPE: PRT
<213> ORGANISM: Measles virus
<400> SEQUENCE: 17

Met Asp Ser Leu Ser Val Asn Gln Ile Leu Tyr Pro Glu Val His Leu
1               5                   10                  15

Asp Ser Pro Ile Val Thr Asn Lys Ile Val Ala Ile Leu Glu Tyr Ala
            20                  25                  30

Arg Val Pro His Ala Tyr Ser Leu Glu Asp Pro Thr Leu Cys Gln Asn
        35                  40                  45

Ile Lys His Arg Leu Lys Asn Gly Phe Ser Asn Gln Met Ile Ile Asn
    50                  55                  60

Asn Val Glu Val Gly Asn Val Ile Lys Ser Lys Leu Arg Ser Tyr Pro
65                  70                  75                  80

Ala His Ser His Ile Pro Tyr Pro Asn Cys Asn Gln Asp Leu Phe Asn
                85                  90                  95

Ile Glu Asp Lys Glu Ser Thr Arg Lys Ile Arg Glu Leu Leu Lys Lys
            100                 105                 110

Gly Asn Ser Leu Tyr Ser Lys Val Ser Asp Lys Val Phe Gln Cys Leu
        115                 120                 125

Arg Asp Thr Asn Ser Arg Leu Gly Leu Gly Ser Glu Leu Arg Glu Asp
    130                 135                 140

Ile Lys Glu Lys Val Ile Asn Leu Gly Val Tyr Met His Ser Ser Gln
145                 150                 155                 160

Trp Phe Glu Pro Phe Leu Phe Trp Phe Thr Val Lys Thr Glu Met Arg
                165                 170                 175

Ser Val Ile Lys Ser Gln Thr His Thr Cys His Arg Arg Arg His Thr
            180                 185                 190

Pro Val Phe Phe Thr Gly Ser Ser Val Glu Leu Leu Ile Ser Arg Asp
        195                 200                 205

Leu Val Ala Ile Ile Ser Lys Glu Ser Gln His Val Tyr Tyr Leu Thr
    210                 215                 220

Phe Glu Leu Val Leu Met Tyr Cys Asp Val Ile Glu Gly Arg Leu Met
225                 230                 235                 240

Thr Glu Thr Ala Met Thr Ile Asp Ala Arg Tyr Thr Glu Leu Leu Gly
                245                 250                 255

Arg Val Arg Tyr Met Trp Lys Leu Ile Asp Gly Phe Phe Pro Ala Leu
            260                 265                 270

Gly Asn Pro Thr Tyr Gln Ile Val Ala Met Leu Glu Pro Leu Ser Leu
```

```
            275                 280                 285
Ala Tyr Leu Gln Leu Arg Asp Ile Thr Val Glu Leu Arg Gly Ala Phe
290                 295                 300

Leu Asn His Cys Phe Thr Glu Ile His Asp Val Leu Asp Gln Asn Gly
305                 310                 315                 320

Phe Ser Asp Glu Gly Thr Tyr His Glu Leu Thr Glu Ala Leu Asp Tyr
                325                 330                 335

Ile Phe Ile Thr Asp Asp Ile His Leu Thr Gly Glu Ile Phe Ser Phe
                340                 345                 350

Phe Arg Ser Phe Gly His Pro Arg Leu Glu Ala Val Thr Ala Ala Glu
                355                 360                 365

Asn Val Arg Lys Tyr Met Asn Gln Pro Lys Val Ile Val Tyr Glu Thr
                370                 375                 380

Leu Met Lys Gly His Ala Ile Phe Cys Gly Ile Ile Asn Gly Tyr
385                 390                 395                 400

Arg Asp Arg His Gly Gly Ser Trp Pro Pro Leu Thr Leu Pro Leu His
                    405                 410                 415

Ala Ala Asp Thr Ile Arg Asn Ala Gln Ala Ser Gly Glu Gly Leu Thr
                420                 425                 430

His Glu Gln Cys Val Asp Asn Trp Lys Ser Phe Ala Gly Val Lys Phe
            435                 440                 445

Gly Cys Phe Met Pro Leu Ser Leu Asp Ser Asp Leu Thr Met Tyr Leu
450                 455                 460

Lys Asp Lys Ala Leu Ala Ala Leu Gln Arg Glu Trp Asp Ser Val Tyr
465                 470                 475                 480

Pro Lys Glu Phe Leu Arg Tyr Asp Pro Pro Lys Gly Thr Gly Ser Arg
                485                 490                 495

Arg Leu Val Asp Val Phe Leu Asn Asp Ser Ser Phe Asp Pro Tyr Asp
                500                 505                 510

Val Ile Met Tyr Val Val Ser Gly Ala Tyr Leu His Asp Pro Glu Phe
            515                 520                 525

Asn Leu Ser Tyr Ser Leu Lys Glu Lys Glu Ile Lys Glu Thr Gly Arg
530                 535                 540

Leu Phe Ala Lys Met Thr Tyr Lys Met Arg Ala Cys Gln Val Ile Ala
545                 550                 555                 560

Glu Asn Leu Ile Ser Asn Gly Ile Gly Lys Tyr Phe Lys Asp Asn Gly
                565                 570                 575

Met Ala Lys Asp Glu His Asp Leu Thr Lys Ala Leu His Thr Leu Ala
                580                 585                 590

Val Ser Gly Val Pro Lys Asp Leu Lys Glu Ser His Arg Gly Gly Pro
            595                 600                 605

Val Leu Lys Thr Tyr Ser Arg Ser Pro Val His Thr Ser Thr Arg Asn
            610                 615                 620

Val Arg Ala Ala Lys Gly Phe Ile Gly Phe Pro Gln Val Ile Arg Gln
625                 630                 635                 640

Asp Gln Asp Thr Asp His Pro Glu Asn Met Glu Ala Tyr Glu Thr Val
                645                 650                 655

Ser Ala Phe Ile Thr Thr Asp Leu Lys Lys Tyr Cys Leu Asn Trp Arg
                660                 665                 670

Tyr Glu Thr Ile Ser Leu Phe Ala Gln Arg Leu Asn Glu Ile Tyr Gly
            675                 680                 685

Leu Pro Ser Phe Phe Gln Trp Leu His Lys Arg Leu Glu Thr Ser Val
690                 695                 700
```

-continued

```
Leu Tyr Val Ser Asp Pro His Cys Pro Pro Asp Leu Asp Ala His Ile
705                 710                 715                 720

Pro Leu Tyr Lys Val Pro Asn Asp Gln Ile Phe Ile Lys Tyr Pro Met
            725                 730                 735

Gly Gly Ile Glu Gly Tyr Cys Gln Lys Leu Trp Thr Ile Ser Thr Ile
        740                 745                 750

Pro Tyr Leu Tyr Leu Ala Ala Tyr Glu Ser Gly Val Arg Ile Ala Ser
            755                 760                 765

Leu Val Gln Gly Asp Asn Gln Thr Ile Ala Val Thr Lys Arg Val Pro
770                 775                 780

Ser Thr Trp Pro Tyr Asn Leu Lys Lys Arg Glu Ala Ala Arg Val Thr
785                 790                 795                 800

Arg Asp Tyr Phe Val Ile Leu Arg Gln Arg Leu His Asp Ile Gly His
                805                 810                 815

His Leu Lys Ala Asn Glu Thr Ile Val Ser Ser His Phe Phe Val Tyr
            820                 825                 830

Ser Lys Gly Ile Tyr Tyr Asp Gly Leu Leu Val Ser Gln Ser Leu Lys
        835                 840                 845

Ser Ile Ala Arg Cys Val Phe Trp Ser Glu Thr Ile Val Asp Glu Thr
850                 855                 860

Arg Ala Ala Cys Ser Asn Ile Ala Thr Thr Met Ala Lys Ser Ile Glu
865                 870                 875                 880

Arg Gly Tyr Asp Arg Tyr Leu Ala Tyr Ser Leu Asn Val Leu Lys Val
                885                 890                 895

Ile Gln Gln Ile Leu Ile Ser Leu Gly Phe Thr Ile Asn Ser Thr Met
            900                 905                 910

Thr Arg Asp Val Val Ile Pro Leu Leu Thr Asn Asn Asp Leu Leu Ile
        915                 920                 925

Arg Met Ala Leu Leu Pro Ala Pro Ile Gly Gly Met Asn Tyr Leu Asn
930                 935                 940

Met Ser Arg Leu Phe Val Arg Asn Ile Gly Asp Pro Val Thr Ser Ser
945                 950                 955                 960

Ile Ala Asp Leu Lys Arg Met Ile Leu Ala Ser Leu Met Pro Glu Glu
                965                 970                 975

Thr Leu His Gln Val Met Thr Gln Gln Pro Gly Asp Ser Ser Phe Leu
            980                 985                 990

Asp Trp Ala Ser Asp Pro Tyr Ser Ala Asn Leu Val Cys Val Gln Ser
        995                 1000                1005

Ile Thr Arg Leu Leu Lys Asn Ile Thr Ala Arg Phe Val Leu Ile
    1010                1015                1020

His Ser Pro Asn Pro Met Leu Lys Gly Leu Phe His Asp Asp Ser
    1025                1030                1035

Lys Glu Glu Asp Glu Gly Leu Ala Ala Phe Leu Met Asp Arg His
    1040                1045                1050

Ile Ile Val Pro Arg Ala Ala His Glu Ile Leu Asp His Ser Val
    1055                1060                1065

Thr Gly Ala Arg Glu Ser Ile Ala Gly Met Leu Asp Thr Thr Lys
    1070                1075                1080

Gly Leu Ile Arg Ala Ser Met Arg Lys Gly Gly Leu Thr Ser Arg
    1085                1090                1095

Val Ile Thr Arg Leu Ser Asn Tyr Asp Tyr Glu Gln Phe Arg Ala
    1100                1105                1110
```

```
Gly Met Val Leu Leu Thr Gly Arg Lys Arg Asn Val Leu Ile Asp
    1115                1120                1125

Lys Glu Ser Cys Ser Val Gln Leu Ala Arg Ala Leu Arg Ser His
    1130                1135                1140

Met Trp Ala Arg Leu Ala Arg Gly Arg Pro Ile Tyr Gly Leu Glu
    1145                1150                1155

Val Pro Asp Val Leu Glu Ser Met Arg Gly His Leu Ile Arg Arg
    1160                1165                1170

His Glu Thr Cys Val Ile Cys Glu Cys Gly Ser Val Asn Tyr Gly
    1175                1180                1185

Trp Phe Phe Val Pro Ser Gly Cys Gln Leu Asp Asp Ile Asp Lys
    1190                1195                1200

Glu Thr Ser Ser Leu Arg Val Pro Tyr Ile Gly Ser Thr Thr Asp
    1205                1210                1215

Glu Arg Thr Asp Met Lys Leu Ala Phe Val Arg Ala Pro Ser Arg
    1220                1225                1230

Ser Leu Arg Ser Ala Val Arg Ile Ala Thr Val Tyr Ser Trp Ala
    1235                1240                1245

Tyr Gly Asp Asp Asp Ser Ser Trp Asn Glu Ala Trp Leu Leu Ala
    1250                1255                1260

Arg Gln Arg Ala Asn Val Ser Leu Glu Glu Leu Arg Val Ile Thr
    1265                1270                1275

Pro Ile Ser Thr Ser Thr Asn Leu Ala His Arg Leu Arg Asp Arg
    1280                1285                1290

Ser Thr Gln Val Lys Tyr Ser Gly Thr Ser Leu Val Arg Val Ala
    1295                1300                1305

Arg Tyr Thr Thr Ile Ser Asn Asp Asn Leu Ser Phe Val Ile Ser
    1310                1315                1320

Asp Lys Lys Val Asp Thr Asn Phe Ile Tyr Gln Gln Gly Met Leu
    1325                1330                1335

Leu Gly Leu Gly Val Leu Glu Thr Leu Phe Arg Leu Glu Lys Asp
    1340                1345                1350

Thr Gly Ser Ser Asn Thr Val Leu His Leu His Val Glu Thr Asp
    1355                1360                1365

Cys Cys Val Ile Pro Met Ile Asp His Pro Arg Ile Pro Ser Ser
    1370                1375                1380

Arg Lys Leu Glu Leu Arg Ala Glu Leu Cys Thr Asn Pro Leu Ile
    1385                1390                1395

Tyr Asp Asn Ala Pro Leu Ile Asp Arg Asp Ala Thr Arg Leu Tyr
    1400                1405                1410

Thr Gln Ser His Arg Arg His Leu Val Glu Phe Val Thr Trp Ser
    1415                1420                1425

Thr Pro Gln Leu Tyr His Ile Leu Ala Lys Ser Thr Ala Leu Ser
    1430                1435                1440

Met Ile Asp Leu Val Thr Lys Phe Glu Lys Asp His Met Asn Glu
    1445                1450                1455

Ile Ser Ala Leu Ile Gly Asp Asp Ile Asn Ser Phe Ile Thr
    1460                1465                1470

Glu Phe Leu Leu Ile Glu Pro Arg Leu Phe Thr Ile Tyr Leu Gly
    1475                1480                1485

Gln Cys Ala Ala Ile Asn Trp Ala Phe Asp Val His Tyr His Arg
    1490                1495                1500

Pro Ser Gly Lys Tyr Gln Met Gly Glu Leu Leu Ser Ser Phe Leu
```

```
                1505                1510                1515

Ser Arg Met Ser Lys Gly Val Phe Lys Val Leu Val Asn Ala Leu
    1520                1525                1530

Ser His Pro Lys Ile Tyr Lys Lys Phe Trp His Cys Gly Ile Ile
    1535                1540                1545

Glu Pro Ile His Gly Pro Ser Leu Asp Ala Gln Asn Leu His Thr
    1550                1555                1560

Thr Val Cys Asn Met Val Tyr Thr Cys Tyr Met Thr Tyr Leu Asp
    1565                1570                1575

Leu Leu Leu Asn Glu Glu Leu Glu Glu Phe Thr Phe Leu Leu Cys
    1580                1585                1590

Glu Ser Asp Glu Asp Val Val Pro Asp Arg Phe Asp Asn Ile Gln
    1595                1600                1605

Ala Lys His Leu Cys Val Leu Ala Asp Leu Tyr Cys Gln Pro Gly
    1610                1615                1620

Thr Cys Pro Pro Ile Arg Gly Leu Arg Pro Val Glu Lys Cys Ala
    1625                1630                1635

Val Leu Thr Asp His Ile Lys Ala Glu Ala Met Leu Ser Pro Ala
    1640                1645                1650

Gly Ser Ser Trp Asn Ile Asn Pro Ile Ile Val Asp His Tyr Ser
    1655                1660                1665

Cys Ser Leu Thr Tyr Leu Arg Arg Gly Ser Ile Lys Gln Ile Arg
    1670                1675                1680

Leu Arg Val Asp Pro Gly Phe Ile Phe Asp Ala Leu Ala Glu Val
    1685                1690                1695

Asn Val Ser Gln Pro Lys Ile Gly Ser Asn Asn Ile Ser Asn Met
    1700                1705                1710

Ser Ile Lys Ala Phe Arg Pro Pro His Asp Val Ala Lys Leu
    1715                1720                1725

Leu Lys Asp Ile Asn Thr Ser Lys His Asn Leu Pro Ile Ser Gly
    1730                1735                1740

Gly Asn Leu Ala Asn Tyr Glu Ile His Ala Phe Arg Arg Ile Gly
    1745                1750                1755

Leu Asn Ser Ser Ala Cys Tyr Lys Ala Val Glu Ile Ser Thr Leu
    1760                1765                1770

Ile Arg Arg Cys Leu Glu Pro Gly Glu Asp Gly Leu Phe Leu Gly
    1775                1780                1785

Glu Gly Ser Gly Ser Met Leu Ile Thr Tyr Lys Glu Ile Leu Lys
    1790                1795                1800

Leu Asn Lys Cys Phe Tyr Asn Ser Gly Val Ser Ala Asn Ser Arg
    1805                1810                1815

Ser Gly Gln Arg Glu Leu Ala Pro Tyr Pro Ser Glu Val Gly Leu
    1820                1825                1830

Val Glu His Arg Met Gly Val Gly Asn Ile Val Lys Val Leu Phe
    1835                1840                1845

Asn Gly Arg Pro Glu Val Thr Trp Val Gly Ser Val Asp Cys Phe
    1850                1855                1860

Asn Phe Ile Val Ser Asn Ile Pro Thr Ser Ser Val Gly Phe Ile
    1865                1870                1875

His Ser Asp Ile Glu Thr Leu Pro Asp Lys Asp Thr Ile Glu Lys
    1880                1885                1890

Leu Glu Glu Leu Ala Ala Ile Leu Ser Met Ala Leu Leu Leu Gly
    1895                1900                1905
```

```
Lys Ile Gly Ser Ile Leu Val Ile Lys Leu Met Pro Phe Ser Gly
1910                1915                1920

Asp Phe Val Gln Gly Phe Ile Ser Tyr Val Gly Ser His Tyr Arg
1925                1930                1935

Glu Val Asn Leu Val Tyr Pro Arg Tyr Ser Asn Phe Ile Ser Thr
1940                1945                1950

Glu Ser Tyr Leu Val Met Thr Asp Leu Lys Ala Asn Arg Leu Met
1955                1960                1965

Asn Pro Glu Lys Ile Lys Gln Gln Ile Ile Glu Ser Ser Val Arg
1970                1975                1980

Thr Ser Pro Gly Leu Ile Gly His Ile Leu Ser Ile Lys Gln Leu
1985                1990                1995

Ser Cys Ile Gln Ala Ile Val Gly Asp Ala Val Ser Arg Gly Asp
2000                2005                2010

Ile Asn Pro Thr Leu Lys Lys Leu Thr Pro Ile Glu Gln Val Leu
2015                2020                2025

Ile Asn Cys Gly Leu Ala Ile Asn Gly Pro Lys Leu Cys Lys Glu
2030                2035                2040

Leu Ile His His Asp Val Ala Ser Gly Gln Asp Gly Leu Leu Asn
2045                2050                2055

Ser Ile Leu Ile Leu Tyr Arg Glu Leu Ala Arg Phe Lys Asp Asn
2060                2065                2070

Gln Arg Ser Gln Gln Gly Met Phe His Ala Tyr Pro Val Leu Val
2075                2080                2085

Ser Ser Arg Gln Arg Glu Leu Ile Ser Arg Ile Thr Arg Lys Phe
2090                2095                2100

Trp Gly His Ile Leu Leu Tyr Ser Gly Asn Lys Lys Leu Ile Asn
2105                2110                2115

Lys Phe Ile Gln Asn Leu Lys Ser Gly Tyr Leu Ile Leu Asp Leu
2120                2125                2130

His Gln Asn Ile Phe Val Lys Asn Leu Ser Lys Ser Glu Lys Gln
2135                2140                2145

Ile Ile Met Thr Gly Gly Leu Lys Arg Glu Trp Val Phe Lys Val
2150                2155                2160

Thr Val Lys Glu Thr Lys Glu Trp Tyr Lys Leu Val Gly Tyr Ser
2165                2170                2175

Ala Leu Ile Lys Asp
2180

<210> SEQ ID NO 18
<211> LENGTH: 18967
<212> TYPE: DNA
<213> ORGANISM: Artificial
<220> FEATURE:
<223> OTHER INFORMATION: pTM-MVSchw plasmid

<400> SEQUENCE: 18
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga tggccacact tttaaggagc ttagcattgt tcaaaagaaa caaggacaaa     240
ccacccatta tcatcaggat ccggtggagc atcagaggaa tcaaacacat tattatagta     300
ccaatccctg gagattcctc aattaccact cgatccagac ttctggaccg gttggtgagg     360
```

| | |
|---|---|
| ttaattggaa acccggatgt gagcgggccc aaactaacag gggcactaat aggtatatta | 420 |
| tccttatttg tggagtctcc aggtcaattg attcagagga tcaccgatga ccctgacgtt | 480 |
| agcataaggc tgttagaggt tgtccagagt gaccagtcac aatctggcct taccttcgca | 540 |
| tcaagaggta ccaacatgga ggatgaggcg gaccaatact tttcacatga tgatccaatt | 600 |
| agtagtgatc aatccaggtt cggatggttc gggaacaagg aaatctcaga tattgaagtg | 660 |
| caagaccctg agggattcaa catgattctg ggtaccatcc tagcccaaat ttgggtcttg | 720 |
| ctcgcaaagg cggttacggc cccagacacg gcagctgatt cggagctaag aaggtggata | 780 |
| aagtacaccc aacaaagaag ggtagttggt gaatttagat tggagagaaa atggttggat | 840 |
| gtggtgagga acaggattgc cgaggacctc tccttacgcc gattcatggt cgctctaatc | 900 |
| ctggatatca agagaacacc cggaaacaaa cccaggattg ctgaaatgat atgtgacatt | 960 |
| gatacatata tcgtagaggc aggattagcc agttttatcc tgactattaa gtttgggata | 1020 |
| gaaactatgt atcctgctct tggactgcat gaatttgctg gtgagttatc cacacttgag | 1080 |
| tccttgatga acctttacca gcaaatgggg gaaactgcac cctacatggt aatcctggag | 1140 |
| aactcaattc agaacaagtt cagtgcagga tcatacccct gctctggag ctatgccatg | 1200 |
| ggagtaggag tggaacttga aaactccatg ggaggtttga actttggccg atcttacttt | 1260 |
| gatccagcat attttagatt agggcaagag atggtaagga ggtcagctgg aaaggtcagt | 1320 |
| tccacattgg catctgaact cggtatcact gccgaggatg caaggcttgt ttcagagatt | 1380 |
| gcaatgcata ctactgagga caagatcagt agagcggttg acccagaca agcccaagta | 1440 |
| tcatttctac acggtgatca aagtgagaat gagctaccga gattgggggg caaggaagat | 1500 |
| aggagggtca aacagagtcg aggagaagcc agggagagct acagagaaac cgggcccagc | 1560 |
| agagcaagtg atgcgagagc tgcccatctt ccaaccggca cacccctaga cattgacact | 1620 |
| gcaacggagt ccagccaaga tccgcaggac agtcgaaggt cagctgacgc cctgcttagg | 1680 |
| ctgcaagcca tggcaggaat ctcggaagaa caaggctcag acacggacac ccctatagtg | 1740 |
| tacaatgaca gaaatcttct agactaggtg cgagaggccg agggccagaa caacatccgc | 1800 |
| ctaccatcca tcattgttat aaaaaactta ggaaccaggt ccacacagcc gccagcccat | 1860 |
| caaccatcca ctcccacgat ggagccaat ggcagaagag caggcacgcc atgtcaaaaa | 1920 |
| cggactggaa tgcatccggg ctctcaaggc cgagcccatc ggctcactgg ccatcgagga | 1980 |
| agctatggca gcatggtcag aaatatcaga caacccagga caggagcgag ccacctgcag | 2040 |
| ggaagagaag gcaggcagtt cgggtctcag caaaccatgc ctctcagcaa ttggatcaac | 2100 |
| tgaaggcggt gcacctcgca tccgcggtca gggacctgga gagagcgatg acgacgctga | 2160 |
| aactttggga atcccccaa gaaatctcca ggcatcaagc actgggttac agtgttatta | 2220 |
| cgtttatgat cacagcggtg aagcggttaa gggaatccaa gatgctgact ctatcatggt | 2280 |
| tcaatcaggc cttgatggtg atagcaccct ctcaggagga acaatgaat ctgaaaacag | 2340 |
| cgatgtggat attggcgaac ctgataccga gggatatgct atcactgacc ggggatctgc | 2400 |
| tcccatctct atggggttca gggcttctga tgttgaaact gcagaaggag gggagatcca | 2460 |
| cgagctcctg agactccaat ccagaggcaa caactttccg aagcttggga aaactctcaa | 2520 |
| tgttcctccg cccccggacc ccggtagggc cagcacttcc gggacaccca ttaaaaaggg | 2580 |
| cacagacgcg agattagcct catttggaac ggagatcgcg tctttattga caggtggtgc | 2640 |
| aacccaatgt gctcgaaagt caccctcgga accatcaggg ccaggtgcac ctgcggggaa | 2700 |

```
tgtccccgag tgtgtgagca atgccgcact gatacaggag tggacacccg aatctggtac    2760
cacaatctcc ccgagatccc agaataatga agaaggggga gactattatg atgatgagct    2820
gttctctgat gtccaagata ttaaaacagc cttggccaaa atacacgagg ataatcagaa    2880
gataatctcc aagctagaat cactgctgtt attgaaggga gaagttgagt caattaagaa    2940
gcagatcaac aggcaaaata tcagcatatc caccctggaa ggacacctct caagcatcat    3000
gatcgccatt cctggacttg ggaaggatcc aacgacccc actgcagatg tcgaaatcaa     3060
tcccgacttg aaacccatca taggcagaga ttcaggccga gcactggccg aagttctcaa    3120
gaaacccgtt gccagccgac aactccaagg aatgacaaat ggacggacca gttccagagg    3180
acagctgctg aaggaatttc agctaaagcc gatcgggaaa aagatgagct cagccgtcgg    3240
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata ataatgaagt agctacagct    3420
caacttacct gccaaccca tgccagtcga cccaactagt acaacctaaa tccattataa     3480
aaaacttagg agcaaagtga ttgcctccca aggtccacaa tgacagagac ctacgacttc    3540
gacaagtcgg catgggacat caagggtcg atcgctccga tacaacccac cacctacagt     3600
gatggcaggc tggtgcccca ggtcagagtc atagatcctg gtctaggcga caggaaggat    3660
gaatgcttta tgtacatgtt tctgctgggg gttgttgagg acagcgattc cctagggcct    3720
ccaatcgggc gagcatttgg gttcctgccc ttaggtgttg gcagatccac agcaaagccc    3780
gaaaaactcc tcaaagaggc cactgagctt gacatagttg ttagacgtac agcagggctc    3840
aatgaaaaac tggtgttcta caacaacacc ccactaactc tcctcacacc ttggagaaag    3900
gtcctaacaa cagggagtgt cttcaacgca accaagtgt gcaatgcggt taatctgata    3960
ccgctcgata ccccgcagag gttccgtgtt gtttatatga gcatcacccg tctttcggat    4020
aacgggtatt acaccgttcc tagaagaatg ctggaattca gatcggtcaa tgcagtggcc    4080
ttcaacctgc tggtgaccct taggattgac aaggcgatag gccctgggaa gatcatcgac    4140
aatacagagc aacttcctga ggcaacattt atggtccaca tcgggaactt caggagaaag    4200
aagagtgaag tctactctgc cgattattgc aaaatgaaaa tcgaaaagat gggcctggtt    4260
tttgcacttg gtgggatagg ggcaccagt cttcacatta gaagcacagg caaaatgagc     4320
aagactctcc atgcacaact cgggttcaag aagaccttat gttacccgct gatggatatc    4380
aatgaagacc ttaatcgatt actctggagg agcagatgca agatagtaag aatccaggca    4440
gttttgcagc catcagttcc tcaagaattc cgcatttacg acgacgtgat cataaatgat    4500
gaccaaggac tattcaaagt tctgtagacc gtagtgccca gcaatgcccg aaaacgaccc    4560
ccctcacaat gacagccaga aggcccggac aaaaaagccc cctccgaaag actccacgga    4620
ccaagcgaga ggccagccag cagccgacgg caagcgcgaa caccaggcgg ccccagcaca    4680
gaacagccct gacacaaggc caccaccagc cacccccaatc tgcatcctcc tcgtgggacc   4740
cccgaggacc aaccccccaag gctgcccccg atccaaacca ccaaccgcat cccccaccacc  4800 cccgggaaag aaaccccccag caattggaag gcccctcccc ctcttcctca acacaagaac   4860
tccacaaccg aaccgcacaa gcgaccgagg tgacccaacc gcaggcatcc gactccctag    4920
acagatcctc tctccccggc aaactaaaca aaacttaggg ccaaggaaca tacacaccca    4980
acagaaccca gaccccggcc cacggcgccg cgccccaac ccccgacaac cagagggagc     5040
ccccaaccaa tcccgccggc tccccccggtg cccacaggca gggacaccaa cccccgaaca   5100
```

```
gacccagcac ccaaccatcg acaatccaag acgggggggc cccccaaaa aaaggccccc    5160 aggggccgac agccagcacc gcgaggaagc ccacccaccc cacacacgac cacggcaacc    5220
aaaccagaac ccagaccacc ctgggccacc agctcccaga ctcggccatc accccgcaga    5280
aaggaaaggc cacaacccgc gcaccccagc cccgatccgg cggggagcca cccaacccga    5340
accagcaccc aagagcgatc cccgaaggac ccccgaaccg caaaggacat cagtatccca    5400
cagcctctcc aagtcccccg gtctcctcct cttctcgaag ggaccaaaag atcaatccac    5460
cacacccgac gacactcaac tccccacccc taaaggagac accgggaatc ccagaatcaa    5520
gactcatcca atgtccatca tgggtctcaa ggtgaacgtc tctgccatat tcatggcagt    5580
actgttaact ctccaaacac ccaccggtca aatccattgg ggcaatctct ctaagatagg    5640
ggtggtagga ataggaagtg caagctacaa agttatgact cgttccagcc atcaatcatt    5700
agtcataaaa ttaatgccca atataactct cctcaataac tgcacgaggg tagagattgc    5760
agaatacagg agactactga gaacagtttt ggaaccaatt agagatgcac ttaatgcaat    5820
gacccagaat ataagaccgg ttcagagtgt agcttcaagt aggagacaca agagatttgc    5880
gggagtagtc ctggcaggtg cggccctagg cgttgccaca gctgctcaga taacagccgg    5940
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcgggct caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaaggggt     6420 gattgtccac cggctagagg gggtctcgta caacataggc tctcaagagt ggtataccac    6480
tgtgcccaag tatgttgcaa cccaagggta ccttatctcg aattttgatg agtcatcgtg    6540
tactttcatg ccagagggga ctgtgtgcag ccaaaatgcc ttgtacccga tgagtcctct    6600
gctccaagaa tgcctccggg ggtacaccaa gtcctgtgct cgtacactcg tatccgggtc    6660
ttttgggaac cggttcattt tatcacaagg gaacctaata gccaattgtg catcaatcct    6720
ttgcaagtgt tacacaacag gaacgatcat taatcaagac cctgacaaga tcctaacata    6780
cattgctgcc gatcactgcc cggtagtcga ggtgaacggc gtgaccatcc aagtcggag     6840 caggaggtat ccagacgctg tgtacttgca cagaattgac ctcggtcctc ccatatcatt    6900
ggagaggttg gacgtaggga caaatctggg gaatgcaatt gctaagttgg aggatgccaa    6960
ggaattgttg gagtcatcgg accagatatt gaggagtatg aaaggtttat cgagcactag    7020
catagtctac atcctgattg cagtgtgtct tgggggttg ataggggatcc ccgctttaat     7080 atgttgctgc aggggcgtt gtaacaaaaa gggagaacaa gttggtatgt caagaccagg     7140
cctaaagcct gatcttacgg gaacatcaaa atcctatgta aggtcgctct gatcctctac    7200
aactcttgaa acacaaatgt cccacaagtc tcctcttcgt catcaagcaa ccaccgcacc    7260
cagcatcaag cccacctgaa attatctccg gcttccctct ggccgaacaa tatcggtagt    7320
taatcaaaac ttagggtgca agatcatcca caatgtcacc acaacgagac cggataaatg    7380
ccttctacaa agataacccc catcccaagg gaagtaggat agtcattaac agagaacatc    7440
```

```
ttatgattga tagaccttat gttttgctgg ctgttctgtt tgtcatgttt ctgagcttga    7500
tcgggttgct agccattgca ggcattagac ttcatcgggc agccatctac accgcagaga    7560
tccataaaag cctcagcacc aatctagatg taactaactc aatcgagcat caggtcaagg    7620
acgtgctgac accactcttc aaaatcatcg gtgatgaagt gggcctgagg acacctcaga    7680
gattcactga cctagtgaaa ttaatctctg acaagattaa attccttaat ccggataggg    7740
agtacgactt cagagatctc acttggtgta tcaacccgcc agagagaatc aaattggatt    7800
atgatcaata ctgtgcagat gtggctgctg aagagctcat gaatgcattg gtgaactcaa    7860
ctctactgga gaccagaaca accaatcagt tcctagctgt ctcaaaggga aactgctcag    7920
ggcccactac aatcagaggt caattctcaa acatgtcgct gtccctgtta gacttgtatt    7980
taggtcgagg ttacaatgtg tcatctatag tcactatgac atcccaggga atgtatgggg    8040
gaacttacct agtggaaaag cctaatctga gcagcaaaag gtcagagttg tcacaactga    8100
gcatgtaccg agtgtttgaa gtaggtgtta tcagaaatcc gggtttgggg gctccggtgt    8160
tccatatgac aaactatctt gagcaaccag tcagtaatga tctcagcaac tgtatggtgg    8220
cttttgggga gctcaaactc gcagcccttt gtcacgggga agattctatc acaattccct    8280
atcagggatc agggaaaggt gtcagcttcc agctcgtcaa gctaggtgtc tggaaatccc    8340
caaccgacat gcaatcctgg gtcccctat caacggatga tccagtgata gacaggcttt    8400
acctctcatc tcagagggt gttatcgctg acaatcaagc aaaatgggct gtcccgacaa    8460
cacgaacaga tgacaagttg cgaatggaga catgcttcca acaggcgtgt aagggtaaaa    8520
tccaagcact ctgcgagaat cccgagtggg caccattgaa ggataacagg attccttcat    8580
acggggtctt gtctgttgat ctgagtctga cagttgagct taaaatcaaa attgcttcgg    8640
gattcgggcc attgatcaca cacggttcag ggatggacct atacaaatcc aaccacaaca    8700
atgtgtattg gctgactatc ccgccaatga agaacctagc cttaggtgta atcaacacat    8760
tggagtggat accgagattc aaggttagtc cctacctctt cactgtccca attaaggaag    8820
caggcgaaga ctgccatgcc ccaacatacc tacctgcgga ggtggatggt gatgtcaaac    8880
tcagttccaa tctggtgatt ctacctggtc aagatctcca atatgttttg gcaacctacg    8940
atacttccag ggttgaacat gctgtggttt attacgttta cagcccaagc cgctcatttt    9000
cttactttta tcctttagg ttgcctataa aggggtccc catcgaatta caagtggaat    9060
gcttcacatg ggaccaaaaa ctctggtgcc gtcacttctg tgtgcttgcg gactcagaat    9120
ctggtggaca tatcactcac tctgggatgg tgggcatggg agtcagctgc acagtcaccc    9180
gggaagatgg aaccaatcgc agatagggct gctagtgaac caatcacatg atgtcaccca    9240
gacatcaggc atacccacta gtgtgaaata gacatcagaa ttaagaaaaa cgtagggtcc    9300
aagtggttcc ccgttatgga ctcgctatct gtcaaccaga tcttataccc tgaagttcac    9360
ctagatagcc cgatagttac caataagata gtagccatcc tggagtatgc tcgagtccct    9420
cacgcttaca gcctggagga ccctacactg tgtcagaaca tcaagcaccg cctaaaaaac    9480
ggattttcca accaaatgat tataaacaat gtggaagttg ggaatgtcat caagtccaag    9540
cttaggagtt atccggccca ctctcatatt ccatatccaa attgtaatca ggatttattt    9600
aacatagaag acaaagagtc aacgaggaag atccgtgaac tcctcaaaaa ggggaattcg    9660
ctgtactcca agtcagtgaa taaggttttc aatgcttaa gggacactaa ctcacggctt    9720
ggcctaggct ccgaattgag ggaggacatc aaggagaaag ttattaactt gggagtttac    9780
atgcacagct cccagtggtt tgagcccttt ctgttttggt ttacagtcaa gactgagatg    9840
```

```
aggtcagtga ttaaatcaca aacccatact tgccatagga ggagacacac acctgtattc    9900
ttcactggta gttcagttga gttgctaatc tctcgtgacc ttgttgctat aatcagtaaa    9960
gagtctcaac atgtatatta cctgacattt gaactggttt tgatgtattg tgatgtcata  10020
gaggggaggt taatgacaga gaccgctatg actattgatg ctaggtatac agagcttcta  10080
ggaagagtca gatacatgtg gaaactgata gatggtttct tccctgcact cgggaatcca  10140
acttatcaaa ttgtagccat gctggagcct ctttcacttg cttacctgca gctgagggat  10200
ataacagtag aactcagagg tgctttcctt aaccactgct ttactgaaat acatgatgtt  10260
cttgaccaaa acgggttttc tgatgaaggt acttatcatg agttaactga agctctagat  10320
tacattttca taactgatga catacatctg acaggggaga ttttctcatt tttcagaagt  10380
ttcggccacc ccagacttga agcagtaacg gctgctgaaa atgttaggaa atacatgaat  10440
cagcctaaag tcattgtgta tgagactctg atgaaaggtc atgccatatt tgtggaatc   10500
ataatcaacg gctatcgtga caggcacgga ggcagttggc caccgctgac cctcccctg   10560
catgctgcag acacaatccg gaatgctcaa gcttcaggtg aagggttaac acatgagcag  10620
tgcgttgata actggaaatc ttttgctgga gtgaaatttg gctgctttat gcctcttagc  10680
ctggatagtg atctgacaat gtacctaaag gacaaggcac ttgctgctct ccaaagggaa  10740
tgggattcag tttacccgaa agagttcctg cgttacgacc ctcccaaggg aaccgggtca  10800
cggaggcttg tagatgtttt ccttaatgat tcgagctttg acccatatga tgtgataatg  10860
tatgttgtaa gtggagctta cctccatgac cctgagttca acctgtctta cagcctgaaa  10920
gaaaaggaga tcaaggaaac aggtagactt tttgctaaaa tgacttacaa aatgagggca  10980
tgccaagtga ttgctgaaaa tctaatctca aacgggattg gcaaatattt taaggacaat  11040
gggatggcca aggatgagca cgatttgact aaggcactcc acactctagc tgtctcagga  11100
gtccccaaag atctcaaaga aagtcacagg gggggccag tcttaaaaac ctactcccga   11160
agcccagtcc acacaagtac caggaacgtg agagcagcaa aagggtttat agggttccct  11220
caagtaattc ggcaggacca agacactgat catccggaga atatggaagc ttacgagaca  11280
gtcagtgcat ttatcacgac tgatctcaag aagtactgcc ttaattggag atatgagacc  11340
atcagcttgt ttgcacagag gctaaatgag atttacggat tgccctcatt tttccagtgg  11400
ctgcataaga ggcttgagac ctctgtcctg tatgtaagtg accctcattg ccccccgac   11460
cttgacgccc atatcccgtt atataaagtc cccaatgatc aaatcttcat taagtaccct  11520
atgggaggta tagaagggta ttgtcagaag ctgtggacca tcagcaccat tccctatcta  11580
tacctggctg cttatgagag cggagtaagg attgcttcgt tagtgcaagg ggacaatcag  11640
accatagccg taacaaaaag ggtacccagc acatggccct acaaccttaa gaaacgggaa  11700
gctgctagag taactagaga ttactttgta attcttaggc aaaggctaca tgatattggc  11760
catcacctca aggcaaatga gacaattgtt tcatacatt tttttgtcta ttcaaaagga   11820
atatattatg atgggctact tgtgtcccaa tcactcaaga gcatcgcaag atgtgtattc  11880
tggtcagaga ctatagttga tgaaacaagg gcagcatgca gtaatattgc tacaacaatg  11940
gctaaaagca tcgagagagg ttatgaccgt taccttgcat attccctgaa cgtcctaaaa  12000
gtgatacagc aaattctgat ctctcttggc ttcacaatca attcaaccat gacccgggat  12060
gtagtcatac ccctcctcac aaacaacgac ctccttaataa ggatggcact gttgcccgct  12120
cctattgggg ggatgaatta tctgaatatg agcaggctgt ttgtcagaaa catcggtgat  12180
```

```
ccagtaacat catcaattgc tgatctcaag agaatgattc tcgcctcact aatgcctgaa    12240
gagaccctcc atcaagtaat gacacaacaa ccgggggact cttcattcct agactgggct    12300 agcgacccctt actcagcaaa tcttgtatgt gtccagagca tcactagact cctcaagaac    12360
ataactgcaa ggtttgtcct gatccatagt ccaaacccaa tgttaaaagg attattccat    12420
gatgacagta agaagagga cgagggactg gcggcattcc tcatggacag gcatattata    12480
gtacctaggg cagctcatga aatcctggat catagtgtca caggggcaag agagtctatt    12540
gcaggcatgc tggataccac aaaaggcttg attcgagcca gcatgaggaa gggggggtta    12600
acctctcgag tgataaccag attgtccaat tatgactatg aacaattcag agcagggatg    12660
gtgctattga caggaagaaa gagaaatgtc ctcattgaca aagagtcatg ttcagtgcag    12720
ctggcgagag ctctaagaag ccatatgtgg gcgaggctag ctcgaggacg gcctatttac    12780
ggccttgagg tccctgatgt actagaatct atgcgaggcc accttattcg gcgtcatgag    12840
acatgtgtca tctgcgagtg tggatcagtc aactacggat ggttttttgt ccctcgggt     12900 tgccaactgg atgatattga caaggaaaca tcatccttga gagtcccata tattggttct    12960
accactgatg agagaacaga catgaagctt gccttcgtaa gagccccaag tcgatccttg    13020
cgatctgctg ttagaatagc aacagtgtac tcatgggctt acggtgatga tgatagctct    13080
tggaacgaag cctggttgtt ggctaggcaa agggccaatg tgagcctgga ggagctaagg    13140
gtgatcactc ccatctcaac ttcgactaat ttagcgcata ggttgaggga tcgtagcact    13200
caagtgaaat actcaggtac atcccttgtc cgagtggcga ggtataccac aatctccaac    13260
gacaatctct catttgtcat atcagataag aaggttgata ctaactttat ataccaacaa    13320
ggaatgcttc tagggttggg tgttttagaa acattgtttc gactcgagaa agataccgga    13380
tcatctaaca cggtattaca tcttcacgtc gaaacagatt gttgcgtgat cccgatgata    13440
gatcatccca ggatacccag ctcccgcaag ctagagctga gggcagagct atgtaccaac    13500
ccattgatat atgataatgc acctttaatt gacagagatg caacaaggct atacacccag    13560
agccatagga ggcaccttgt ggaatttgtt acatggtcca caccccaact atatcacatt    13620
ttagctaagt ccacagcact atctatgatt gacctggtaa caaaatttga aaggaccat    13680 atgaatgaaa tttcagctct catagggat gacgatatca atagtttcat aactgagttt    13740
ctgctcatag agccaagatt attcactatc tacttgggcc agtgtgcggc catcaattgg    13800
gcatttgatg tacattatca tagaccatca gggaaatatc agatgggtga gctgttgtca    13860
tcgttccttt ctagaatgag caaaggagtg tttaaggtgc ttgtcaatgc tctaagccac    13920
ccaaagatct acaagaaatt ctggcattgt ggtattatag agcctatcca tggtccttca    13980
cttgatgctc aaaacttgca cacaactgtg tgcaacatgg tttacacatg ctatatgacc    14040
tacctcgacc tgttgttgaa tgaagagtta aagagttca catttctctt gtgtgaaagc    14100
gacgaggatg tagtaccgga cagattcgac aacatccagg caaaacactt atgtgttctg    14160
gcagatttgt actgtcaacc agggacctgc ccaccaattc gaggtctaag accggtagag    14220
aaatgtgcag ttctaaccga ccatatcaag gcagaggcta tgttatctcc agcaggatct    14280
tcgtggaaca taaatccaat tattgtagac cattactcat gctctctgac ttatctccgg    14340
cgaggatcga tcaaacagat aagattgaga gttgatccag gattcatttt cgacgccctc    14400
gctgaggtaa atgtcagtca gccaaagatc ggcagcaaca acatctcaaa tatgagcatc    14460
aaggctttca gacccccaca cgatgatgtt gcaaaattgc tcaaagatat caacacaagc    14520
aagcacaatc ttcccatttc agggggcaat ctcgccaatt atgaaatcca tgctttccgc    14580
```

```
agaatcgggt tgaactcatc tgcttgctac aaagctgttg agatatcaac attaattagg   14640
agatgccttg agccagggga ggacggcttg ttcttgggtg agggatcggg ttctatgttg   14700
atcacttata aagagatact taaactaaac aagtgcttct ataatagtgg ggtttccgcc   14760
aattctagat ctggtcaaag ggaattagca ccctatccct ccgaagttgg ccttgtcgaa   14820
cacagaatgg gagtaggtaa tattgtcaaa gtgctcttta acgggaggcc cgaagtcacg   14880
tgggtaggca gtgtagattg cttcaatttc atagttagta atatccctac ctctagtgtg   14940
gggtttatcc attcagatat agagaccttg cctgacaaag atactataga gaagctagag   15000
gaattggcag ccatcttatc gatggctctg ctcctgggca aaataggatc aatactggtg   15060
attaagctta tgcctttcag cggggatttt gttcagggat ttataagtta tgtagggtct   15120
cattatagag aagtgaacct tgtataccct agatacagca acttcatctc tactgaatct   15180
tatttggtta tgacagatct caaggctaac cggctaatga atcctgaaaa gattaagcag   15240
cagataattg aatcatctgt gaggacttca cctggactta taggtcacat cctatccatt   15300
aagcaactaa gctgcataca agcaattgtg ggagacgcag ttagtagagg tgatatcaat   15360
cctactctga aaaacttac acctatagag caggtgctga tcaattgcgg gttggcaatt   15420
aacggaccta agctgtgcaa agaattgatc caccatgatg ttgcctcagg gcaagatgga   15480
ttgcttaatt ctatactcat cctctacagg gagttggcaa gattcaaaga caaccaaaga   15540
agtcaacaag ggatgttcca cgcttacccc gtattggtaa gtagcaggca acgagaactt   15600
atatctagga tcacccgcaa attctggggg cacattcttc tttactccgg gaacaaaaag   15660
ttgataaata agtttatcca gaatctcaag tccggctatc tgatactaga cttacaccag   15720
aatatcttcg ttaagaatct atccaagtca gagaaacaga ttattatgac gggggggtttg   15780 aaacgtgagt gggtttttaa ggtaacagtc aaggagacca aagaatggta taagttagtc   15840
ggatacagtg ccctgattaa ggactaattg gttgaactcc ggaaccctaa tcctgcccta   15900
ggtggttagg cattatttgc aatatattaa agaaaacttt gaaaatacga agtttctatt   15960
cccagctttg tctggtggcc ggcatggtcc cagcctcctc gctggcgccg gctgggcaac   16020
attccgaggg gaccgtcccc tcggtaatgg cgaatgggac gcggccgatc cggctgctaa   16080
caaagcccga aaggaagctg agttggctgc tgccaccgct gagcaataac tagcataacc   16140
ccttggggcc tctaaacggg tcttgagggg ttttttgctg aaaggaggaa ctatatccgg   16200
atgcggccgc gggccctatg gtacccagct tttgttccct ttagtgaggg ttaattccga   16260
gcttggcgta atcatggtca tagctgtttc ctgtgtgaaa ttgttatccg ctcacaattc   16320
cacacaacat aggagccgga agcataaagt gtaaagcctg gggtgcctaa tgagtgaggt   16380
aactcacatt aattgcgttg cgctcactgc ccgctttcca gtcgggaaac ctgtcgtgcc   16440
agctgcatta atgaatcggc caacgcgcgg ggagaggcgg tttgcgtatt gggcgctctt   16500
ccgcttcctc gctcactgac tcgctgcgct cggtcgttcg ctgcggcga gcggtatcag   16560 ctcactcaaa ggcggtaata cggttatcca cagaatcagg ggataacgca ggaaagaaca   16620
tgtgagcaaa aggccagcaa aaggccagga accgtaaaaa ggccgcgttg ctggcgtttt   16680
tccataggct cggccccct gacgagcatc acaaaaatcg acgctcaagt cagaggtggc   16740
gaaacccgac aggactataa agataccagg cgttcccccc tggaagctcc ctcgtgcgct   16800
ctcctgttcc gaccctgccg cttaccggat acctgtccgc ctttctccct tcgggaagcg   16860
tggcgctttc tcaatgctca cgctgtaggt atctcagttc ggtgtaggtc gttcgctcca   16920
```

```
agctgggctg tgtgcacgaa ccccccgttc agcccgaccg ctgcgcctta tccggtaact    16980
atcgtcttga gtccaacccg gtaagacacg acttatcgcc actggcagca gccactggta    17040
acaggattag cagagcgagg tatgtaggcg gtgctacaga gttcttgaag tggtggccta    17100
actacggcta cactagaagg acagtatttg gtatctgcgc tctgctgaag ccagttacct    17160
tcggaaaaag agttggtagc tcttgatccg gcaaacaaac caccgctggt agcggtggtt    17220
tttttgtttg caagcagcag attacgcgca gaaaaaagg atctcaagaa gatcctttga    17280
tcttttctac ggggtctgac gctcagtgga acgaaaactc acgttaaggg attttggtca    17340
tgagattatc aaaaaggatc ttcacctaga tccttttaaa ttaaaaatga agttttaaat    17400
caatctaaag tatatatgag taaacttggt ctgacagtta ccaatgctta atcagtgagg    17460
cacctatctc agcgatctgt ctatttcgtt catccatagt tgcctgactg cccgtcgtgt    17520
agataactac gatacgggag ggcttaccat ctggccccag tgctgcaatg ataccgcgag    17580
acccacgctc accggctcca gatttatcag caataaacca gccagccgga agggccgagc    17640
gcagaagtgg tcctgcaact ttatccgcct ccatccagtc tattaattgt tgccgggaag    17700
ctagagtaag tagttcgcca gttaatagtt tgcgcaacgt tgttgccatt gctacaggca    17760
tcgtggtgtc acgctcgtcg tttggtatgg cttcattcag ctccggttcc caacgatcaa    17820
ggcgagttac atgatccccc atgttgtgaa aaaagcggt tagctccttc ggtcctccga    17880
tcgttgtcag aagtaagttg gccgcagtgt tatcactcat gcttatggca gcactgcata    17940
attctcttac tgtcatgcca tccgtaagat gcttttctgt gactggtgag tactcaacca    18000
agtcattctg agaatagtgt atgcggcgac cgagttgctc ttgcccggcg tcaatacggg    18060
ataataccgc gccacatagc agaactttaa aagtgctcat cattggaaaa cgttcttcgg    18120
ggcgaaaact ctcaaggatc ttaccgctgt tgagatccag ttcgatgtaa cccactcgtg    18180
cacccaactg atcttcagca tcttttactt tcaccagcgt ttctgggtga gcaaaaacag    18240
gaaggcaaaa tgccgcaaaa aagggaataa gggcgacacg gaaatgttga atactcatac    18300
tcttcctttt tcaatattat tgaagcattt atcagggtta ttgtctcatg agcggataca    18360
tatttgaatg tatttagaaa aataaacaaa taggggttcc gcgcacattt ccccgaaaag    18420
tgccacctga aattgtaaac gttaatattt tgttaaaatt cgcgttaaat ttttgttaaa    18480
tcagctcatt ttttaaccaa taggccgaaa tcggcaaaat cccttataaa tcaaaagaat    18540
agaccgagat agggttgagt gttgttccag tttggaacaa gagtccacta ttaaagaacg    18600
tggactccaa cgtcaaaggg cgaaaaaccg tctatcaggg cgatggccca ctacgtgaac    18660
catcacccta atcaagtttt tggggtcga ggtgccgtaa agcactaaat cggaacccta    18720
aagggagccc ccgatttaga gcttgacggg gaaagccggc gaacgtggcg agaaaggaag    18780
ggaagaaagc gaaaggagcg ggcgctaggg cgctggcaag tgtagcggtc acgctgcgcg    18840
taaccaccac acccgccgcg cttaatgcgc cgctacaggg cgcgtcccat tcgccattca    18900
ggctgcgcaa ctgttgggaa gggcgatcgg tgcgggcctc ttcgctatta cgccagccac    18960
cgcggtg                                                              18967
```

<210> SEQ ID NO 19
<211> LENGTH: 12082
<212> TYPE: DNA
<213> ORGANISM: Artificial
<220> FEATURE:
<223> OTHER INFORMATION: pEMC-LSchw plasmid

<400> SEQUENCE: 19

```
aagcttttgc gatcaataaa tggatcacaa ccagtatctc ttaacgatgt tcttcgcaga      60
tgatgattca ttttttaagt atttggctag tcaagatgat gaatcttcat tatctgatat     120
attgcaaatc actcaatatc tagactttct gttattatta ttgatccaat caaaaaataa     180
attagaagcc gtgggtcatt gttatgaatc tctttcagag gaatacagac aattgacaaa     240
attcacagac tttcaagatt ttaaaaaact gtttaacaag gtccctattg ttacagatgg     300
aagggtcaaa cttaataaag gatatttgtt cgactttgtg attagtttga tgcgattcaa     360
aaaagaatcc tctctagcta ccaccgcaat agatcctgtt agatacatag atcctcgtcg     420
caatatcgca ttttctaacg tgatggatat attaaagtcg aataaagtga acaataatta     480
attctttatt gtcatcatga acggcggaca tattcagttg ataatcggcc ccatgttttc     540
aggtaaaagt acagaattaa ttagacgagt tagacgttat caaatagctc aatataaatg     600
cgtgactata aaatattcta acgataatag atacggaacg ggactatgga cgcatgataa     660
gaataatttt gaagcattgg aagcaactaa actatgtgat gtcttggaat caattacaga     720
tttctccgtg ataggtatcg atgaaggaca gttcttttcca gacattgttg aattgatctc     780
gatcccgcga aattaatacg actcactata gggagaccac aacggtttcc ctctagcggg     840
atcaattccg cccctctccc tccccccccc ctaacgttac tggccgaagc cgcttggaat     900
aaggccggtg tgcgtttgtc tatatgttat tttccaccat attgccgtct tttggcaatg     960
tgagggcccg gaaacctggc cctgtcttct tgacgagcat tcctagggt  ctttcccctc    1020 tcgccaaagg aatgcaaggt ctgttgaatg tcgtgaagga agcagttcct ctggaagctt    1080
cttgaagaca aacaacgtct gtagcgaccc tttgcaggca gcggaacccc ccacctggcg    1140
acaggtgcct ctgcggccaa aagccacgtg tataagatac acctgcaaag gcggcacaac    1200
cccagtgcca cgttgtgagt tggatagttg tggaaagagt caaatggctc tcctcaagcg    1260
tattcaacaa ggggctgaag gatgcccaga aggtacccca ttgtatggga tctgatctgg    1320
ggcctcggtg cacatgcttt acatgtgttt agtcgaggtt aaaaaacgtc taggccccccc    1380 gaaccacggg gacgtggttt tcctttgaaa aacacgataa taccatggac tcgctatctg    1440
tcaaccagat cttataccct gaagttcacc tagatagccc gatagttacc aataagatag    1500
tagccatcct ggagtatgct cgagtccctc acgcttacag cctggaggac cctacactgt    1560
gtcagaacat caagcaccgc ctaaaaaacg gattttccaa ccaaatgatt ataaacaatg    1620
tggaagttgg gaatgtcatc aagtccaagc ttaggagtta tccggcccac tctcatattc    1680
catatccaaa ttgtaatcag gatttattta acatagaaga caaagagtca acgaggaaga    1740
tccgtgaact cctcaaaaag gggaattcgc tgtactccaa agtcagtgat aaggttttcc    1800
aatgcttaag ggacactaac tcacggcttg gcctaggctc cgaattgagg gaggacatca    1860
aggagaaagt tattaacttg ggagtttaca tgcacagctc ccagtggttt gagccctttc    1920
tgttttggtt tacagtcaag actgagatga ggtcagtgat taaatcacaa acccatactt    1980
gccataggag gagacacaca cctgtattct tcactggtag ttcagttgag ttgctaatct    2040
ctcgtgacct tgttgctata atcagtaaag agtctcaaca tgtatattac ctgacatttg    2100
aactggtttt gatgtattgt gatgtcatag aggggaggtt aatgacagag accgctatga    2160
ctattgatgc taggtataca gagcttctag gaagagtcag atacatgtgg aaactgatag    2220
atggtttctt ccctgcactc gggaatccaa cttatcaaat tgtagccatg ctggagcctc    2280
tttcacttgc ttacctgcag ctgagggata taacagtaga actcagaggt gctttcctta    2340
```

```
accactgctt tactgaaata catgatgttc ttgaccaaaa cgggttttct gatgaaggta    2400
cttatcatga gttaactgaa gctctagatt acattttcat aactgatgac atacatctga    2460
caggggagat tttctcattt ttcagaagtt tcggccaccc cagacttgaa gcagtaacgg    2520
ctgctgaaaa tgttaggaaa tacatgaatc agcctaaagt cattgtgtat gagactctga    2580
tgaaaggtca tgccatattt tgtggaatca taatcaacgg ctatcgtgac aggcacggag    2640
gcagttggcc accgctgacc ctcccctgc atgctgcaga cacaatccgg aatgctcaag    2700
cttcaggtga agggttaaca catgagcagt gcgttgataa ctggaaatct tttgctggag    2760
tgaaatttgg ctgctttatg cctcttagcc tggatagtga tctgacaatg tacctaaagg    2820
acaaggcact tgctgctctc caaagggaat gggattcagt ttacccgaaa gagttcctgc    2880
gttacgaccc tcccaaggga accgggtcac ggaggcttgt agatgttttc cttaatgatt    2940
cgagctttga cccatatgat gtgataatgt atgttgtaag tggagcttac ctccatgacc    3000
ctgagttcaa cctgtcttac agcctgaaag aaaaggagat caaggaaaca ggtagacttt    3060
ttgctaaaat gacttacaaa atgagggcat gccaagtgat tgctgaaaat ctaatctcaa    3120
acgggattgg caaatatttt aaggacaatg ggatggccaa ggatgagcac gatttgacta    3180
aggcactcca cactctagct gtctcaggag tccccaaaga tctcaaagaa agtcacaggg    3240
gggggccagt cttaaaaacc tactcccgaa gcccagtcca cacaagtacc aggaacgtga    3300
gagcagcaaa agggtttata gggttccctc aagtaattcg gcaggaccaa gacactgatc    3360
atccggagaa tatggaagct tacgagacag tcagtgcatt tatcacgact gatctcaaga    3420
agtactgcct taattggaga tatgagacca tcagcttgtt tgcacagagg ctaaatgaga    3480
tttacggatt gccctcattt ttccagtggc tgcataagag gcttgagacc tctgtcctgt    3540
atgtaagtga ccctcattgc cccccgacc ttgacgccca tatcccgtta tataaagtcc    3600
ccaatgatca aatcttcatt aagtacccta tgggaggtat agaagggtat tgtcagaagc    3660
tgtggaccat cagcaccatt ccctatctat acctggctgc ttatgagagc ggagtaagga    3720
ttgcttcgtt agtgcaaggg gacaatcaga ccatagccgt aacaaaaagg gtacccagca    3780
catggcccta caaccttaag aaacgggaag ctgctagagt aactagagat tactttgtaa    3840
ttcttaggca aaggctacat gatattggcc atcacctcaa ggcaaatgag acaattgttt    3900
catcacattt ttttgtctat tcaaaaggaa tatattatga tgggctactt tgtgtcccaat    3960 cactcaagag catcgcaaga tgtgtattct ggtcagagac tatagttgat gaaacaaggg    4020
cagcatgcag taatattgct acaacaatgg ctaaaagcat cgagagaggt tatgaccgtt    4080
accttgcata ttccctgaac gtcctaaaag tgatacagca aattctgatc tctcttggct    4140
tcacaatcaa ttcaaccatg acccgggatg tagtcatacc cctcctcaca acaacgacc    4200 tcttaataag gatggcactg ttgcccgctc ctattggggg gatgaattat ctgaatatga    4260
gcaggctgtt tgtcagaaac atcggtgatc cagtaacatc atcaattgct gatctcaaga    4320
gaatgattct cgcctcacta atgcctgaag agaccctcca tcaagtaatg acacaacaac    4380
cgggggactc ttcattccta gactgggcta gcgacccta ctcagcaaat cttgtatgtg    4440
tccagagcat cactagactc ctcaagaaca taactgcaag gtttgtcctg atccatagtc    4500
caaacccaat gttaaaagga ttattccatg atgacagtaa agaagaggac gagggactgg    4560
cggcattcct catggacagg catattatag tacctagggc agctcatgaa atcctggatc    4620
atagtgtcac aggggcaaga gagtctcattg caggcatgct ggataccaca aaaggcttga    4680
ttcgagccag catgaggaag gggggggttaa cctctcgagt gataaccaga ttgtccaatt    4740
```

```
atgactatga acaattcaga gcagggatgg tgctattgac aggaagaaag agaaatgtcc    4800
tcattgacaa agagtcatgt tcagtgcagc tggcgagagc tctaagaagc catatgtggg    4860
cgaggctagc tcgaggacgg cctatttacg gccttgaggt ccctgatgta ctagaatcta    4920
tgcgaggcca ccttattcgg cgtcatgaga catgtgtcat ctgcgagtgt ggatcagtca    4980
actacggatg ttttttgtc ccctcgggtt gccaactgga tgatattgac aaggaaacat    5040
catccttgag agtcccatat attggttcta ccactgatga gagaacagac atgaagcttg    5100
ccttcgtaag agccccaagt cgatccttgc gatctgctgt tagaatagca acagtgtact    5160
catgggctta cggtgatgat gatagctctt ggaacgaagc ctggttgttg gctaggcaaa    5220
gggccaatgt gagcctggag gagctaaggg tgatcactcc catctcaact tcgactaatt    5280
tagcgcatag gttgagggat cgtagcactc aagtgaaata ctcaggtaca tcccttgtcc    5340
gagtggcgag gtataccaca atctccaacg acaatctctc atttgtcata tcagataaga    5400
aggttgatac taactttata taccaacaag gaatgcttct agggttgggt gttttagaaa    5460
cattgtttcg actcgagaaa gataccggat catctaacac ggtattacat cttcacgtcg    5520
aaacagattg ttgcgtgatc ccgatgatag atcatcccag gatacccagc tcccgcaagc    5580
tagagctgag ggcagagcta tgtaccaacc cattgatata tgataatgca cctttaattg    5640
acagagatgc aacaaggcta tacccagagc catagag gcaccttgtg gaatttgtta    5700
catggtccac accccaacta tatcacattt tagctaagtc cacagcacta tctatgattg    5760
acctggtaac aaaatttgag aaggaccata tgaatgaaat ttcagctctc ataggggatg    5820
acgatatcaa tagtttcata actgagtttc tgctcataga gccaagatta ttcactatct    5880
acttgggcca gtgtgcggcc atcaattggg catttgatgt acattatcat agaccatcag    5940
ggaaatatca gatgggtgag ctgttgtcat cgttcctttc tagaatgagc aaaggagtgt    6000
ttaaggtgct tgtcaatgct ctaagccacc caaagatcta caagaaattc tggcattgtg    6060
gtattataga gcctatccat ggtccttcac ttgatgctca aaacttgcac acaactgtgt    6120
gcaacatggt ttacacatgc tatatgacct acctcgacct gttgttgaat gaagagttag    6180
aagagttcac atttctcttg tgtgaaagcg acagaggatg agtaccggac agattcgaca    6240
acatccaggc aaaacactta tgtgttctgg cagatttgta ctgtcaacca gggacctgcc    6300
caccaattcg aggtctaaga ccggtagaga atgtgcagt tctaaccgac catatcaagg    6360
cagaggctat gttatctcca gcaggatctt cgtggaacat aaatccaatt attgtagacc    6420
attactcatg ctctctgact tatctccggc gaggatcgat caaacagata agattgagag    6480
ttgatccagg attcattttc gacgccctcg ctgaggtaaa tgtcagtcag ccaaagatcg    6540
gcagcaacaa catctcaaat atgagcatca aggctttcag acccccacac gatgatgttg    6600
caaaattgct caaagatatc aacacaagca agcacaatct tcccatttca ggggcaatc    6660
tcgccaatta tgaaatccat gctttccgca gaatcgggtt gaactcatct gcttgctaca    6720
aagctgttga gatatcaaca ttaattagga gatgccttga gccaggggag gacggcttgt    6780
tcttgggtga gggatcgggt tctatgttga tcacttataa agagatactt aaactaaaca    6840
agtgcttcta taatagtggg gtttccgcca attctagatc tggtcaaagg gaattagcac    6900
cctatccctc cgaagttggc cttgtcgaac acagaatggg agtaggtaat attgtcaaag    6960
tgctcttaa cgggaggccc gaagtcacgt gggtaggcag tgtagattgc ttcaatttca    7020
tagttagtaa tatccctacc tctagtgtgg ggtttatcca ttcagatata gagaccttgc    7080
```

```
ctgacaaaga tactatagag aagctagagg aattggcagc catcttatcg atggctctgc    7140
tcctgggcaa aataggatca atactggtga ttaagcttat gcctttcagc ggggattttg    7200
ttcagggatt tataagttat gtagggtctc attatagaga agtgaacctt gtataccta     7260 gatacagcaa cttcatctct actgaatctt atttggttat gacagatctc aaggctaacc    7320
ggctaatgaa tcctgaaaag attaagcagc agataattga atcatctgtg aggacttcac    7380
ctggacttat aggtcacatc ctatccatta agcaactaag ctgcatacaa gcaattgtgg    7440
gagacgcagt tagtagaggt gatatcaatc ctactctgaa aaaacttaca cctatagagc    7500
aggtgctgat caattgcggg ttggcaatta acggacctaa gctgtgcaaa gaattgatcc    7560
accatgatgt tgcctcaggg caagatggat tgcttaattc tatactcatc ctctacaggg    7620
agttggcaag attcaaagac aaccaaagaa gtcaacaagg gatgttccac gcttaccccg    7680
tattggtaag tagcaggcaa cgagaactta tatctaggat cacccgcaaa ttctgggggc    7740
acattcttct ttactccggg aacaaaaagt tgataaataa gtttatccag aatctcaagt    7800
ccggctatct gatactagac ttacaccaga atatcttcgt taagaatcta tccaagtcag    7860
agaaacagat tattatgacg ggggtttga acgtgagtg ggttttaag gtaacagtca       7920 aggagaccaa agaatggtat aagttagtcg gatacagtgc cctgattaag gactaattgg    7980
ttgaactccg gaaccctaat cctgccctag gtggttaggc attatttacc tcgagggggc    8040
cggatccact agttctagaa aaaaaaaaa aaaaaaaaa aaaaaaaaa aaaaaaaaa        8100 aaaaaaaaaa aaaaaaaaaa acgtcgcgca ggtgacaatg tcgagctagc tatgaattcc    8160
ccggggagct cactagtgga tccctgcagc tcgagaggcc taattaatta agtcgacgat    8220
ccggctgcta acaaagcccg aaaggaagct gagttggctg ctgccaccgc tgagcaataa    8280
ctagcataac cccttggggc ctctaaacgg gtcttgaggg gttttttgct gaaaggagga    8340
actatatccg gatcgagatc aattctgtga gcgtatggca aacgaaggaa aaatagttat    8400
agtagccgca ctcgatggga catttcaacg taaaccgttt aataatattt tgaatcttat    8460
tccattatct gaaatggtgg taaaactaac tgctgtgtgt atgaaatgct ttaaggaggc    8520
ttccttttct aaacgattgg gtgaggaaac cgagatagaa ataataggag gtaatgatat    8580
gtatcaatcg gtgtgtagaa agtgttacat cgactcataa tattatattt tttatctaaa    8640
aaactaaaaa taaacattga ttaaatttta atataatact taaaaatgga tgttgtgtcg    8700
ttagataaac cgtttatgta ttttgaggaa attgataatg agttagatta cgaaccagaa    8760
agtgcaaatg aggtcgcaaa aaaactgccg tatcaaggac agttaaaact attactagga    8820
gaattatttt ttcttagtaa gttacagcga cacggtatat tagatggtgc caccgtagtg    8880
tatataggat ctgctcccgg tacacatata cgttatttga gagatcattt ctataattta    8940
ggagtgatca tcaaatggat gctaattgac ggccgccatc atgatcctat tttaaatgga    9000
ttgcgtgatg tgactctagt gactcggttc gttgatgagg aatatctacg atccatcaaa    9060
aaacaactgc atccttctaa gattatttta atttctgatg tgagatccaa acgaggagga    9120
aatgaaccta gtacggcgga tttactaagt aattacgctc tacaaaatgt catgattagt    9180
attttaaacc ccgtggcgtc tagtcttaaa tggagatgcc cgtttccaga tcaatggatc    9240
aaggactttt atatcccaca cggtaataaa atgttacaac cttttgctcc ttcatattca    9300
gggccgtcgt tttacaacgt cgtgactggg aaaaccctgg cgttacccaa cttaatcgcc    9360
ttgcagcaca tccccctttc gccagctggc gtaatagcga gaggcccgc accgatcgcc     9420 cttcccaaca gttgcgcagc ctgaatggcg aatggcgcga cgcgccctgt agcggcgcat    9480
```

```
taagcgcggc gggtgtggtg gttacgcgca gcgtgaccgc tacacttgcc agcgccctag    9540
cgcccgctcc tttcgctttc ttcccttcct ttctcgccac gttcgccggc tttccccgtc    9600
aagctctaaa tcggggctc  cctttagggt tccgatttag tgctttacgg cacctcgacc    9660
ccaaaaaact tgattagggt gatggttcac gtagtgggcc atcgccctga tagacggttt    9720
ttcgcccttt gacgttggag tccacgttct ttaatagtgg actcttgttc caaactggaa    9780
caacactcaa ccctatctcg gtctattctt ttgatttata agggattttg ccgatttcgg    9840
cctattggtt aaaaaatgag ctgatttaac aaaaatttaa cgcgaatttt aacaaaatat    9900
taacgtttac aatttcccag gtggcacttt tcggggaaat gtgcgcggaa ccccatttg     9960 tttattttc  taaatacatt caaatatgta tccgctcatg agacaataac cctgataaat   10020
gcttcaataa tattgaaaaa ggaagagtat gagtattcaa catttccgtg tcgcccttat   10080
tccctttttt gcggcatttt gccttcctgt ttttgctcac ccagaaacgc tggtgaaagt   10140
aaaagatgct gaagatcagt tgggtgcacg agtgggttac atcgaactgg atctcaacag   10200
cggtaagatc cttgagagtt ttcgccccga agaacgtttt ccaatgatga gcacttttaa   10260
agttctgcta tgtggcgcgg tattatcccg tattgacgcc gggcaagagc aactcggtcg   10320
ccgcatacac tattctcaga atgacttggt tgagtactca ccagtcacag aaaagcatct   10380
tacggatggc atgacagtaa gagaattatg cagtgctgcc ataaccatga gtgataacac   10440
tgcggccaac ttacttctga caacgatcgg aggaccgaag gagctaaccg cttttttgca   10500
caacatgggg gatcatgtaa ctcgccttga tcgttgggaa ccggagctga atgaagccat   10560
accaaacgac gagcgtgaca ccacgatgcc tgtagcaatg gcaacaacgt tgcgcaaact   10620
attaactggc gaactactta ctctagcttc ccggcaacaa ttaatagact ggatggaggc   10680
ggataaagtt gcaggaccac ttctgcgctc ggcccttccg gctggctggt ttattgctga   10740
taaatctgga gccggtgagc gtgggtctcg cggtatcatt gcagcactgg ggccagatgg   10800
taagccctcc cgtatcgtag ttatctacac gacggggagt caggcaacta tggatgaacg   10860
aaatagacag atcgctgaga taggtgcctc actgattaag cattggtaac tgtcagacca   10920
agtttactca tatatacttt agattgattt aaaacttcat ttttaattta aaaggatcta   10980
ggtgaagatc ctttttgata atctcatgac caaaatccct taacgtgagt ttcgttcca    11040 ctgagcgtca gaccccgtag aaaagatcaa aggatcttct tgagatcctt ttttctgcg    11100 cgtaatctgc tgcttgcaaa caaaaaaacc accgctacca gcggtggttt gtttgccgga   11160
tcaagagcta ccaactcttt ttccgaaggt aactggcttc agcagagcgc agataccaaa   11220
tactgtcctt ctagtgtagc cgtagttagg ccaccacttc aagaactctg tagcaccgcc   11280
tacatacctc gctctgctaa tcctgttacc agtggctgct gccagtggcg ataagtcgtg   11340
tcttaccggg ttggactcaa gacgatagtt accggataag gcgcagcggt cgggctgaac   11400
ggggggttcg tgcacacagc ccagcttgga gcgaacgacc tacaccgaac tgagatacct   11460
acagcgtgag ctatgagaaa gcgccacgct tcccgaaggg agaaaggcgg acaggtatcc   11520
ggtaagcggc agggtcggaa caggagagcg cacgagggag cttccagggg gaaacgcctg   11580
gtatctttat agtcctgtcg gtttcgcca  cctctgactt gagcgtcgat ttttgtgatg   11640
ctcgtcaggg gggcggagcc tatggaaaaa cgccagcaac gcggcctttt tacggttcct   11700
ggccttttgc tggccttttg ctcacatgtt ctttcctgcg ttatcccctg attctgtgga   11760
taaccgtatt accgcctttg agtgagctga taccgctcgc cgcagccgaa cgaccgagcg   11820
```

```
cagcgagtca gtgagcgagg aagcggaaga gcgcccaata cgcaaaccgc ctctccccgc    11880
gcgttggccg attcattaat gcagctggca cgacaggttt cccgactgga aagcgggcag    11940
tgagcgcaac gcaattaatg tgagttagct cactcattag gcaccccagg ctttacactt    12000
tatgcttccg gctcgtatgt tgtgtggaat tgtgagcgga taacaatttc acacaggaaa    12060
cagctatgac catgattacg cc                                             12082

<210> SEQ ID NO 20
<211> LENGTH: 61
<212> TYPE: DNA
<213> ORGANISM: Artificial
<220> FEATURE:
<223> OTHER INFORMATION: AttB1-T7Pol primer

<400> SEQUENCE: 20
ggggacaagt ttgtacaaaa aagcaggctc caccatggaa ttctctgaca tcgaactggc    60
t                                                                    61

<210> SEQ ID NO 21
<211> LENGTH: 64
<212> TYPE: DNA
<213> ORGANISM: Artificial
<220> FEATURE:
<223> OTHER INFORMATION: AttB2-retourT7Pol primer

<400> SEQUENCE: 21
ggggaccact ttgtacaaga aagctgggtt atcacgcgaa cgcgaagtcc gactctaaga    60
tgtc                                                                 64

<210> SEQ ID NO 22
<211> LENGTH: 61
<212> TYPE: DNA
<213> ORGANISM: Artificial
<220> FEATURE:
<223> OTHER INFORMATION: AttBI-SV40nls primer

<400> SEQUENCE: 22
ggggacaagt ttgtacaaaa aagcaggctc caccatggca ccaaaaaaga agagaaaggt    60
a                                                                    61

<210> SEQ ID NO 23
<211> LENGTH: 58
<212> TYPE: DNA
<213> ORGANISM: Artificial
<220> FEATURE:
<223> OTHER INFORMATION: AttB1-N primer

<400> SEQUENCE: 23
ggggacaagt ttgtacaaaa aagcaggctc catggccaca cttttaagga gcttagca      58

<210> SEQ ID NO 24
<211> LENGTH: 60
<212> TYPE: DNA
<213> ORGANISM: Artificial
<220> FEATURE:
<223> OTHER INFORMATION: AttB2-N primer

<400> SEQUENCE: 24
gggaccactt tgtacaagaa agctgggtgt gtactagtct agaagatttc tgtcattgta    60

<210> SEQ ID NO 25
<211> LENGTH: 55
```

```
<212> TYPE: DNA
<213> ORGANISM: Artificial
<220> FEATURE:
<223> OTHER INFORMATION: AttB1-P primer

<400> SEQUENCE: 25
ggggacaagt ttgtacaaaa aagcaggctc catggcagaa gagcaggcac gccat        55

<210> SEQ ID NO 26
<211> LENGTH: 68
<212> TYPE: DNA
<213> ORGANISM: Artificial
<220> FEATURE:
<223> OTHER INFORMATION: AttB2-P primer

<400> SEQUENCE: 26
ggggaccact ttgtacaaga aagctgggtg ttactacttc attattatct tcatcagcat   60
ctggtgga                                                            68
```